United States Patent [19]

Yasueda et al.

[11] Patent Number: 5,607,849

[45] Date of Patent: Mar. 4, 1997

[54] GENE ENCODING TRANSGLUTAMINASE DERIVED FROM FISH

[75] Inventors: Hisashi Yasueda; Kazuo Nakanishi; Masao Motoki; Kazuo Nagase; Hiroshi Matsui, all of Kawasaki, Japan

[73] Assignee: Ajinomoto Co., Inc., Tokyo, Japan

[21] Appl. No.: 583,799

[22] Filed: Jan. 5, 1996

Related U.S. Application Data

[63] Continuation of Ser. No. 164,839, Dec. 9, 1993, Pat. No. 5,514,573, which is a continuation of Ser. No. 4,729, Jan. 14, 1993, abandoned.

[30] Foreign Application Priority Data

Jan. 14, 1992 [JP] Japan .................. 4-005166
Jul. 27, 1992 [JP] Japan .................. 4-199803
Dec. 8, 1992 [JP] Japan .................. 4-328010

[51] Int. Cl.$^6$ .............. C12N 9/10; C12N 5/10; C12N 15/54; C12N 15/63
[52] U.S. Cl. .............. 435/193; 435/320.1; 435/183; 435/69.1; 435/252.33; 435/254.21; 435/254.11; 435/252.31; 536/23.2
[58] Field of Search .............. 536/23.2; 435/69.1, 435/240.2, 320.1, 193, 183

[56] References Cited

U.S. PATENT DOCUMENTS

| | | | |
|---|---|---|---|
| 4,917,904 | 4/1990 | Wakameda et al. ............ | 426/7 |
| 5,156,956 | 1/1992 | Motoki et al. . | |
| 5,420,025 | 5/1995 | Takagi et al. . | |

OTHER PUBLICATIONS

Sambrook et al. "Molecular Cloning: A Laboratory Manual", Cold Spring Harbor Laboratory Press, pp. 11.2–11.57 1989.

Ikura et al. "Expression of Guinea–Pig Liver Transglutaminase cDNA in *Escherichia coli*", European Journal of Biochemistry, vol. 187, pp. 705–711 1990.

Phillips et al. "Genomic Structure of Keratinocyte Transglutaminase", The Journal of Biological Chemistry, vol. 257, No. 4, pp. 2282–2286 Feb. 5, 1992.

Mahler et al. (Eds.) "Biological Chemistry, Second Edition", Harper & Row, New York, pp. 116–119 1971.

Wood et al. "Base Composition–Independent Hybridization in Tetramethylammonium Chloride: A Method for Oligonucleotide Screening of Highly Complex Gene Libraries", Proceedings of the National Academy of Sciences USA, vol. 82, pp. 1585–1588 Mar. 1985.

Lathe "Synthetic Oligonucleotide Probes Deduced from Amino Acid Sequence Data", Journal of Molecular Biology, vol. 183, pp. 1–12 1985.

Gentile et al. "Isolation and Characterization of cDNA Clones to Mouse Macrophage and Human Endothelial Cell Tissue Transglutaminases", The Journal of Biological Chemistry, vol. 266, No. 1, pp. 478–483 Jan. 5, 1991.

Nakanishi et al. "Cloning and Sequence Analysis of cDNA Clones for Bovine Aortic–Endothelial–Cell Transglutaminase", European Journal of Biochemistry, vol. 202, pp. 15–21 1991.

*Primary Examiner*—George C. Elliott
*Attorney, Agent, or Firm*—Oblon, Spivak, McClelland, Maier & Neustadt, P.C.

[57] ABSTRACT

The present invention relates to a DNA fragment having a gene derived from fish which codes for a polypeptide possessing transglutaminase activity, a recombinant plasmid comprising a fish-derived DNA fragment which codes for a transglutaminase, a transformant into which a recombinant plasmid comprising a fish-derived DNA fragment which codes for a transglutaminase is introduced, and a method for the production of a transglutaminase, comprising culturing a transformant containing a fish-derived DNA fragment which codes for a transglutaminase.

14 Claims, 13 Drawing Sheets

```
           1F                              2F
AATTCATCGATTAGTAAGGAGGTTTAAAAT GGCTTCTTATAAAGGTCTGATTGTTGATGT TAATGGTCG
               GTAGCTAATCATTCCTCCAAATTTTACCGA AGAATATTTCCAGACTAACAACTACAATTA CCAGC
(EcoRI) ClaI        1R                              2R 1F                              2F
TTCTCATGAAAACAACCTGGCAC ATCGTACGCGTGAAATCGACCGTGAGCGCCTGA
AAGAGTACTTTTGTTGGACCGTGTAGC ATGCGCACTTTAGCTGGCACTCGCGGACTTCGA
               1R                    2R    HaeII   (HindIII)
```

GENE ENCODING TRANSGLUTAMINASE DERIVED FROM FISH

This is a Continuation of applicaiton Ser. No. 08/164,839 filed on Dec. 9, 1993, U.S. Pat. No. 5,514,573, which is a Continuation of Ser. No. 08/004,729 filed on Jan. 14, 1993, abandoned.

BACKGROUND OF THE INVENTION

1. Field of the Invention

The present invention relates to a DNA fragment having a gene derived from fish which codes for a polypeptide possessing transglutaminase activity, a recombinant plasmid comprising a fish-derived DNA fragment which codes for a transglutaminase, a transformant into which a recombinant plasmid comprising a fish-derived DNA fragment which codes for a transglutaminase is introduced, and a method for the production of a transglutaminase, comprising culturing a transformant containing a fish-derived DNA fragment which codes for a transglutaminase.

2. Discussion of the Background

Transglutaminase (hereafter abbreviated as "TGase") is an enzyme which catalyzes an acyl group transfer reaction of a gamma-carboxyamido group of a glutamine residue in a peptide chain. In the presence of transglutaminase, an epsilon-amino group of a lysine residue in a protein functions as an acyl receptor, thus forming epsilon-(gamma-Gln)-Lys crosslinkings in the protein, or if the lysine and glutamine residues are in two or more protein molecules, epsilon-(gamma-Gln)-Lys bridges are formed between the proteins. Alternatively, if a primary amine such as an amino acid, amino acid derivative, etc. functions as an acyl receptor, transglutaminase introduces the primary amine into the protein. Also, when water functions as an acyl receptor, transglutaminase enzyme catalyzes the deamidation or hydrolysis of a glutamine residue to a glutamic acid residue.

TGase is used in the production of gelatinous food products and cosmetics, as well as yogurt, jelly and cheese, etc. (Japanese Patent Publication 50382/1989). Further, it is used for the production of materials for thermostable microcapsules, carriers for immobilized enzymes, etc.

A calcium ($Ca^{2+}$)-independent TGase from bacteria of the genus Streptoverticillium has been discovered. Some concrete examples of bacteria belonging to this genus include *Streptoverticillium griseocarneum* IFO 12776, *Streptoverticillium cinnamoneum* sub sp. *cinnamoneum* IFO 12852, *Streptoverticillium mobaraense* IFO 13819, etc. (Japanese Patent Application Publication 27471/1989).

Further, TGases derived from certain mammalian animals are also known. These include a TGase derived from guinea pig liver (Connellan, et al., Journal of Biological Chemistry, Vol. 246, p. 1093–1098, 1971), from human or bovine vascular endothelial cells (Gentile, et al., Journal of Biological Chemistry, Vol. 266, p. 478–483, 1991, and Nakanishi, et al., European Journal of Biochemistry, Vol. 202, p. 15–21, 1991), and from human blood coagulation factor XIII (Takahashi, et al., Proc. Natl. Acad. Sci. USA, Vol. 83, p. 8019–8023, 1986).

Heretofore, the sources of TGase available for industrial use have been mammals and bacteria. However, the products with which TGase processing are most common include processed marine (fish) products, a typical example of which is a boiled fish paste known as "kamaboko" (Seki, et al., Nippon Suisan Gakkaishi, Vol. 56, p. 125–132, 1990). The TGase belived to be responsible for the properties of "kamaboko" is apparently an enzyme derived from fish, present in the raw fish materials used in "kamaboko" preparation.

Prior to the present invention, no information has been available concerning a TGase gene from fish. However, a TGase from fish will both widen the range of TGase use and provide enzyme-processed fish products having similarities to natural fish products. Thus, the cloning, identification and expression of a fish TGase gene is highly desired, and may lead to a supply of fish-derived TGase at a low price.

SUMMARY OF THE INVENTION

Accordingly, one object of the present invention is to provide a novel DNA fragment which codes for a polypeptide derived from fish which possesses TGase activity.

A further object of the present invention is to provide a recombinant plasmid comprising a DNA fragment which codes for a polypeptide derived from fish which possesses TGase activity.

A further object of the present invention is to provide a transformant containing a DNA fragment which codes for a polypeptide derived from fish which possesses TGase activity.

A further object of the present invention is to provide a method for the production of a polypeptide derived from fish which possesses TGase activity, compriing culturing a transformant containing a DNA fragment which codes for a polypeptide derived from fish which possesses TGase activity.

A further object of the present invention is to provide a purified and isolated polypeptide derived from fish which possesses TGase activity.

These and other objects of the invention which will become apparent from the following detailed description of the invention, have been achieved by a DNA fragment from fish which contains a gene which codes for TGase, expression of a gene which codes for TGase by genetic engineering methods, and culturing transformants transformed with an expression vector containing a gene which codes for TGase.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figures 1, 4:
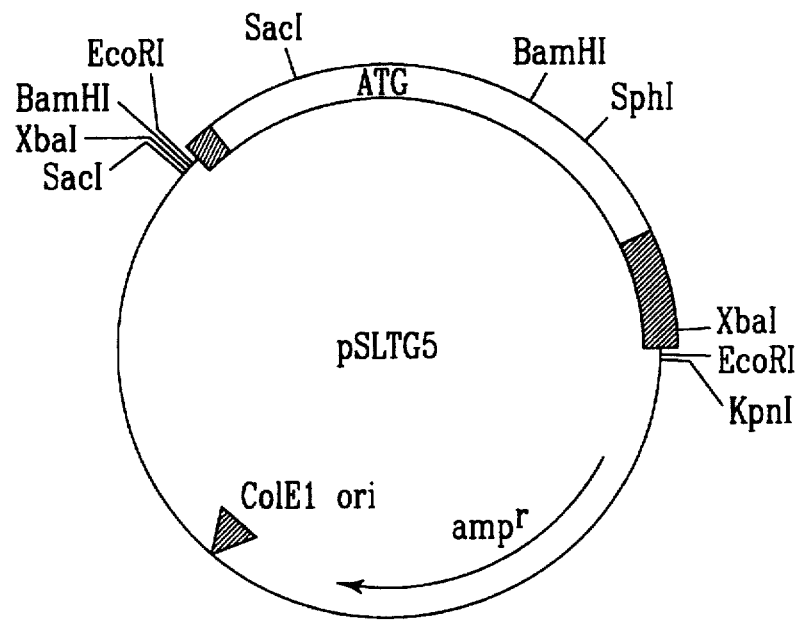
FIG. 1 shows a restriction enzyme map for plasmid pSLTG5 which possesses the acquired cDNA with a gene coding for *Pagrus major* transglutaminase.
FIG. 4 shows a base sequence listing of chemically synthesized DNA-1 (SEQ ID NO:1). This shows the DNA base sequence which contains a consensus SD (Shine-Dalgarno) sequence from *E. coli* and codes for the region from methionine at the amino terminus of *Pagrus major* transglutaminase to the 32nd amino acid, leucine.

One recombinant transglutaminase for reforming food proteins is derived from a guinea pig. This is a comparative TGase. Transglutaminases derived from fish are superior to guinea pig TGase for industrial uses for the following reasons:

(1) Fish has been eaten by human beings for a long period of time, even raw. Therefore, the safety of fish transglutaminase is extremely high. Future costs for investigation of the safety of fish-drived transglutaminase may be smaller than that of one derived from other living things.

(2) Regarding the difference in the enzymatic characteristics between the fish-derived transglutaminase and one derived from other mammals, especially for application thereof to fish paste products, specifically mentioned are the difference in the reactivity of the enzyme and the production cost to be influenced by the difference in the deactivating conditions of the enzyme to be reacted (this will be referred to in the following examples) and also the difference in the qualitative effects such as the natural taste and tooth feeling (expression of elasticity) of the reaction products. In fact, it has been found that a fish transglutaminase has a high reactivity to a fish actomyosin (refer to the following examples).

(3) The difference in the productivity of a recombinant transglutaminase with microorganisms is also an important problem for consideration of the practical use of the transglutaminase. Ikura et al have already reported the production of a guinea pig-derived transglutaminase with *Escherichia coli* (Eur. J. Biochem., Vol. 187, 705–711, 1990). However, the amount of it to be produced is extremely small. That is, the transglutaminase in an extract of transglutaminase-producing cells was such that could only be detected with an antibody thereto (the amount of the transglutaminase to be produced is about 2.6 mg or so per liter of the culture medium). As opposed to this, where the DNA fragment coding for the fish-derived transglutaminase of the present invention is applied to a host of *E. coli*, it shows a productivity of producing about 10% to 15% of *E. coli*-derived SDS-soluble total proteins, reaching an expression quantity about 100 times or higher than that of the guinea pig-derived transglutaminase. Thus, there is a high possibility that the fish-derived transglutaminase has a gene structure suitable to production of a recombinant one. (This will be explained in the following examples.)

The above-mentioned various characteristics of the fish-derived transglutaminase yield great advantages in industrial use, especially for reformation of food proteins therewith. The current shortage of marine resources, due to the 200 nautical sea mile restriction and the total fish catch quota restriction in the fishery sea area, causes a serious problem in the elevation of the raw material cost in producing marine products. For instance, use of the enzyme of the present invention with other edible protein can reduce the concentration of the fish paste material in processed marine products, and lead to the effective use of the underutilized marine resources.

On the other hand, the fish-derived transglutaminase is quite different from a microorganism- or bacteria-derived transglutaminase (hereinafter referred to as BTG), with respect to the structure and the reaction mechanism. For instance, BTG does not need calcium ion for expressing the enzymatic function thereof. Due to this, differentiation in use of the BTG from the fish-derived transglutaminase to be obtained by the present invention would be necessary for the intended protein to be utilized.

As to the differences between BTG and the fish-derived transglutaminase, where the fish-derived transglutaminase is reacted with a substrate or where the reaction is desired to be stopped, the calcium ion dependence could be utilized so as to control the reaction time and the reactivity of the enzyme. Also, the fish-derived transglutaminase is less stable against heat than BTG, so the fish-derived transglutaminase can be denatured at relatively low temperature, which can be a merit for production of anti-heat food.

One method for obtaining a fish-derived DNA fragment containing a gene which codes for a polypeptide possessing transglutaminase activity employs a probe based on a synthesized DNA fragment coding for amino acid residues near the active center of guinea pig transglutaminase. An example of such a DNA fragment is one which codes for the amino acid sequenceof SEQ ID NO:2. Such probes are used for plaque hybridization isolation of the desired DNA fragment from the cDNA prepared from tissue of fish. Prior to the present invention, the degree of homology between guinea pig transglutaminase and fish transglutaminase, as well as between their corresponding genes, was completely unknown. Thus, the successful cloning of a DNA fragment encoding a fish transglutaminase using this method is unexpected.

Other methods of acquiring a fish-derived DNA fragment containing a gene which codes for a polypeptide possessing transglutaminase activity include the following:

(A) Isolating and purifying a fish-derived polypeptide which possesses transglutaminase activity, determining the amino acid sequence and chemically synthesizing the corresponding base sequence encoding the determined amino acid sequence;

(B) Synthesizing a portion of the DNA sequence corresponding to the determined amino acid sequence, and hybridizing or "probing" the synthesized portion of DNA with a cDNA bank or genomic DNA bank of the fish with the synthesized portion. Cloning may then be performed by the hybridization method or the polymerase chain reaction (PCR) method; and (C) Translating mRNA transcribed from cDNA in an in vitro wheat germ or rabbit reticulocyte translation system, determining the section of mRNA corresponding to a polypeptide which possesses transglutaminase activity, and cloning the corresponding cDNA fragment.

Examples of DNA fragments having the gene which codes for a fish-derived polypeptide possessing transglutaminase activity according to the present invention include those coding for a polypeptide selected from the group consisting of SEQ ID NOS:4, 6, 8, 10, 31, 33, 70 and 72.

The DNA fragment may include a variety of different base sequences, from the point of view of the degeneracy of the genetic codon. Appropriate base sequences may be easily selected and prepared by one skilled in the art, depending on the various elements of the gene expression system.

For example, a particular codon may be preferred over a degenerate codon, depending on the nature of the host cell, or to avoid the formation of a secondary structure in the transcribed RNA, etc. Such considerations may be, and preferably are, taken into account in the preparation of a DNA fragment suitable for the present invention.

The present DNA fragment may result from cloning a natural occurring entity, or may be chemically synthesized DNA. The DNA fragment of the present invention may also have a naturally occurring or artificial substitution, deletion, insertion or inversion of one or more bases in the base sequence.

The present DNA fragment includes mutants having substitution, deletion or insertion of base sequences on the basis of the difference in the individualities of fishes and of the difference in the respective organs and tissues of them. The present DNA fragment has a multiplicity derived from mult-copies of gene-dosage, for example, which may be a pseudogene. However, such still contain an essentially equivalent DNA fragment capable of expressing the transglutaminase activity. The presence of them is described in the following examples.

Concrete examples of DNA fragments suitable for the present invention include SEQ ID NOS:3, 5, 7, 9, 28, 30, 32, 69 and 71, which coincide with a sequence from a natural source (see Examples 1, 2 and 6 below). Further examples of the DNA fragment of the present invention include those having a sequence containing SEQ ID NO:1, and those having a sequence which encodes a polypeptide selected from the group consisting of SEQ ID NO:4, SEQ ID NO:6, SEQ ID NO:8, SEQ ID NO:10, SEQ ID NO:31, SEQ ID NO:33, SEQ ID NO:70 and SEQ ID NO:72, and those encoding a protein having SEQ ID NO:20, one of SEQ ID NOS:34–45 or a combination thereof, one of SEQ ID NOS:46–51 or a combination thereof, or one of SEQ ID NOS:52–68 or a combination thereof.

The present invention may provide the desired enzyme through expression of a fish-derived transglutaminase gene in a microorganism transformed by recombinant genetic technology. A recombinant plasmid useful in the present invention may be prepared by insertion of a DNA fragment having the fish-derived gene which codes for a polypeptide possessing transglutaminase into a publicly-known or commercially-available expression vector corresponding to the desired expression system, using a publicly-known, conventional method.

Suitable methods are generally described by Maniatis et al ("Molecular Cloning," Cold Spring Harbor Laboratory, Cold Spring Harbor, New York (1982)) and Sambrook et al, ("Molecular Cloning: A Laboratory Manual," Cold Spring Harbor Laboratory, Cold Spring Harbor Press, (1989)), and are adapted to correspond to the selected expression system. Expression vectors for *E. coli* include plasmids which express a fused protein composed of T7gene10, a linker peptide and a desired protein (more specifically, the XPRESS SYSTEM™, manufactured by Invitrogen Co.), and plasmids which express a fused protein composed of glutathione-S-transferase and a desired protein (more specifically, the pGEX-2T or pGEX-3T vector plasmid, manufactured by Pharmacia LKB Co.). More preferable expression vectors are pBSF2-SD7 and pT13sNco.

An example of an expression vector for yeast of the genus Saccharomyces is pYES2 (available from Invitrogen Co.), which may use a GAL1 promoter from the gene which codes for galactokinase, for the expression of a foreign gene.

The present invention also relates to transformants obtained by introduction of a recombinant plasmid which carries the transglutaminase gene. Some organisms which can be used for the host of transformation include procaryotic cells such as *E. coli, Bacillus subtilis*, etc. as well as eucaryotic cells such as yeast, fungus, etc. Thus, a way has been found for the efficient mass production of fish-derived TGase.

The host organism for transformation is preferably *E. coli* or yeast, more preferably the *E. coli* HB101 or *Saccharomyces cerevisiae* INVSC2 strain. The transformants of the present invention are capable of producing and accumulating the fish-derived transglutaminase enzyme in the cells or in the culture medium by the expressing the recombinantly-introduced transglutaminase gene.

Finally, the present invention relates to a method for the production of a polypeptide possessing transglutaminase activity, by culturing the above-mentioned transformant. The culturing conditions may be determined as deemed appropriate by one skilled in the art depending on the type of host used. Also, the expressed enzyme, which is accumulated in the cells or secreted into the culture medium or both, may be isolated and purified using any one or a combination of publicly-known, conventional methods.

Concretely, in a purification process similar to that applied to natural transglutaminase from the tissues, this recombinant transglutaminase(s) can be purified from the crude extracts. It has not been reported that transglutaminase derived from fish possess saccharide chains. The fish-derived transglutaminase produced in *E. coli* may not be added with any saccharide chains, but the transglutaminase produced in yeast may be added with some saccharide chains in accordance with the function of the glycosylation mechanism in yeast cells.

Other features of the present invention will become apparent in the course of the following descriptions of exemplary embodiments which are given for illustration of the invention, and are not intended to be limiting thereof.

EXAMPLES

1. A DNA fragment having a gene which codes for transglutaminase from *Pagrus major*

Using a polytron and a teflon homogenizer, 1.3 g of the liver from *Pagrus major* was crushed in a solution (20 ml)

of 4M guanidine thiocyanate and 1% beta-mercaptoethanol. After 0.5% sodium lauryl sarcosinate was added to and dissolved in the resulting cell suspension, the obtained solution was passed through a 23 gauge hypodermic needle 10 times to cut up the chromosomal DNA. Next, the solution was centrifuged at 4° C., 5000 rpm for 20 minutes and the supernatant obtained. The total RNA was further purified by conventional CsCl density gradient centrifugation of the supernatant (Sambrook et al, "Molecular Cloning: A Laboratory Manual," Cold Spring Harbor Laboratory, Cold Spring Harbor Press, 1989). The total amount of RNA obtained was 3.8 mg.

Of this total RNA, 1.3 mg was supplied to an mRNA purifying kit (obtained from Clontech) using an oligo (dT)-cellulose column, and approximately 20 μg of purified mRNA molecules were obtained.

Of the obtained mRNA, 8 μg were used as a template for cDNA preparation. A random primer was used for cDNA synthesis, and a You-prime cDNA synthesis kit (obtained from Pharmacia) was used to synthesize double-stranded cDNA. The obtained cDNA was then incorporated into a λ-phage vectro-λZapII (obtained from Stratagene) at its restriction enzyme site EcoRI, after which a GIGAPACK II GOLD (obtained from Stratagene) packaging kit was used to prepare and acquire the *Pagrus major* cDNA library incorporated in the phage. The titer of this library was $1.2 \times 10^6$ pfu/μg vector.

A sample of host *E. coli* XL1-Blue cells were infected with $6.0 \times 10^4$ pfu of phage from the above *Pagrus major* cDNA library, after which the infected cells were spread at $1.5 \times 10^4$ pfu per plate onto four 150 mm diameter agar plates. The cells were cultured at 37° C. for about 9.5 hours, and then the phage plaques formed on the plates were transferred onto a nylon membrane (HIBOND-N, manufactured by Amersham). Next, the nylon membrane was treated with an alkali to denature the DNA, neutralized and washed. Then, the membrane was treated at 80° C. for 3 hours to immobilize the DNA onto the membrane.

Prehybridization of the prepared nylon membrane was then effected at 42° C. for 2 hours, followed by hybridization at 42° C. for 16 hours. The composition of the prehybridization solution was 6X SSC (composition of 1X SSC: 0.15M NaCl, 0.015M sodium citrate, pH 7.0), 5X Denhardt's solution (composition of 1X Denhardt's solution: 0.02% BSA, 0.02% Ficoll, 0.02% polyvinyl pyrrolidone), 20% formamide, 100 μg/ml of herring testis DNA and 0.1% SDS. Also, the DNA probe used for the hybridization was a synthesized DNA fragment (5'-GTCAAGTACGGCCAGT-GCTGGGTCTTCGC-3', SEQ ID NO:11; Ikura et al, Biochemistry, 27, 2898–2905, 1988) encoding amino acid residues located near the active center of guinea pig transglutaminase, labeled at the 5' terminal end with [gamma-$^{32}$P] ATP. The candidate strains for the positive clones obtained by this screening were further subjected to A second and third screening to finally obtain 4 positive clones.

The each infected cell maintaining the above-mentioned respective 4 positive cDNA clones were then infected with helper phage (R408) to transform the cDNA derived from each of the positive clones into phagemid vector pBluescriptSK(-). The length of the inserted cDNA of each of the 4 clones was 0.5 kbp (kilobase pairs), 1.5 kbp, 2.5 kbp and 1.0 kbp, and the clones were named pSLTG2, pSLTG4, pSLTG5 and pSLTG6, respectively.

Next, a restriction enzyme map for each of the cDNA clones was made, and Southern blotting analysis was done with the inserted cDNA of pSLTG5 as the probe. As it was made clear that pSLTG5 (with inserted cDNA length 2.5 kbp) included the other 3 cDNA clones, the DNA base sequence for the inserted cDNA of pSLTG5 was determined. Analysis of the base sequence was done with a Sequenase Version 2.0 (available from U.S.B. Co.) kit, according to conventional methods. The results showed a DNA sequence containing 2520 base pairs (SEQ ID NO:5). Also, the restriction enzyme map of pSLTG5 is shown in FIG. 1.

The DNA sequence contained a segment which showed a very high degree of homology with the DNA probe used (SEQ ID NO:11). The amino acid sequence deduced from the base sequence of the inserted cDNA of pSLTG5 corresponds to SEQ ID NO:4. This amino acid sequence includes an active center sequence of 8 amino acid residues, Tyr-Gly-Gln-Cys-Trp-Val-Phe-Ala (SEQ ID NO:2) (Nakanishi et al, Eur. J. Biochem., 202, 15–21, 1991) which is present both in transglutaminase derived from guinea pig liver and in human blood clotting factor XIII. The *E. coli* strain (AJ12673) transformed with the DNA plasmid pSLTG5 which contains the *Pagrus major* transglutaminase cDNA obtained as described above, *Escherichia coli* XL1-Blue/pSLTG5, is deposited with the Fermentation Research Institute, Agency of Industrial Science and Technology (1-3, Higashi, 1-chome, Tsukuba-shi, Ibaraki-ken 305, Japan) under the deposit number FERM BP-4114.

2. A DNA fragment having a gene which codes for transglutaminase from *Theragra chalcogramma* (Alaska pollack)

Using a polytron and a teflon homogenizer, 2.3 g of Alaskan pollack liver were crushed in a solution (20 ml) of 4M guanidine thiocyanate and 1% beta-mercaptoethanol. After 0.5% sodium lauryl sarcosinate was added to and dissolved in the cell suspension, the resulting solution was passed through a 23 gauge hypodermic needle 10 times to cut up the chromosomal DNA. Next, the solution was centrifuged at 4° C., 10,000 rpm for 20 minutes and the supernatant obtained. The total RNA was further purified by conventional CsCl density-gradient centrifugation of the supernatant (Sambrook et al, "Molecular Cloning: A Laboratory Manual," Cold Spring Harbor Laboratory, Cold Spring Harbor Press, 1989). The total amount of RNA obtained was 7.2 mg. Of this total RNA, 2.3 mg was subjected to an mRNA purifying kit (available from Clontech) using an oligo (dT)-cellulose column, and approximately 23 μg of purified mRNA molecules were obtained.

Of the obtained mRNA, 4 μg were used as a template for cDNA synthesis. A random primer was used for DNA synthesis, and a You-prime cDNA synthesis kit (available from Pharmacia) was used to synthesize double-stranded cDNA. The obtained cDNA was then incorporated into lambda-phage vector-lambda ZapII (available from Stratagene) at its restriction enzyme cutting site EcoRI, after which a GIGAPACK II GOLD (available from Stratagene) packaging kit was used to produce and acquire an Alaska pollack cDNA library, incorporated in the phage. The titer of the library was $4.1 \times 10^5$ pfu/μg vector.

A sample of host *E. coli* XL1-Blue cells were infected with $5.8 \times 10^4$ pfu of phage from the Alaska pollack cDNA library, after which it was spread at $1.5 \times 10^4$ pfu per plate onto 4 agar plates of 150 mm diameter. The cells were cultured at 37° C. for about 9.5 hours, and then the phage plaques formed on the plates were transferred onto a nylon membrane (HIBOND-N, manufactured by Amersham). Next, the nylon membrane was treated with an alkali to denature the DNA, neutralized and washed. Then, the membrane was treated at 80° C. for 3 hours to immobilize the DNA onto the membrane.

Prehybridization of the prepared nylon membrane was then effected at 42° C. for 2 hours, followed by hybridization at 42° C. for 16 hours. The composition of the prehybridization solution was 6X SSC (composition of 1X SSC: 0.15M NaCl, 0.015M sodium citrate, pH 7.0), 5X Denhardt's solution (composition of 1X Denhardt's solution: 0.02% BSA 0.02% Ficoll, 0.02% polyvinyl pyrrolidone), 20% formamide, 100 μg/ml of herring testis DNA and 0.1% SDS. A DNA probe to be used for the hybridization was based on a DNA fragment of approximately 300 base pairs which may code for the amino acid sequence of the region near the active center, which could be cut off from *Pagrus major* liver transglutaminase cDNA. The DNA fragment was obtained from *Pagrus major* liver cDNA using restriction enzymes ClaI and BamHI, followed by random labelling with [α-$^{32}$P] dCTP. The candidate strains for the positive clones obtained by this screening were further subjected to second and the third screenings to finally obtain 8 positive clones.

Figure 2:
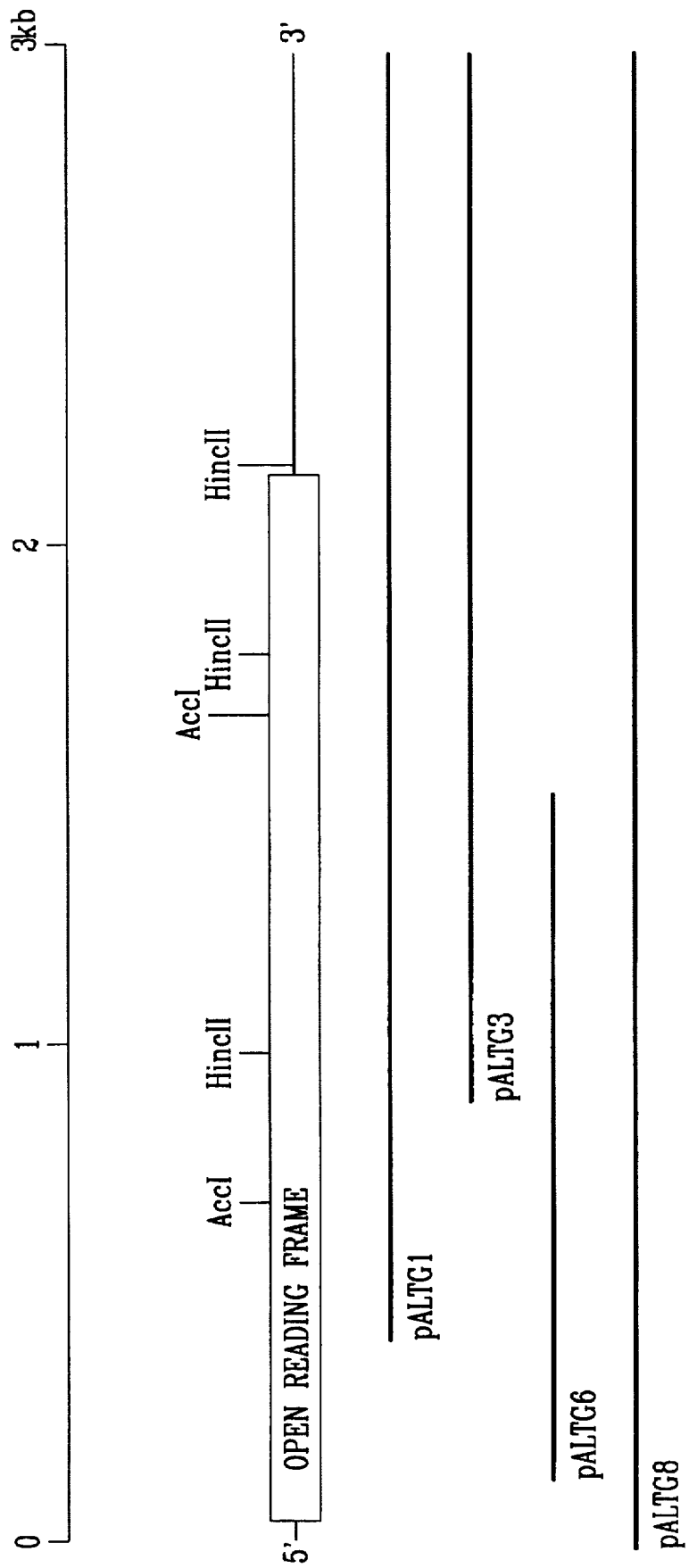
FIG. 2 shows the correlation among cDNA clones which codes for *Theragra chalcogramma* (Alaska pollack) transglutaminase, and the restriction enzyme map for the cDNA.

The each infected cell possessing the above-mentioned respective 8 positive cDNA clones was then infected with helper phage (R408) to transfer the cDNA derived from each of the positive clones into phagemid vector pBluescript SK(-). The eight clones were named pALTG1, pALTG2, pALTG3, pALTG6, pALTG7, pALTG8, pALTG9 and pALTG10, respectively. Of these, the lengths of the inserted cDNA of pALTG1, pALTG3, pALTG6 and pALTG8 were verified, a restriction enzyme map was made, and the cDNA base sequences were analyzed at the 5' end and the 3' end to find the correlation between each clone, shown in FIG. 2. Here, a Fluorescent Primer Cycle Sequencing Kit (manufactured by A.B.I. Co.) was used for analysis of the base sequences.

Next, synthetic primers (20 bases) for the sequencing were prepared, based on a portion of the base sequence of the obtained cDNA, to determine the entire base sequence of the inserted cDNA of pALTG8. Analysis of the base sequence was done by conventional methods, using a Sequenase Version 2.0 (available from U.S.B. Co.) kit. The results showed a DNA sequence of 2921 base pairs (SEQ ID NO:9). The amino acid sequence deduced from SEQ ID NO:9 corresponds to SEQ ID NO:8. This amino acid sequence includes an active center sequence of 8 amino acid residues, Tyr-Gly-Gln-Cys-Trp-Val-Phe-Ala (SEQ ID NO:2), which is present both in transglutaminase derived from guinea pig liver and in human blood clotting factor XIII. The *E. coli* strain (AJ12709) transformed with the DNA plasmid pALTG8, containing the Alaska pollack transglutaminase cDNA obtained as described above, *Escherichia coli* XLI-Blue/pALTG8, is deposited with the Fermentation Research Institute, Agency of Industrial Science and Technology (1-3, Higashi, 1-chome, Tsukuba-shi, Ibaraki-ken 305, Japan) under the deposit number FERM BP-4115.

Alaska pollack-derived transglutaminase of expressing in other tissues than liver has also been investigated. For instance, cloning of a transglutaminase cDNA from Alaska Pollack muscular tissue has been attempted.

11.5 g of Alaska Pollack muscular tissue were ground in 80 ml of an 1% beta-mercaptoethanol solution of 4M guanidine thiocyanate, using polytron and teflon homogenizer. 0.5% sodium lauryl sarcocinate was added to and dissolved in the resulting cell suspension, and the solution was passed through a 23-gauge hypodermic needle seven times and successively through a 25-gauge injection needle seven times, whereby the chromosomal DNA was fragmented. Next, the solution was subjected to centrifugation of 10,000 rpm for 20 minutes at 4° C. or lower, and the supernatant was collected. From the supernatant, a complete RNA was purified by CsCl density gradient centrifugation of a conventional manner (refer to Sambrook et al, "Molecular Cloning: A Laboratory Manual," Cold Spring Harbor Laboratory, Cold Spring Harbor Press (1989)). The amount of the thus obtained complete RNA was 2.1 mg. 1.7 mg of it was applied to an mRNA purifying kit (Clontech) using an oligo(dT)-cellulose column, to purify the mRNA molecule, the yield of which was about 21 micrograms.

Of the thus obtained mRNA, 3.2 micrograms were used as a template for synthesis of cDNA. For synthesis of cDNA, a random primer was used, and a Time Saver cDNA synthesis kit (Pharmacia) for preparing a double-stranded cDNA was used.

Plaque hybridization using the above cDNA library, was effected in the same manner as for the DNA fragment coding for transglutaminase derived from Alaska pollack liver, but no positive cDNA clone could be obtained. Therefore, a cDNA fragment was obtained by the method which will be mentioned below in detail.

The oligonucleotides as synthesized on the basis of the gene base sequence of Alaska pollack liver-derived transglutaminase, using the prepared Alaska pollack muscular cDNA group as a template, were used as primers, and a cDNA fragment of Alaska pollack muscular transglutaminase was specifically amplified by a PCR method (polymerase chain reaction method) using Amplitaq DNA Polymerase (Takara Shuzo).

Figure 10:
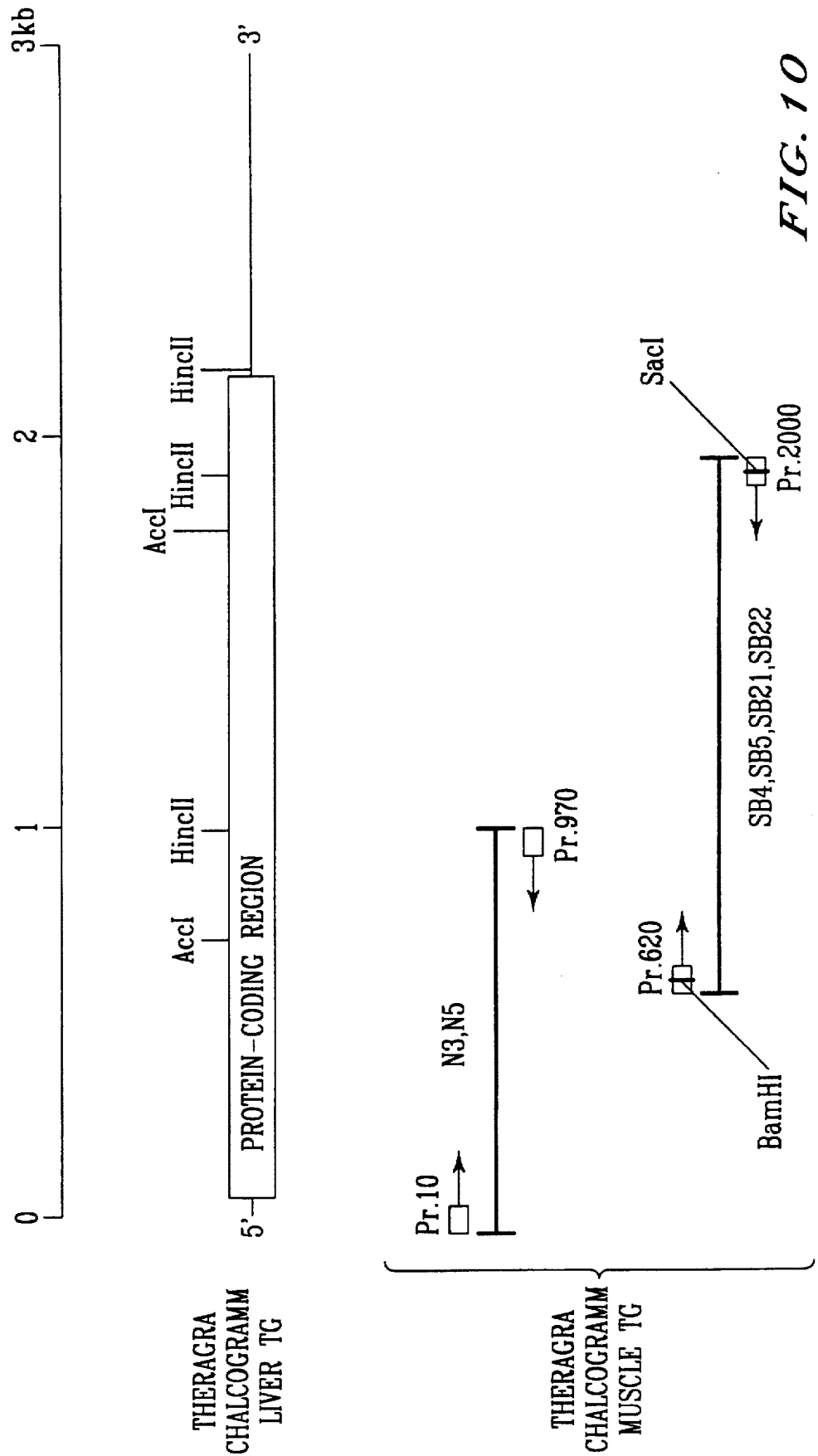
FIG. 10 shows the restriction enzyme cutting sites in a cDNA clone coding for transglutaminase derived from *Theragra chalcogramma* muscle.

As shown in FIG. 10, Pr. 10 (5'-TTGGAAGCTTGTAA-GAGCAACTCTTGGAAA-3'; SEQ ID NO:21) and Pr. 970 (5'-TTGTACACTCGATCGATGGAGAGGT-3'; SEQ ID NO:22) were both used as primers for synthesizing the cDNA fragment, for the 5' terminal region (the region coding for N-terminal region of transglutaminase) in the expected Alaska pollack muscle-derived transglutaminase cDNA structure. After PCR, a DNA fragment of about 980 bp was amplified. Next, the terminal of the fragment was made blunt and then inserted into the restriction enzyme HincII cleaved site of pUC18 vector.

For the gene amplification of the center region, Pr. 620 (5'-TCTGCTTTGGGATCCTTGACCGCT-3'; SEQ ID NO:23) and Pr. 2000 (5'-TGAAGGAGAGCTCCACAGA-CACA-3'; SEQ ID NO:24) were both used as synthetic oligonucleotide primers. Into these primers, were artificially inserted a restriction enzyme BamHI cleavage recognizing site and a restriction enzyme SacI cleavage recognizing site, respectively. After PCR reaction, the amplified DNA fragment of about 1.4 kbp was prepared, and this was digested with the preceding enzymes to give DNA fragments, which were inserted into the same restriction enzyme sites of pBluescript IISK- to obtain cDNA clones.

Further, for amplification of the cDNA fragment in the 3' terminal region (the region coding for C-terminal region of transglutaminase), the intended region was first amplified with PCR primers Pr. 10-1F (5'-ATGATGTCAAAGGCT-GTCAC-3'; SEQ ID NO:25) and Pr. 8-1R (5'-TCTTAC-CATATAAGTTGTAA-3'; SEQ ID NO:26). However, since the primers caused amplification of other small fragments than the intended DNA fragment, the thus amplified DNA group was again subjected to gene amplification, using the same primer Pr. 10-1F and a novel primer of Pr. 3-2F2R (5'-ATTGATTAACAACAAAATGG-3'; SEQ ID NO:27) as templates. As a result, a DNA fragment of about 800 bp was amplified. Both terminals of the present cDNA fragment were also made blunt in the same manner as mentioned above, and the resulting cDNA fragments were inserted into the restriction enzyme EcoRV site of pBluescript IISK-.

A plasmid having the cDNA fragment having each of the above-mentioned three regions was applied to *E. coli* XL1-

Blue for transformation, whereby N-terminal clones of Nos. N-3, N-4 and N-5, center region clones of Nos. SB-4, SB-5, SB-21, SB-22, and SB-30 and C-terminal clones of Nos. C-6, C-9 and C-13 were obtained. Next, the base sequence of each of the above-mentioned eleven DNA clones was sequenced by a known method using Applied Biosystems' Taq dideoxy Terminator Cycle Sequencing Kit. As a result, two kinds of genes coding for transglutaminase were present in Alaska pollack muscule, the one having DNA sequence as shown as SEQ ID NO:28 in the Sequence List and the other having DNA sequence as same structure as the Alaska pollack liver-derived transglutaminase cDNA as shown as SEQ ID NO:7.

From the above, it was clarified that the transglutaminase of SEQ ID NO:7 is an Alaska pollack transglutaminase as expressed beyond the kind of the organ; and that the transglutaminase of SEQ ID NO:28, though not obtained as a cDNA of a complete length, was different from the liver-derived transglutaminase only in the point of a several-base substitution, a base deletion of 12 bp and a base insertion of 3 bp in the structural gene. Thus, both genes were clarified to be highly homologous to each other.

An *E. coli* strain (AJ 12790) of *E. coli* XLI-Blue/N3 having plasmid N3 containing a part of the Alaska pollack muscle-derived transglutaminase cDNA fragment (SEQ ID NO:51) obtained in the above manner has been deposited in Fermentation Research Institute of Japan as FRI Deposition No. 4147 (FERM BP-4147); an *E. coli* strain (AJ 12791) of *E. coli* XLI-Blue/N5 having plasmid N5 as FRI Deposition No. 4148 (FERM BP-4148); an *E. coli* strain (AJ 12792) of *E. coli* XLI-Blue/SB4 having plasmid SB4 as FRI Deposition No. 4149 (FERM BP-4149); an *E. coli* strain (AJ 12793) of *E. coli* XLI-Blue/SB5 having plasmid SB5 as FRI Deposition No. 4150 (FERM BP-BP-4150); an *E. coli* strain (AJ 12794) of *E. coli* XLI-Blue/SB21 having plasmid SB21 as FRI Deposition No. 4151 (FERM BP-4151); and an *E. coli* strain (AJ 12795) of *E. coli* XLI-Blue/SB22 having plasmid SB22 as FRI Deposition No. 4152 (FERM BP-4152).

Figure 3:
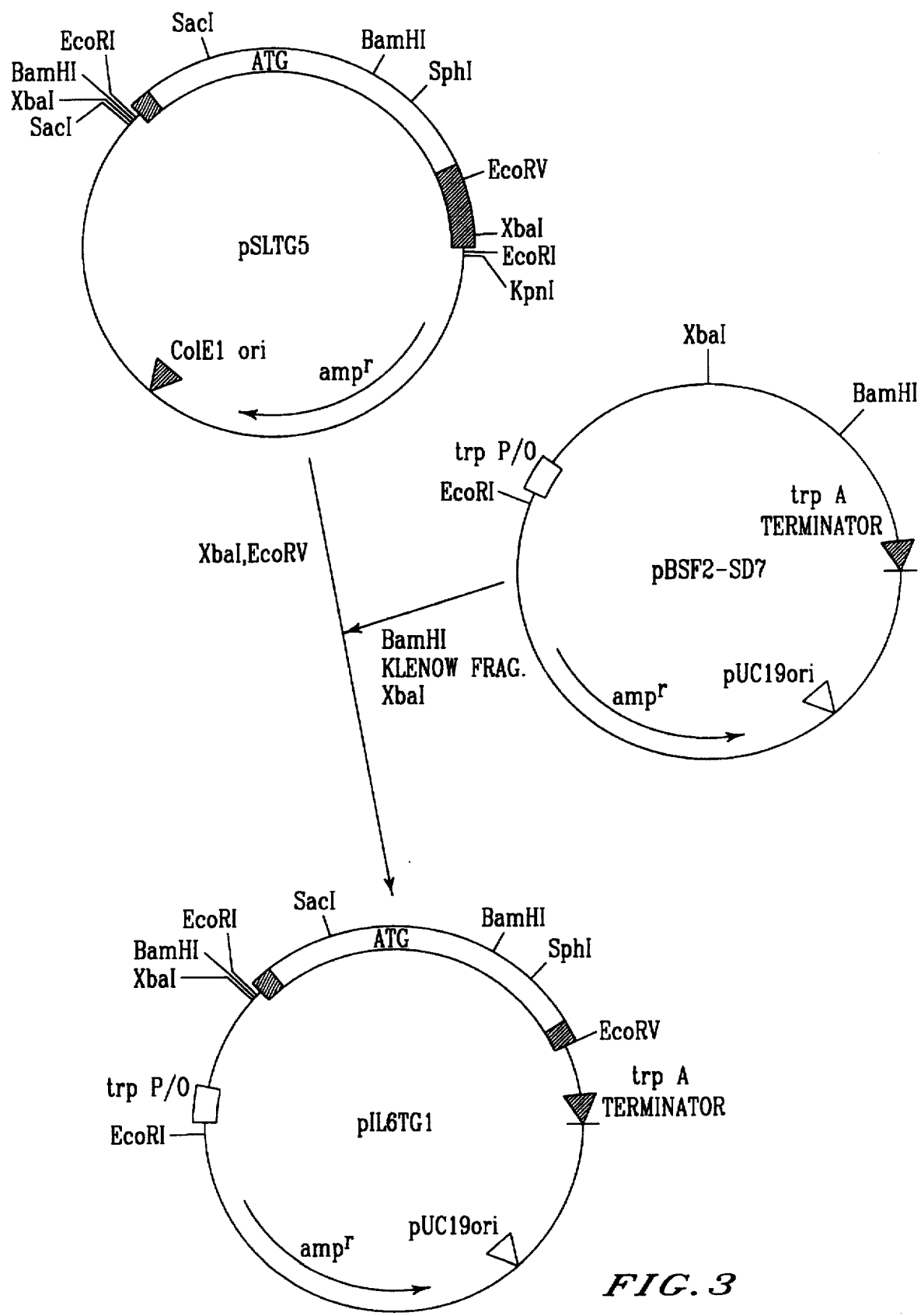
FIG. 3 shows a process for the construction of plasmid pIL6TG1, used for the expression of *Pagrus major* transglutaminase.

3. Construction of plasmid pIL6TG1 which express the *Pagrus major* transglutaminase gene, its introduction into *E. coli*, and verification of physiological activity of a TGase produced by the transformant Plasmid pSLTG5 having the *Pagrus major* transglutaminase gene (cDNA) prepared in the above example was digested with restriction enzymes XbaI and EcoRV, as shown in FIG. 3, and a DNA fragment containing the transglutaminase cDNA was obtained. In a separate procedure, expression vector pBSF2-SD7 possessing a tryptophan promoter and trpA terminator was digested with BamHI. The DNA cutting end was then made flat with Klenow enzyme, then treated with XbaI to obtain a large DNA fragment possessing a tryptophan promoter. Expression plasmid pBSF2-SD7 is the plasmid listed in *Bio/Technology*, 8, pp. 1036–1040, 1990.

The two DNA fragments obtained by the above-described treatment were ligated together with T4 DNA ligase to obtain the *Pagrus major* transglutaminase cDNA expression plasmid pIL6TG1. Verification of the DNA base sequence of this pIL6TG1 showed that one GC base pair was missing at the BamHI cleavage site, making it clear that the EcoRV site was present upstream from the trpA terminator in the plasmid. A conventional method was used to introduce pIL6TG1 into *E. coli* HB101, and a transformant, *Escherichia coli* HB101/pIL6TG1, (AJ12730)was prepared. AJ12730 is deposited with the Fermentation Research Institute, Agency of Industrial Science and Technology (1-3, Higashi, 1-chome, Tsukuba-shi, Ibaraki-ken 305, Japan) under the deposit number FERM BP-4116.

A colony of the acquired transformant was applied onto an agar plate containing 200 µg/ml of ampicillin, and cultured at 30° C. overnight, after which approximately 2 cm$^2$ of the lawn of growing cells from the plate were inoculated into a Sakaguchi flask containing 100 ml of an M9 casamino acid culture medium supplemented with 2% glucose, 200 µg/ml of leucine, 200 µg/ml of proline, 2.0 µg/ml of thiamine-HCl, and 200 µg/ml of ampicillin. The mixture was cultured at 30° C. for about 16 hours to collect the cells.

To the collected cells were added 0.3 ml of a 0.5M EDTA solution, and 30 ml of a mixture of 20 mm Tris-HCl and 30 mM NaCl, to prepare a suspension. Further, 1 ml of a 4 mg/ml lysozyme solution was added thereto, the mixture was stirred and then allowed to stand at 0° C. for 1 hours. After this, the cell suspension was subjected to ultrasonic crushing, and the ultrasonically crushed cells were centrifuged (8000 rpm for 10 minutes) to prepare a supernatant. Also, a separate supernatant was prepared from centrifuging crushed cells of *E. coli* HB101/pBSF2-SD7, possessing a pBSF2-SD7 plasmid with no transglutaminase cDNA, transformed in the same manner as *E. coli* HB101/pIL6TG1 (AJ12730).

The transglutaminase activity of each of the supernatants was determined according to an activity detection method which measures the change in fluorescence intensity (fluorescence intensity at 480 nm, resulting from excitation irradiation with 350 nm wavelength light) due to bonding of monodansyl cadaverine with dimethylated casein. This activity detection method is based on the method described in *Nippon Suisan Gakkaishi* (1991), Vol. 57, pp. 1203–1210, with a few modifications. That is, 150 µl of each of the test samples was added to a solution (adjusted to 2.5 ml after addition of the samples) composed of 1 mg/ml of dimethylated casein, 15 µM of monodansyl cadaverine, 5 mM of CaCl$_2$, 50 mM of Tris-HCl (pH 7.5) and 3 mM of dithiothreitol (DTT), which was stirred and kept at 37° C. for 30 minutes. After the reaction, EDTA solution was added to a final concentration of 10 mM, and the fluorescence intensity of each of the reaction solutions was measured using a fluorescence intensity meter (available from Shimazu RF-520).

The results, which can be seen in Table 1, clearly show that transglutaminase activity was present in the cell extract of *E. coli* which possesses an expression plasmid having transglutaminase cDNA, obtained in the example described above. It became obvious from this result that the cDNA we acquired coded for transglutaminase.

TABLE 1

| Strain | TG cDNA | Relative fluorescence intensity |
|---|---|---|
| pBSF2-SD7/HB101 | absent | 9 |
| pIL6TG1/HB101 | present | 257 |

Note:
TG cDNA = transglutaminase cDNA

4. Construction of plasmid pTTG2-22, which expresses the *Pagrus major* transglutaminase gene, its introduction into *E. coli* and the verification of physiological activity of the TGase produced by the transformant Next, in order to further produce a large amount of transglutaminase, we made an improvement in the transglutaminase expression plasmid. An explanation thereof is given below.

Since the amount of transglutaminase expressed by transglutaminase expression plasmid pIL6TG1 obtained in Example 3 was small, further diligent research was conducted in order to construct a plasmid capable of expressing more transglutaminase than pIL6TG1, and a modification was made to increase the translation efficiency of the transglutaminase gene in *E. coli*.

The modification involved substituting a portion of the DNA base sequence of the natural transglutaminase gene with chemically synthesized DNA to alter the base sequence without changing the coded amino acid sequence, and designing it so that the transglutaminase gene might yield a more efficient expression in *E. coli*.

As shown in FIG. 4, chemically synthesized DNA fragments (SEQ ID NOS:12–19) were designed and prepared, which included a consensus SD (Shine-Dalgarno) sequence (5'-TAAGGAGGT-3') and a region coding for the section of the transglutaminase of SEQ ID NO:6 from the aminoterminal methionine to the 32nd amino acid (leucine), downstream therefrom, with the intention of incorporating them into the natural transglutaminase gene, according to the procedure described below. Codons preferred in *E. coli* and/or codons containing AT rich sequences were selected for the region coding for the section of transglutaminase from the amino-terminal methionine to $^{32}$Leu.

Figure 5:
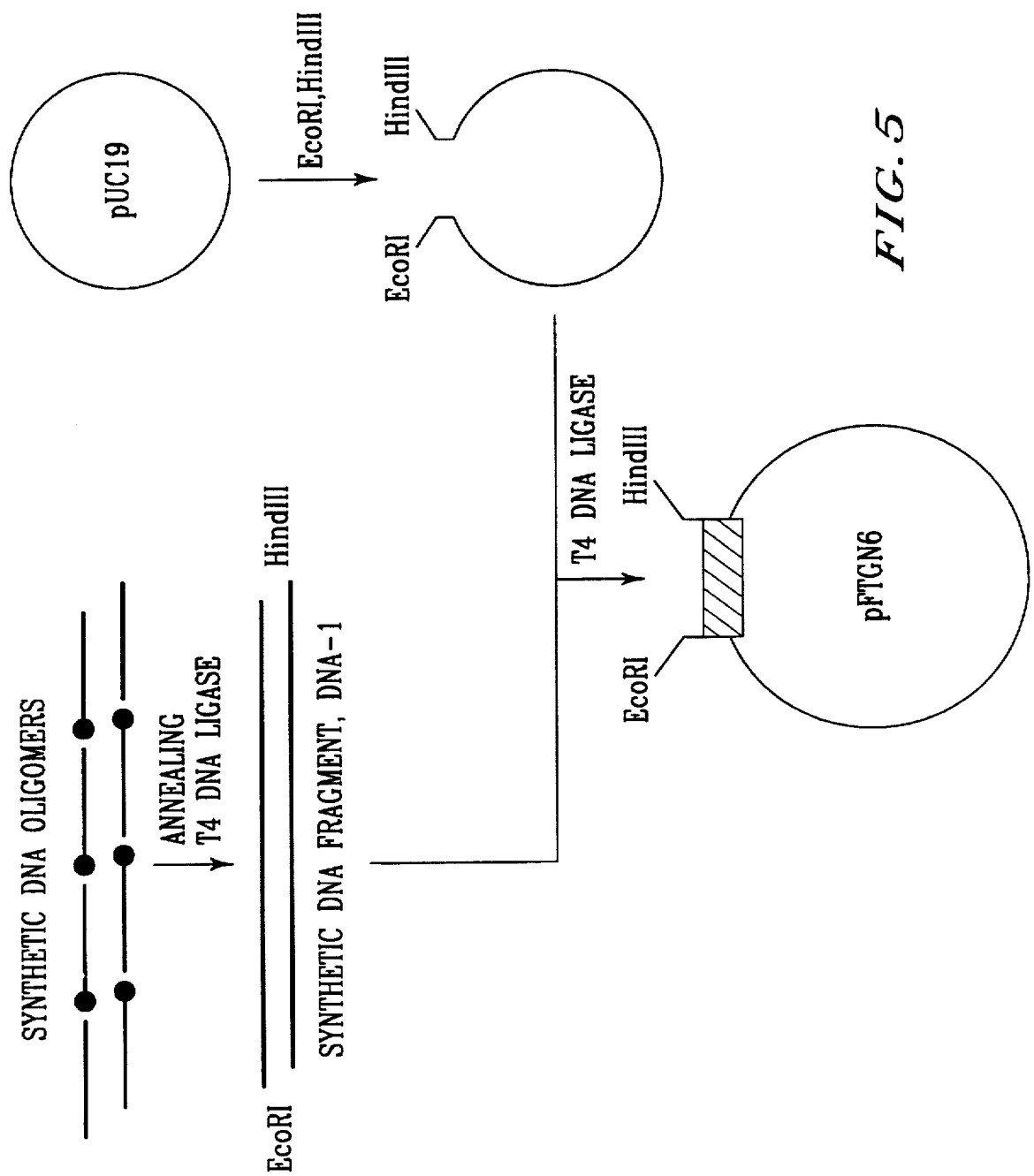
FIG. 5 shows a process for the construction of plasmid pFTGN6, used for the later construction of plasmid pTTG2-22, used in turn for the expression of *Pagrus major* transglutaminase.

Eight DNA oligomers (SEQ ID NOS:12–19) for construction of the chemically synthesized DNA fragment named DNA-1 (SEQ ID NO:1) were synthesized with a DNA synthesizer (manufactured by A.B.I.). These oligomers were combined and linked using a conventional method, annealing and ligating with T4 DNA ligase, to prepare the chemically synthesized DNA-1. Next, pUC19 was digested with the restriction enzymes EcoRI and HindIII, and the DNA fragments were cloned therein to construct pFTGN6 (see FIG. 5). This plasmid was also used for verification of the DNA base sequence, confirming that the prepared DNA had the intended sequence.

Figure 6:
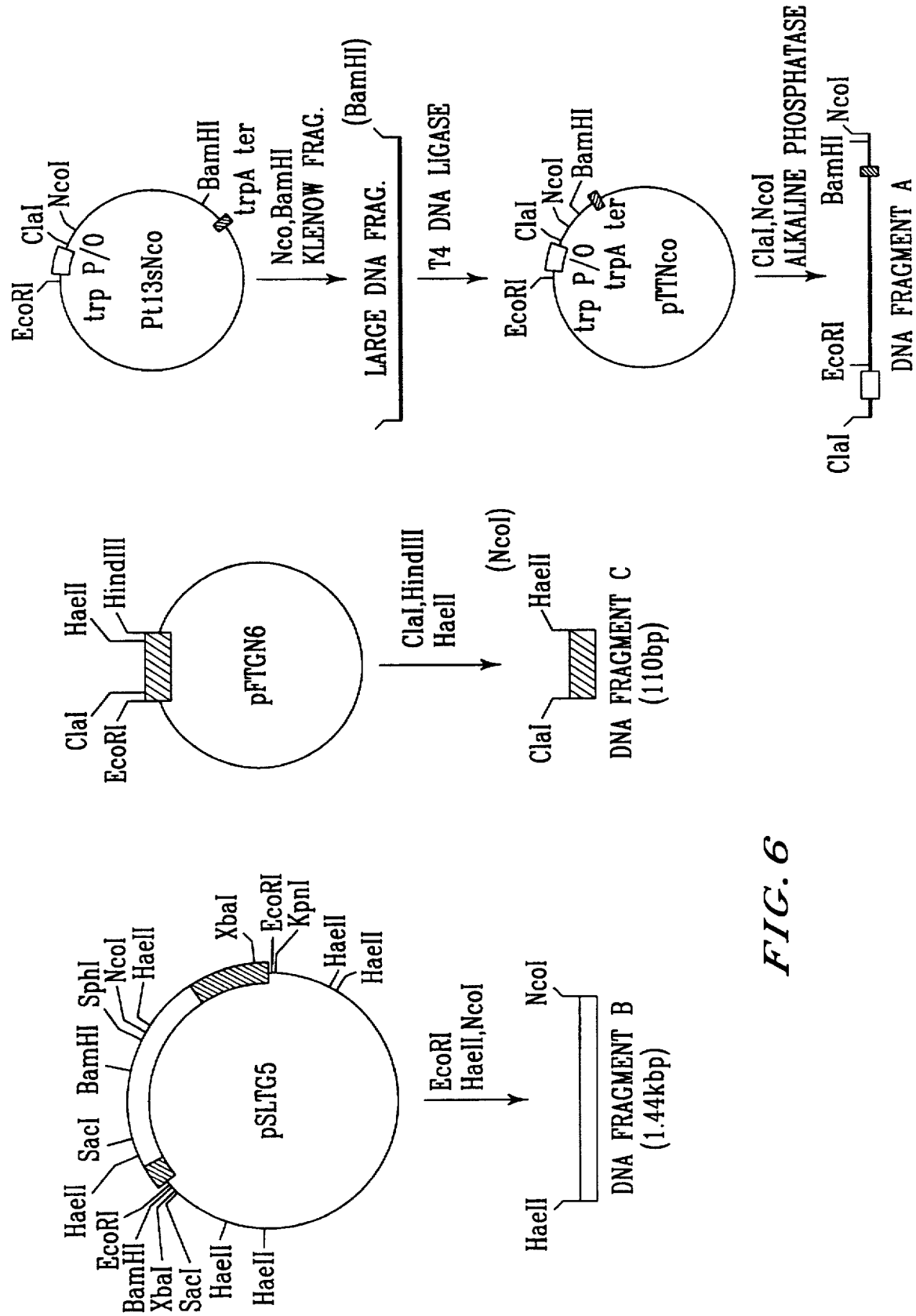
FIG. 6 shows a process for the acquisition of DNA fragments A, B and C, used in the construction of plasmid pTTG2-22, later used for the expression of *Pagrus major* transglutaminase.

Plasmid pFTGN6 was digested with the restriction enzymes ClaI and HindIII, and was further treated with restriction enzyme HaeII, to yield DNA fragment C (approximately 110 base pairs) having ClaI and HaeII cleavage termini (see FIG. 6).

In a separate procedure, plasmid pSLTG5, which includes cDNA coding for *Pagrus major* transglutaminase, was treated with EcoRI, HaeII and NcoI to obtain a DNA fragment (DNA fragment B) of approximately 1.44 kbp (kilobase pairs), which contained the major part of transglutaminase cDNA (see FIG. 6).

Expression vector pT13sNco (listed in *J. Biochem.*, 104, 30–34, 1988), possessing a tryptophan promoter and trpA terminator, was digested with NcoI and BamHI, and both of the cleavage termini were made flat with Klenow enzyme, thus acquiring a large DNA fragment. This was further self-ligated with T4 DNA ligase to obtain the plasmid pTTNco. Next, pTTNco was digested with ClaI and NcoI, after which the cleavage termini were dephosphorylated with alkaline phosphatase, to prepare a large DNA fragment (DNA fragment A) possessing a tryptophan promoter and a trpA terminator (see FIG. 6).

Figure 7:
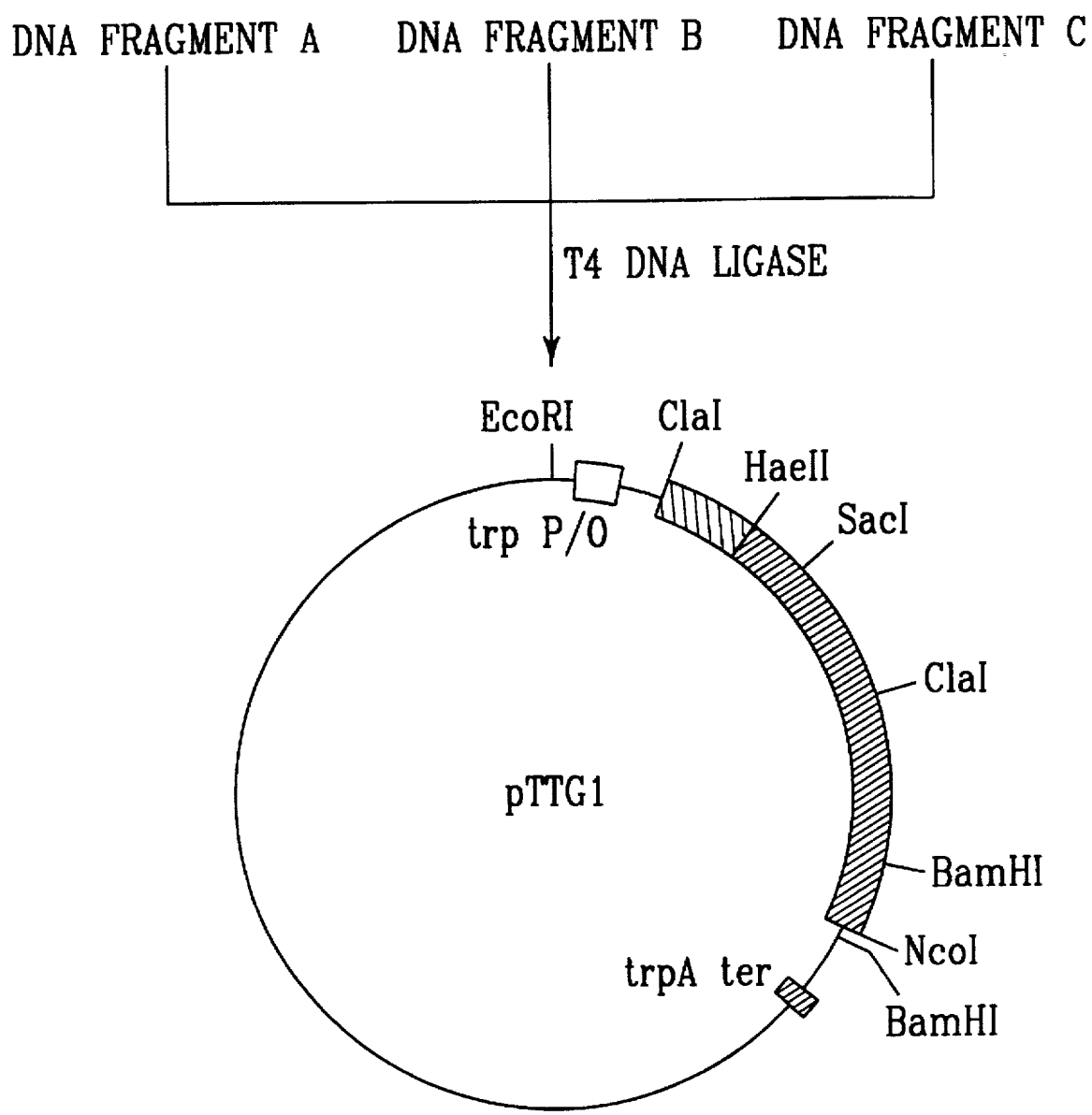
FIG. 7 shows a process for the construction of plasmid pTTG1.

Each of the DNA fragments A, B and C was ligated with T4 DNA ligase, to construct plasmid pTTG1 (see FIG. 7). For greater clarity, DNA fragment B, represented by an outlined bar in FIG. 6, is represented by a solid bar in FIGS. 7 and 8.

Figure 8:
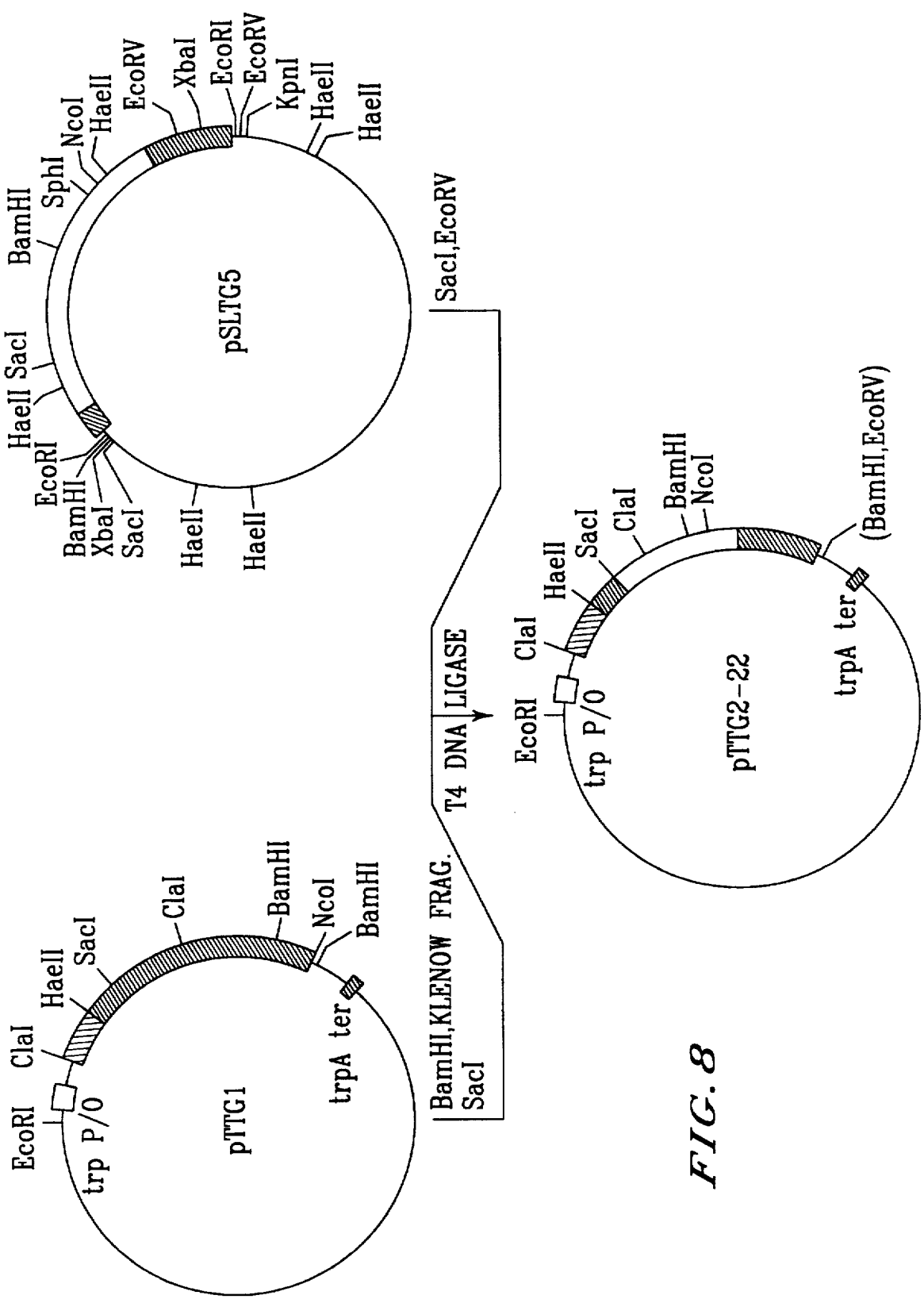
FIG. 8 shows a process for the construction of expression plasmid pTTG2-22, used for the expression of *Pagrus major* transglutaminase.
Figure 9:
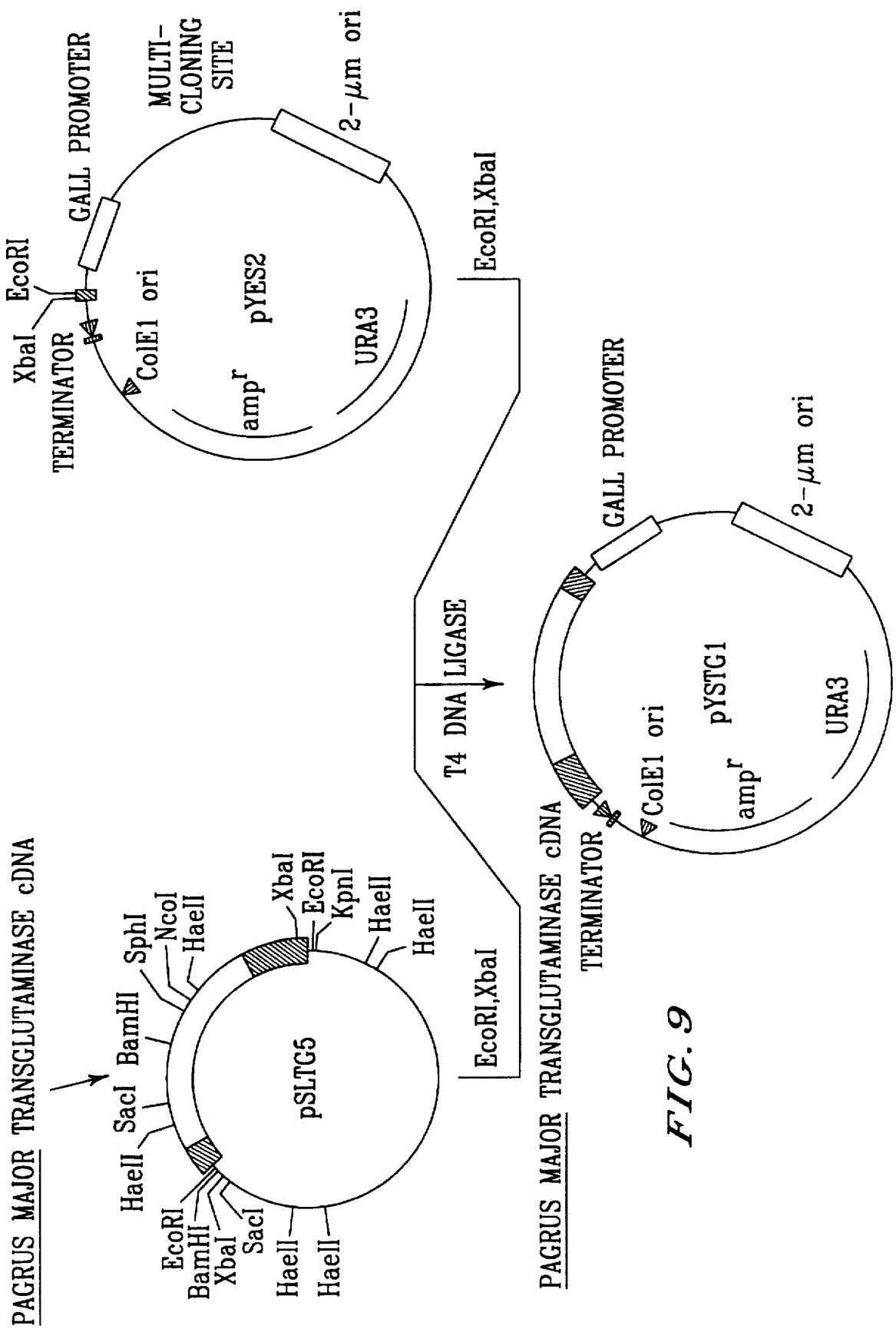
FIG. 9 shows a process for the construction of plasmid pYSTG1, used for the expression of *Pagrus major* transglutaminase cDNA in yeast.

Next, the constructed plasmid pTTG1 was treated with BamHI, the cleaved termini were made flat with Klenow enzyme, then it was digested with SacI to obtain the large DNA fragment shown in FIG. 8. Separately, pSLTG5 was treated with the restriction enzymes SacI and EcoRV to prepare a small DNA fragment. These DNA fragments were ligated with T4 DNA ligase, to construct expression plasmid pTTG2-22 (see FIG. 8). Expression plasmid pTTG2-22 was then introduced into *E. coli* HB101 using a conventional method to prepare a transformant, *Escherichia coli* HB101/pTTG2-22 (AJ12742). AJ12742 is deposited with the Fermentation Research Institute, Agency of Industrial Science and Technology (1-3, Higashi, 1-chome, Tsukuba-shi, Ibaraki-ken 305, Japan) under the deposit number FERM BP-4117.

A colony of the acquired transformant was applied onto an agar plate containing 200 μg/ml of ampicillin, and cultured at 30° C. overnight, after which approximately 2 cm$^2$ of the lawn of growing cells from the plate were inoculated into a Sakaguchi flask containing 100 ml of an M9 casamino acid culture medium supplemented with 2% glucose, 200 μg/ml of leucine, 200 μg/ml of proline, 2.0 μg/ml of thiamine-HCl, and 200 μg/ml of ampicillin. The mixture was cultured at 30° C. for about 16 hours to collect the cells.

A supernatant from crushed cells was prepared from the collected cells in the same manner as in Example 3. Also, another supernatant was prepared by centrifugation of crushed *E. coli* cells possessing a plasmid without transglutaminase cDNA (*E. coli* HB101/pTTNco) in the same manner.

The transglutaminase activity of each of the supernatants (50 μl) was verified in the same manner as in Example 3, according to an activity detection method which measures the change in fluorescence intensity (fluorescence intensity at 480 nm, excited with 350 nm wavelength light) due to bonding of monodansyl cadaverine with dimethylated casein. The results in Table 2 clearly show that transglutaminase activity was present in the cell extract of *E. coli* which possesses an expression plasmid (pTTG2-22) having transglutaminase cDNA, obtained in the example described above. This result showed that the cDNA we acquired codes for transglutaminase.

TABLE 2

| Strain | TG cDNA | Relative fluorescence intensity |
|---|---|---|
| pTTNco/HB101 | absent | 21 |
| pTTG2-22/HB101 | present | 910 |

Note:
TG cDNA = transglutaminase cDNA

Next, it was verified whether or not the above-mentioned cell extract solution could gelatinize the myosin B solution derived from Alaska pollack (*Theragra chalcogramma*). 1.0 ml of an Alaska pollack-derived myosin B solution (approx. 6 mg/ml) was used as the substrate, and four samples were prepared in which the following components were added:

(1) 470 μl of 50 mM CaCl$_2$ and 100 μl of *E. coli* raw extract solution exhibiting transglutaminase activity was detected;

(2) 470 μl of 50 mM CaCl$_2$;

(3) 100 μl of *E. coli* raw extract solution exhibiting transglutaminase activity; and (4) nothing.

Each of the samples were prepared in a test tube, and the mixtures were stirred and allowed to stand at room temperature for about 16 hours. The gelation of myosin B was judged by inverting the test tube and observing whether the reaction contents dripped (were able to flow at ambient temperature) or were solidified (hardened). The results, shown in Table 3 below, indicated gelation only in the sample containing both calcium chloride and the *E. coli* extract which exhibited transglutaminase activity, proving that the cDNA acquired according to the present invention contained a DNA fragment which codes for transglutaminase.

TABLE 3

|  | TG added | | TG not added | |
| --- | --- | --- | --- | --- |
|  | Ca present | Ca absent | Ca present | Ca absent |
| Gelation of myosin B | + | − | − | − |

Note:
TG: cell extract exhibiting transglutaminase activity
Ca: calcium chloride
+: gelatinized
−: not gelatinized 5. Construction of plasmid pYSTG1, which expresses the *Pagrus major* transglutaminase gene, its introduction into *S. cerevisiae*, and the verification of physiological TGase activity produced by the transformant Plasmid pSLTG5, containing cDNA which codes for *Pagrus major* transglutaminase, was treated with the restriction enzymes EcoRI and XbaI to obtain a DNA fragment of approximately 2.5 kbp (kilobase pairs) having transglutaminase cDNA.

In a separate procedure, pYES2 (available from Invitrogen Co.), which uses a GAL1 promoter (GAL1 represents a gene which codes for galactokinase) for the expression of foreign genes, was used as an expression vector for *S. cerevisiae*. pYES2 was treated with the same restriction enzymes EcoRI and XbaI, to prepare a DNA fragment of approximately 5.8 kbp.

The two above-mentioned DNA fragments were ligated with T4 DNA ligase according to a conventional method, and the product was introduced into a competent *E. coli* HB101 cell (available from Takara Shuzo Co.) according to a conventional method. Selection of the transformant was done using an L-agar plate containing the antibiotic ampicillin at a concentration of 100 µg/ml. Next, six individual strains were picked up from the cultured *E. coli* colonies using a sterilized toothpick, and each was transferred to a separate 3 ml L-culture medium containing 100 µg/ml of ampicillin. Each sample was shake-cultured at 30° C. for 16 hours.

Plasmid DNA was prepared from 2 ml of each of the cultures using the alkaline SDS method, and the pattern of restriction enzyme cleavage was analyzed by agarose gel electrophoresis. The analysis indicated that plasmids obtained from four of the strains were the desired one, and the plasmid was named pYSTG1. Further, the DNA base sequence was analyzed for the junction regions at the time of construction of the plasmid, verifying that the base sequences were correct.

The pYSTG1, constructed as described above, was then introduced into a yeast, *Saccharomyces cerevisiae*, INVSC2 strain (MATα, his3-Δ200, ura3-167), according to a conventional yeast transformation method, further using a conventional alkaline cation method kit (manufactured by Bio101, purchased from Funakoshi, Inc.). A YNB culture medium (composition: 0.67% yeast nitrogen base without amino acids (available from Difco Co.), 2% glucose, 2% agar) containing 20 mg/l of histidine was used as the selection plate. In this manner a transformant, *Saccharomyces cerevisiae* INVSC2/pYSTG1 (AJ14679) was obtained.

AJ14679 is deposited with the Fermentation Research Institute, Agency of Industrial Science and Technology (1-3, Higashi, 1-chome, Tsukuba-shi, Ibaraki-ken 305, Japan) under the deposit number FERM BP-4085.

The transformant yeast, grown on the above-mentioned YNB culture medium plate containing 20 mg/l of histidine, was inoculated into 100 ml of a YPD culture medium (composition: 1% yeast extract, 2% bactopeptone, 2% glucose), and the mixture was cultured at 30° C. for a day and a night with shaking. The culture was then centrifuged to collect the cells, which were then washed with 1% yeast extract, after which they were suspended in 10 ml of the same solution. Next, 5 ml of the suspension was added to 95 ml of a culture medium composed of 1% yeast extract, 2% bactopeptone and 2% galactose, and this mixture was cultured at 30° C. for 18 hours with shaking. Recombinant yeast was cultured in a galactose-containing culture medium to induce transcription from GAL1 promoter. Also, the remaining 5 ml of the suspension mentioned above was inoculated in the same manner into 95 ml of a liquid YPD culture medium, and culturing was done under conditions which did not induce transcription from GAL1 promoter.

In a separate procedure, a host yeast INVSC2 strain not possessing the pYSTG1 plasmid was grown on a separate YPD culture plate, and inoculated in the same manner described above into 100 ml of a liquid YPD culture medium. The mixture was cultured at 30° C. The above-described procedures were then followed, and 5 ml of the obtained suspension was inoculated into 95 ml of the liquid YPD culture medium and cultured.

Preparation of the sample for measurement of transglutaminase activity was done in the following manner. Yeast, which had been cultured in 100 ml of a culture medium, were centrifuged to collect the cells, to which 15 ml of a 20 mM Tris-HCl buffer solution (pH 7.5) containing 30 mM sodium chloride were added to suspend the cells. To the suspension, 0.25 ml of 0.5M EDTA was added, the mixture was then stirred, after which an almost equal volume of glass beads (diameter=0.75 mm) were added to the suspension. The mixture was stirred vigorously for 4 minutes. After this, centrifugation was done at 6000 rpm for 10 minutes, the insolubles were removed, and the supernatant thereof was used as a sample for measurement of transglutaminase activity.

The transglutaminase activity of the supernatants (50 µl or 150 µl) from each of the disrupted cell solutions was verified in the same manner as in Example 3 described above, according to an activity detection method which measures the change in fluorescence intensity (fluorescence intensity at 480 nm in response to excitation with 350 nm wavelength light) due to bonding of monodansyl cadaverine with dimethylated casein (see Table 4). Here, the fluorescence intensity was treated as zero when the disrupted cell solution of yeast INVSC2 strain not containing the pYSTG1 plasmid was added to the solution for the activity measurement. This result clearly shows that transglutaminase activity was present in the disrupted cell extract solution of the yeast which possessed the expression plasmid pYSTG1, having transglutaminase cDNA as obtained in Example 1 described above, under the induced condition of transcription from the GAL1 promoter. Also, when EDTA was preadded to the enzyme reaction solution and calcium ion was removed, there was, as expected, no detection of transglutaminase activity. Based on this result, the cDNA which we acquired was that which codes for calcium ion-dependant transglutaminase.

20% formamide, 100 microgram/ml of herring testis DNA and 0.1% SDS. Also, the DNA probe used for the hybridization was the DNA fragment of about 300 bp of a cDNA of *Pagrus major* liver transglutaminase (SEQ ID NO:3), the

TABLE 4

| Assayed samples *1 | EDTA *2 | Transcription induction | Relative fluorescence intensity |
|---|---|---|---|
| Crushed cell solution 50 µl | absent | no | 65 |
| Crushed cell solution 50 µl | absent | yes | 260 |
| Crushed cell solution 150 µl | absent | no | 66 |
| Crushed cell solution 150 µl | absent | yes | 348 |
| Crushed cell solution 150 µl | added | no | 0 |
| Crushed cell solution 150 µl | added | yes | 0 |

*1 Crushed cell solution of yeast INVSC2 strain having expression plasmid pYSTG1
*2 Before addition of the crushed cell solution, EDTA was added to the transglutaminase activity measurement solution to a final concentration of 100 mM, or absent from the mixture 6. DNA fragment containing a gene which codes for transglutaminase of flounder Using polytron and a teflon homogenizer, 1.5 g of the liver from flounder was crushed in a solution (20 ml) of 4M guanidine thiocyanate and 1% beta-mercaptoethanol. After 0.5% sodium laurylsarcosinate was added to and dissolved in the resulting cell suspension, the obtained solution was passed through a 23-gauge hypodermic needle 8 times to fragment the chromosomal DNA. Next, the solution was centrifuged at 4° C., 1000 rpm for 20 minutes and the supernatant obtained. The complete RNA was further purified by a conventional method, through CsCl density gradient centrifugation of the supernatant (Sambrook et al., Molecular Cloning: a laboratory manual, Cold Spring Harbor Laboratory, Cold Spring Harbor Press (1988)). The amount of the complete RNA obtained was 4.7 mg. Of this, 1.6 mg was subjected to an mRNA purifying kit (Clontech) using an oligo(dT)-cellulose column, and approximately 23 microgram of a purified mRNA molecule was obtained.

Of the obtained mRNA, 4.4 microgram was used as a template for cDNA synthesis. A random primer was used for cDNA synthesis, and a Time Saver cDNA synthesis kit (Pharmacia) was used to synthesize a double-stranded cDNA. The obtained cDNA was then inserted into a lambda-phage vector-lambdaZapII (Stratagene) at its restriction enzyme site EcoRI, after which a GIGAPACK II GOLD (Stratagene) packaging kit was used to prepare and acquire a cDNA library of flounder incorporated in the phage protein. The titer of this library was $2.0 \times 10^5$ pfu/microgram vector.

Host cells XLI-Blue were infected with $2.2 \times 10^5$ pfu of phage from said cDNA library of flounder, after which they were spread onto 11 agar plates of diameter 150 mm at $2 \times 10^4$ pfu per plate. The cells were cultured at 37° C. for about 6 hours, and then the phage plaques formed on the plates were transferred on a nylon membrane (Hibond-N, manufactured by Amersham). Next, the thus transcribed nylon membrane was treated with an alkali to denature the bound DNAs, neutralized and washed. Then, the membrane was treated at 80° C. for 2.5 hours to immobilize the DNA on the membrane.

Prehybridization of the obtained nylon membrane was then effected at 42° C. for 2 hours, followed by hybridization at 42° C. for 16 hours. The composition of the prehybridization solution was 6 x SSC (composition of 1 x SSC: 0.15M NaCl, 0.015M sodium citrate, pH 7.0), 5 x Denhardt's solution (composition of 1 x Denhardt's solution: 0.02% BSA, 0.02% Ficoll, 0.02% polyvinyl pyrrolidone), DNA fragment being able to code for the region containing the amino acid residues near to the active center and being able to be cleaved with restriction enzymes ClaI and BamHI and having been random-labeled with [alpha-32P] dCTP. The candidate strains for the positive clones obtained by this screening were further subjected to second and third screening to finally obtain 10 positive clones.

The infected cells maintaining the above mentioned 10 positive clones were then infected with helper phage (R408) to transform the cDNA derived from each of the positive clones into a form incorporated into phagemid vector pBluescriptSK(-). The length of the inserted cDNA of each of the 5 clones (named pFLTG10, 12, 16, 17, 21, respectively) of these clones was measured, from which the restriction enzyme cleavage map was constructed and the cDNA base sequences at the 5' end and the 3' end were sequenced. For the base sequencing, a fluorescent primer cycle sequencing kit was used (A.B.I.). As a result, the pFLTG21 was found to be a cDNA fragment of coding for the center part of a transglutaminase gene.

Next, for the purpose of obtaining a clone capable of coding for the C-terminal region of transglutaminase, which are not in the preceding 5 clones, the above-mentioned flounder cDNA library was again screened in the manner as mentioned below.

As a DNA probe for the screening, used were a DNA fragment of about 300 bp capable of being cleaved out from clone pFLTG21 with restriction enzyme EcoRI and a DNA fragment of about 500 bp capable of being cleaved out from clone pFLTG17 with restriction enzymes SalI and PstI, both fragments being random-labeled with [alpha-32P] dCTP. The other conditions were same as those mentioned above. As a result, a positive clone was obtained by the present screening, and finally 10 positive clones were obtained after second and third screenings.

Of the preceding 10 positive clones, the vector of each of 4 cDNA clones was converted into pBluescript SK-, and the relationship between the inserted cDNA's was analyzed. The four clones were named pFLTG44, 51, 55 and 63, respectively.

Further, for obtaining a clone capable of coding for the N terminal region of transglutaminase, a flounder cDNA library was newly prepared, using a synthesized DNA primer as formed on the basis of the base sequence of the inserted cDNA 5' end of pFLTG12 (the primer was composed of 19 bases, having a sequence of 5'-ACACTGCCG-GTCCATCGAA-3'; SEQ ID N0:29). As a template for synthesis of the cDNA, used was 2 microgram of the mRNA sample described above. The titer of the library obtained here was 1.5×10⁴ pfu/microgram vector.

Next, host *E. coli* cells XL1-Blue were infected with 6×10³ pfu of phage from said cDNA library, and then the screening was carried out by the method mentioned above. As the probe for the hybridization, used were a DNA fragment of about 300 bp capable of being cleaved from the preceding clone pFLTG21 with restriction enzyme EcoRI, and a DNA fragment of about 500 bp capable of being cleaved from pFLTG17 with restriction enzymes SalI and PstI, both fragments being random-labeled with [alpha-32P] dCTP. The candidate strains for the positive clones obtained by this screening were further subjected to second and third screening to finally obtain one positive cDNA clone.

The clone was converted into pBluescript SK- by the method mentioned above, and the clone was named pFLTG60. Next, the length of the inserted cDNA of the clone was measured, the restriction enzyme map was constructed, and the cDNA base sequences of the 5' end and 3' end regions were sequenced.

Figure 11:
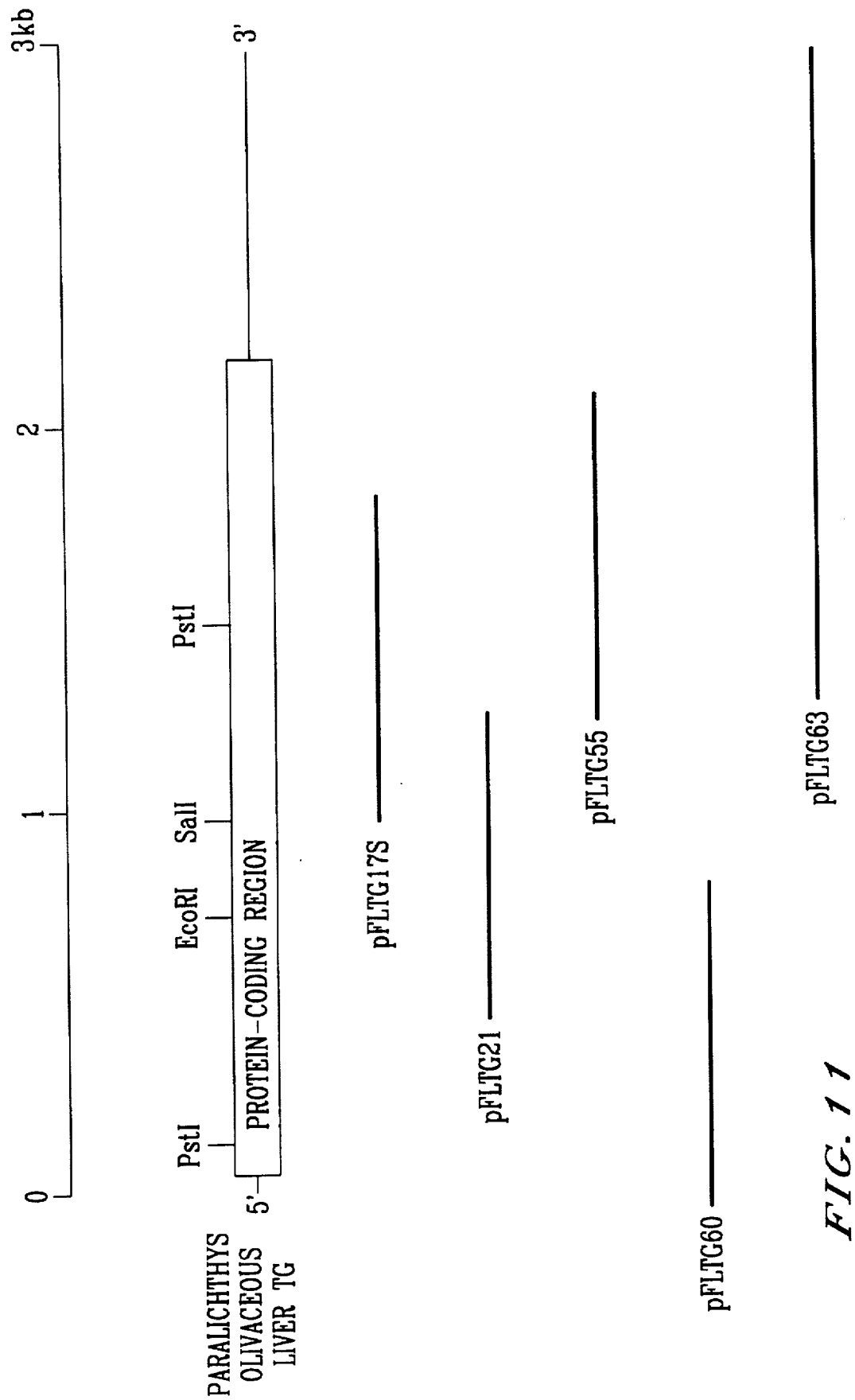
FIG. 11 shows the restriction enzyme cutting sites in a cDNA clone derived from *Paralichthys olivaceus* liver.
Figure 12A:
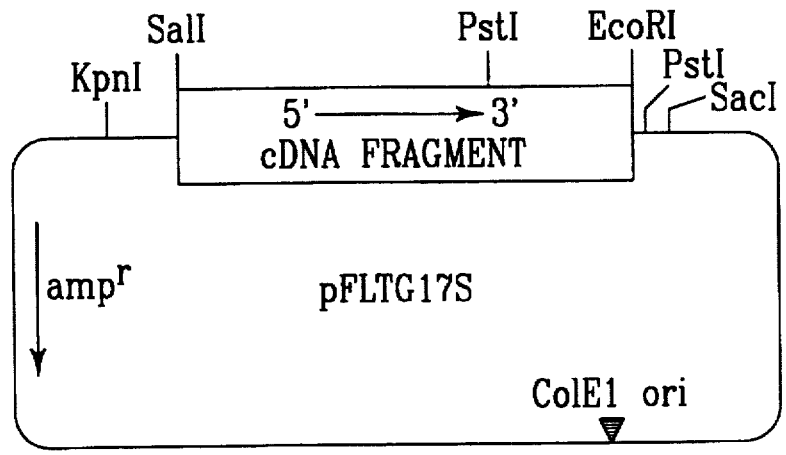
FIG. 12 shows a plasmid carrying a cDNA fragment coding for transglutaminase derived from *Paralichthys olivaceus*.
Figure 12B:
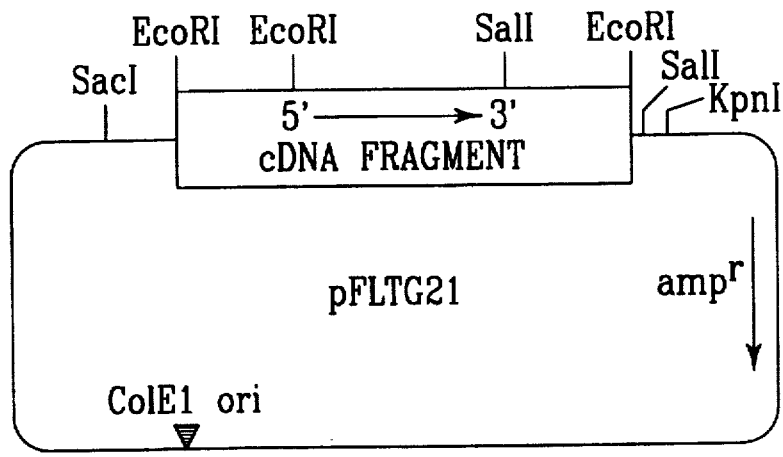
Figure 12C:
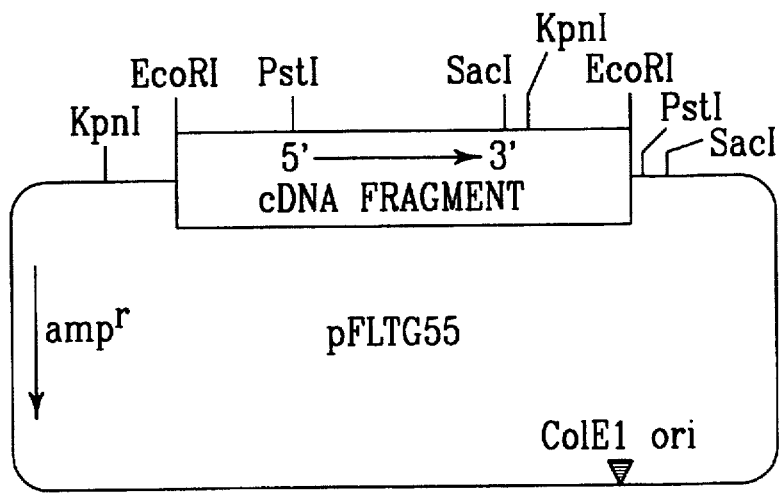
Figure 12D:
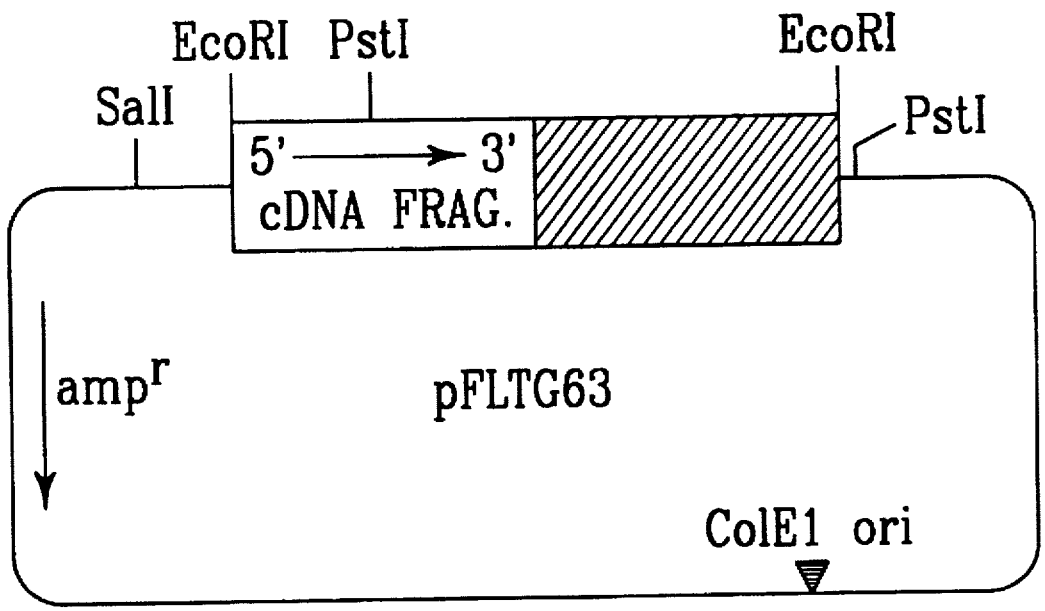
Figure 12E:
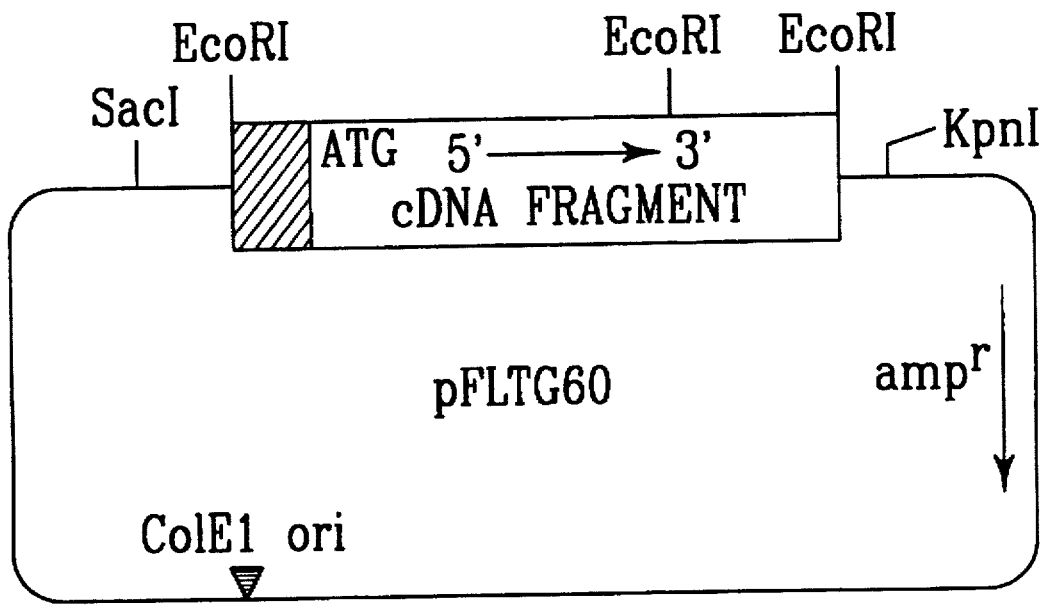

Of the thus obtained and sequenced 10 cDNA clones, the base sequence from the restriction enzyme SalI site to the 3' end of the inserted cDNA in pFLTG17, and the base sequence of the inserted cDNA fragment in each of pFLTG21, 55, 60 and 63 were sequenced. As a result, the DNA sequences of SEQ ID NO:30 and SEQ ID NO:32 in the Sequence Listing were clarified. The difference between the two base sequences resides in the difference in the 1854th base. But the change of the base does not change the translated amino acid residue. The amino acid sequences to be translated from the base sequences are shown as SEQ ID NOS:31 and 33. In addition, the relationship between the clones is shown in FIG. 11.

An *E. coli* strain (AJ 12798) of *E. coli* XLI-Blue/ pFLTG21 having plasmid pFLTG21 containing a part of the flounder-derived transglutaminase cDNA fragment (SEQ ID NO:30) obtained in the manner as above has been deposited in Fermentation Research Institute of Japan as FRI Deposition No. 4154 (FERM BP-4154); an *E. coli* strain (AJ 12799) of *E. coli* XLI-Blue/pFLTG55 having plasmid pFLTG55 as FRI Deposition No. 4155 (FERM BP-4155); an *E. coli* strain (AJ 12800) of *E. coli* XLI-Blue/pFLTG60 having plasmid pFLTG60 as FRI Deposition No. 4156 (FERM BP-4156); an *E. coli* strain (AJ 12801) of *E. coli* XLI-Blue/pFLTG63 having plasmid pFLTG63 as FRI Deposition No. 4157 (FERM BP-4157); and an *E. coli* strain (AJ 12797) of *E. coli* XLI-Blue/pFLTG17S having plasmid pFLTG17S having a cDNA clone fragment of the downstream region from restriction enzyme SalI of the cDNA fragment of plasmid pFLTG17 as FRI Deposition No. 4153 (FERM BP-4153). Each plasmid having cDNA fragment coding for transglutaminase derived from *Paralichthys olivaceus* are shown in FIG. 12.

The respective cDNA fragments thus obtained in the manner as mentioned above may easily be converted into one DNA fragment completely containing the coding region of transglutaminase by a known method. Plasmid pFLTG17S was digested with Pst I to prepare a large fragment containing cDNA segment. Similarly, pFLTG63 was digested with Pst I to prepare a DNA fragment coding for the C-terminal region of the transglutaminase. Both DNA fragments as mentioned above were ligated with T4 DNA ligase to construct pFLTG1-C in which the reading frame of the C-terminal region of transglutaminase was made to be conjugative.

On the other hand, pFLTG21 was digested with Bgl II and Pst I to prepare a large fragment. Similarly, pFLTG60 was treated with Bgl II and Pst I to prepare a DNA fragment coding for the N-terminal region of the transglutaminase. Both DNA fragments as mentioned above were ligated with T4 DNA ligase to construct pFLTG1-N in which the reading frame of the N-terminal region of the transglutaminase was made to be conjugative.

After pFLTG1-N was digested with EcoR I, the vector DNA of which both ends were dephosphorylated was ligated to the cDNA fragment derived from pFLTG1-N, and then pFLTG2-N in which cDNA fragment was inserted into the vector in the opposite direction in contrast with the direction of cDNA fragment in pFLTG1-N. Then, pFLTG2-N was digested with Sal I to prepare cDNA fragment coding for the N-terminal region of the transglutaminase. The cDNA fragment was incorporated into the restriction site Sal I in pFLTG1-C digested with Sal I to construct one cDNA fragment completely containing the coding region of the transglutaminase in the vector DNA.

On the other hand, transformation of *E. coli* strain recBC, sbcA with a single-stranded plasmid DNA having two cDNA fragments each having a duplicated cDNA region (for example, cDNA fragments on the respective plasmids of pFLTG60 and pFLTG21; pFLTG21 and pFLTG17; pFLTG17 and pFLTG63) at both ends brings about extremely easily recombination at the duplicated region in these cDNA fragments due to the recombination mechanism in the host *E. coli* strain, resulting in construction of a successively continued cDNA fragment. Repeating the process, the intended cDNA of a complete length is obtained. Utilizing the recombination mechanism of the kind, various chimera genes are constructed (Ogawa et al, Journal of Molecular Biology, vol. 226, pp. 651–660 (1992)).

The translated amino acid sequence of each transglutaminase cDNA derived from *Pagrus major, Theragra chalogramma,* and *Paralichthys olivaceus* was also investigated. As a result, some consensus amino acid sequences were found among the amino acid sequences of transglutaminase derived from fish. These consensus amino acid sequences are shown as SEQ ID NOS:34, 35, 36, 37, 38, 39, 40, 41, 42, 43, 44 and 45. Xaa indicates a nonspecific amino acid residue.

7. Investigation as to whether or not many other fishes of different kinds would have a gene homologous to the obtained *Pagrus major* transglutaminase cDNA We investigated as to whether or not a gene which is extremely highly homologous to the *Pagrus major*-derived transglutaminase gene as obtained by us in the previous example would exist in any other fishes of different kinds.

As test samples, used were the livers of horse mackerel, young yellowtail, sardine, Pacific saury, mackerel, bonito and salmon and the ovary of globefish; and as a negative control sample, used was the chromosome of *Bacillus subtilis*. About 3 g of the tissues of the respective fishes were cut into fine pieces, and 30 ml of an ice-cooled TN buffer (20 mM tris-HCl buffer (pH 7.5) containing 0.1M sodium chloride, as its composition) was added thereto and crushed with a teflon homogenizer.

The sample suspension was put in a centrifugal tube and subjected to centrifugation with a cooling centrifuger at 5° C. and at 1,500 rpm for 5 minutes to obtain a precipitated fraction. To this was added 5 ml of an ice-cooled TNE buffer (TN buffer containing 1 mM EDTA, as its composition) and well suspended. Then, 15 ml of the ice-cooled TNE buffer was further added thereto and mixed. Afterwards, 1 ml of 10% SDS was added thereto and shaken at room temperature for 30 minutes, then 100 microliter of 20 mg/ml Protease K solution was added thereto and reacted overnight at 50° C.

After the reaction, the aqueous solution of each sample was subjected to phenol treatment, phenol-chloroform treatment and chloroform treatment for removal of proteins therefrom. Afterwards, 1/50 volume of 5M sodium chloride and 2.5 times volume of ethanol were added to each sample so as to precipitate the nucleic acid. This was recovered and finally dissolved in 1 ml of a TE buffer (10 mM tris-HCl buffer (pH 7.6) containing 1 mM EDTA, as its composition).

Next, about 10 microgram of the DNA of each sample was digested with 200 units of restriction enzyme HindIII and subjected to electrophoresis using 1% agarose gel. The gel was stained with ethidium bromide to ascertain that the amount of the migrated DNA of each sample was almost constant. Then, the gel was dipped in 0.25N hydrochloric acid and subsequently treated with a 0.4N sodium hydroxide solution containing 0.6M sodium chloride. Next, the gel was neutralized with a 0.5M tris-HCl buffer (pH 7.5) containing 1.5M sodium chloride, and the nucleic acid in the gel was transcribed to a nylon membrane (Gene Screen Plus) with 10 x SCC (composition: 1.5M sodium chloride, 0.15M trisodium citrate).

The membrane with the nucleic acid as adsorbed thereto was treated with 0.4N sodium hydroxide containing 0.6M sodium chloride, then with a 0.5M tris-HCl buffer (pH 7.5) containing 1.5M sodium chloride, and thereafter dipped in a 2 x SCC solution. Afterwards, the membrane was left at room temperature for 30 minutes and then dried at 80° C. for 2 hours.

The thus obtained nylon membrane was subjected to prehybridization at 65° C. for 3 hours and then to hybridization at 60° C. for 16 hours. The composition of the prehybridization solution was 5 x SSC (composition of 1 x SCC: 0.15M NaCl, 0.015M sodium citrate, pH 7.0), 1 x Denhardt's solution (composition of 1 x Denhardt's solution: 0.02% BSA, 0.02% Ficoll, 0.02% polyvinyl pyrrolidone) and 0.1% SDS. The composition of the hybridization solution comprised 0.75M sodium chloride, 20 mM tris-HCl (pH 8.0), 0.25 mM EDTA, 1% SDS, 1 x Denhardt's solution and 50 microgram/ml of $E.\ coli$ genome solution. The DNA probe as prepared in the manner mentioned below was used in the form of having a concentration of $2\times10^5$ cpm/ml.

As the DNA probe, used was a DNA fragment as radio isotope-labeled with a random primer, using guinea pig transglutaminase cDNA fragment and the *Pagrus major* transglutaminase cDNA fragment as obtained by us each as a template. As the guinea pig transglutaminase cDNA fragment, used was one in which the plasmid pKTG1 (Ikura et al, Eur. J. Biochem., Vol. 187, pp. 705–711, (1990)) had been treated with restriction enzyme StuI. For the *Pagrus major* transglutaminase cDNA, the obtained cDNA clone pSLTG5 was cleaved with restriction enzymes ApaI and SacI, and the resulting transglutaminase cDNA fragment was used as a template.

The membrane which had been subjected to the hybridization mentioned above was washed with 0.1 x SCC and 0.1% SDS solution at 60° C., dried and then subjected to autoradiography. As a result, it was found that the guinea pig-derived DNA probe did not hybridize to the nucleic acid of all the test samples under the condition of this experiment; while the *Pagrus major*-derived DNA probe did not hybridize to the chromosomal DNA of *B. subtilis* at all but strongly hybridized to the nucleic acids derived from horse mackerel, bonito, mackerel, young yellowtail and globefish and to, though weakly, those derived from sardine, Pacific saury and salmon.

From the above-mentioned facts, the existence of a gene having a high homology to the transglutaminase gene as obtained by us in other fishes of different kinds was verified for the first time; and it was also verified for the first time that a transglutaminase gene may also be obtained with extreme ease even from other fishes of different kinds than *Pagrus major*, Alaska pollack, *Theragra chalogramma*, and flounder, *Paralichthys olivaceus*, by the use of the transglutaminase as obtained by us as a DNA probe.

8. Analysis of partial amino acid sequence of Alaska pollack liver transglutaminase In order to show the fact that the Alaska pollack-derived transglutaminase gene as obtained in the manner mentioned above is one to actually express a transglutaminase enzyme in an Alaska pollack, the natural enzyme was purified and the structure thereof was clarified. The transglutaminase activity of the enzyme was verified according to an activity detection method which measures the change in fluorescence intensity due to bonding of monodansylcadaverine with dimethylated casein as an index, in accordance with the activity detecting method mentioned above.

30 ml of a 20 mM tris-HCl buffer (pH 8.3) containing 10 mM NaCl, 5 mM EDTA and 2 mM dithiothreitol was added to 15 g of Alaska pollack liver and crushed with a homogenizer. The thus-obtained suspension was centrifuged at 4° C., 3,000 rpm for 10 minutes (Hitachi's Himac CR 20B2, with rotor RPR20-2). Then, the supernatant was further centrifuged at 4° C. at 37,000 rpm for one hour (Hitachi's 70P-72, with rotor RP-70T). The supernatant was filtered through a 0.45 micrometer-filter (GL Science's GL Chromatodisc) to obtain 24 ml of a crude extract.

The protein concentration of the extract was measured with a BioRad's protein assay kit to be about 8.6 mg/ml. Using 5 microliter of the crude extract, the transglutaminase activity thereof was determined to have a total activity of 849 units. Thus, the relative activity of it was 4.10 units/mg protein.

Next, the crude extract was passed through a Q-Sepharose column (Pharmacia; diameter 1.6 cm×10 cm) as equilibrated with the same buffer, whereupon the ion exchanger of the column adsorbed the transglutaminase. Then, NaCl concentration gradient elution of the column was effected to give a fraction having a transglutaminase activity at the NaCl concentration of about 100 mM. The thus obtained transglutaminase-active fraction (10 ml) was subjected to dialysis to the same buffer overnight, again passed through the Q-Sepharose column and subjected to elution under the same condition to obtain 9.5 ml of a fraction having a transglutaminase-activity.

The protein concentration of the active fraction was about 0.73 mg/ml. The total transglutaminase activity of it was 249 units, and therefore the relative activity of it was 36.1 units/mg protein.

Next, the thus obtained active fraction was subjected to dialysis overnight to a sodium acetate solution (pH 6.45) containing 50 mm NaCl, 2 mM EDTA and 0.5 mM dithiothreitol and applied to through an S-Sepharose column (Pharmacia: diameter 1.6 cm×10 cm) as equilibrated with the same buffer, whereupon the column adsorbed the transglutaminase. Then, NaCl concentration gradient elution of the column was effected to give a fraction (6.0 ml) having a transglutaminase activity at the NaCl concentration of about 200 mM.

The protein concentration of the active fraction was about 56 microgram/ml. The total transglutaminase activity of it was 201 units, and therefore the relative activity of it was 591.2 units/mg protein.

In the fraction, only a protein showing a single band of a molecular weight of about 77,000 on SDS-PAGE exited, and thus an Alaska pollack-derived transglutaminase was purified and obtained. The relative activity of the purified fraction was 143 times as large as that of the crude extract; and the recovery yield of the former was 23.7%.

(a) Electrophoresis Assay 30 microliters of a purified transglutaminase solution was added with the same amount of a 0.125M tris-HCl buffer (pH 6.8) containing 10% mercaptoethanol, 4% SDS, 20% glycerin and 0.002% bromophenol blue, and heated in a boiling bath for one minute to prepare a sample for electrophoresis. 40 microliters of the sample was applied to a prepared 5 to 20% polyacrylamide gel (ATTO) and subjected to electrophoresis with a 0.025M tris-glycine buffer containing 0.1% SDS for about 2 hours at 40 mA. After completion of the process, the migrated sample was stained overnight with a 0.12% Coomassie brilliant blue solution containing 50% methanol and 7% acetic acid and then decolored with a 7% acetic acid solution containing 50% methanol. As a result, a single band was obtained at a molecular weight of about 77,000.

(b) Partial amino acid sequence of Alaska pollack liver-derived transglutaminase About 4 ml of the S-Sepharose fraction containing about 80 microgram of the purified transglutaminase was put in a dialytic tube and subjected to dialysis to a 5 mM tris-HCl buffer (pH 8.3) containing 0.001 mm EDTA for 6 hours, then again to dialysis to the same solution, whereby the alkali metal ions were removed from the transglutaminase product. This was dried by centrifugal concentration, 0.8 ml of distilled water was added thereto and stirred at 37° C. for 30 minutes so that the product was again dissolved in the water. To this was added 16 microgram of trypsin (by Sigma; 11,700 units/mg) and reacted at 37° C. for 12 hours, whereby this was fragmented into peptide fragments. The reaction was terminated by adding one drop of formic acid thereto.

Next, the reaction liquid was applied to a reverse phase HPLC (Inertsil Prep-ODS; diameter 6.0 mm×250 mm; by GL Science), using a solvent of 0.05% TFA (trifluoroacetic acid), whereupon the respective peptide fragments were separated and collected by acetonitrile concentration gradient elution.

The thus obtained peptide fragments were applied to a protein sequencer (MilliGen Biosearch; 6400/6600) to determine their amino acid sequences. The following sequences were obtained:

Xaa-Ala-Gly-Gly-Ser-Gly-Asp (SEQ ID NO:46);
Trp-Trp-Leu-His-Gln-Gln-Ser (SEQ ID NO:47);
Met-Tyr-Leu-Leu-Phe-Asn-Pro (SEQ ID NO:48);
Trp-Gln-Glu-Pro-Tyr-Thr-Gly-Gly (SEQ ID NO:49);
Phe-Asp-Val-Pro-Phe-Val-Phe-Ala-Glu-Val-Asn-Ala-Asp (SEQ ID NO:50); and
Ser-Xaa-Tyr-Ser-Asn-Glu (SEQ ID NO:51).

Xaa indicates an unidentified amino acid residue.

The above-mentioned six amino acid sequences completely correspond to a part of the amino acid sequences (SEQ ID NOS:8 and 10) presumed from the corresponding base sequence of the cDNA already obtained by us. The fact indicated that the cDNA obtained by us was just one which had been expressed in the body of Alaska pollack and which coded for the active transglutaminase.

9. Analysis of partial amino acid sequence of *Pagrus major* liver transglutaminace On the other hand, in order to show the fact that the *Pagrus major*-derived transglutaminase gene as obtained in the manner mentioned above is one to actually express a transglutaminase enzyme in a *Pagrus major*, the natural enzyme was purified and the structure thereof was clarified.

Like the case of the previous Alaska pollack-derived enzyme, the transglutaminase activity of the enzyme of the present case was verified according to an activity detection method which measures the change in fluorescence intensity due to bonding of monodansylcadaverine with dimethylated casein as an index, in accordance with the activity detecting method mentioned above.

46 ml of a 20 mM Tris-HCl buffer (pH 8.3) containing 10 mM NaCl, 5 mM EDTA and 2 mM dithiothreitol was added to 20 g of *Pagrus major* liver and crushed with a homogenizer. The thus obtained suspension was put in a centrifugal tube and applied to a centrifuge (Hitachi's 70P-72, with rotor RPRP-65T) at 4° C., 50,000 rpm for 45 minutes. Then, the supernatant part was passed through a 0.45 micrometer-filter (Advantic DISMIC-25 disposable syringe filter unit) so that insoluble high polymer substances were removed. As a result, 30 ml of an extremely red-colored extract was obtained. Next, almost the same amount (30 ml) of an ice-cooled 5 mM Tris-HCl buffer (pH 8.3) was added to the extract so that the ionic strength of the resulting solution was lowered. This was a crude extract of *Pagrus major* liver (60 ml).

The protein concentration of the extract was measured with a BioRad protein assay kit to be about 8.4 mg/ml. Using 5 micrometers of the crude extract, the transglutaminase activity thereof was determined to have a total activity of 2088 units. Thus, the relative activity of it was 4.14 units/mg protein.

Next, the crude extract was passed through a DEAE-Sephacel column (Pharmacia; diameter 2.6 cm×11 cm) as equilibrated with a 10 mM Tris-HCl buffer (pH 8.3) containing 5 mM NaCl, 2.5 mM EDTA and 0.5 mM dithiothreitol, whereupon the ion exchanger of the column was found to adsorb the transglutaminase. NaCl concentration gradient elution of the column was effected to give a fraction having a transglutaminase activity at the NaCl concentration of about 100 mM. The fraction was a DEAE fraction (about 59 ml).

The protein concentration of the active fraction was about 145 microgram/ml. The total transglutaminase activity of it was 1045 units, and therefore the relative activity of it was 122 units/mg protein.

The transglutaminase-active fraction thus fractionated with the DEAE-Sephacel resin was put in a dialytic tube and subjected to dialysis overnight to a 20 mM sodium acetate buffer (pH 6.25) containing 2 mM EDTA and 0.5 mM dithiothreitol. Next, the product was passed through a CM-Sepharose column (Pharmacia; diameter 1.6 cm×10 cm) as equilibrated with the same buffer, whereupon the column adsorbed the transglutaminase. Then, NaCl concentration gradient elution of the column was effected to give a transglutaminase-active fraction at the NaCl concentration of about 200 mM. The fraction (about 35 ml) was obtained to be a CM fraction.

The protein concentration of the active fraction was about 20 microgram/ml. The total transglutaminase activity of it was about 530.6 units, and therefore the relative activity of it was 758 units/mg protein.

The transglutaminase-active fraction thus fractionated with the CM-Sepharose resin was again put in a dialytic tube and subjected to dialysis overnight to a 20 mM sodium acetate buffer (pH 6.45) containing 50 mM NaCl, 2 mM EDTA and 0.5 mM dithiothreitol so that the salt concentration in the transglutaminase fraction liquid was lowered. This was passed through a heparin-Sepharose column (Pharmacia; Hi-Trap affinity column; bed-volume 1 ml) as equilibrated with the same buffer, whereupon the resin adsorbed the transglutaminase. NaCl concentration gradient elution of the column was effected, whereupon the transglutaminase was eluted from the heparin column at the NaCl concentration of about 200 mM. This was obtained (about 12.5 ml). This was a heparin fraction.

The protein concentration of the active fraction was about 32 microgram/ml. The total transglutaminase activity of it was about 290.5 units, and therefore the relative activity of it was 807 units/mg protein.

The present heparin fraction was subjected to SDS-polyacrylamide gel electrophoresis, and then the gel was stained with Coomassie brilliant blue, whereupon a single band as stained at only the position of a molecular weight of about 77,000 was identified. Thus, a *Pagrus major* liver-derived transglutaminase was purified and obtained. The relative activity of the thus obtained pure transglutaminase fraction was about 195 times as high as that of the crude extract and the recovery yield of the former was about 14%.

The partial amino acid sequence of the *Pagrus major* liver-derived transglutaminase was analyzed. About 4 ml of the heparin fraction containing about 100 micrograms of the purified transglutaminase was put in a dialytic tube and subjected to dialysis for 13 hours to a 20 mM Tris-HCl buffer (pH 8.3) containing 0.1 mM EDTA and 0.01 mM dithiothreitol, and then to a 20 mM Tris-HCl buffer (pH 8.3) containing 0.001 mM EDTA, whereby the alkali metal ions in the transglutaminase enzyme product were removed. To this was added 480 mg of urea, and the mixture was treated at 37° C. for 30 minutes. Then, 7.5 micrograms (0.02 unit amidase activity) of lysyl endo-peptidase (Wako Pure Chemicals) was added thereto and enzymatically treated therewith at 37° C. for 12 hours, so that the transglutaminase was fragmented to peptide fragments. After the treatment, 40 microliters of a 10% TFA (trifluoroacetic acid) solution was added to the reaction liquid and stirred, the final concentration of TFA being 0.1%.

Next, the reaction liquid was applied to a reversed phase HPLC (Vydac's C4 column; diameter 4.6 mm×250 mm), using a solvent of 0.1% TFA, for acetonitrile concentration gradient elution to separate the respective fragments, which were recovered.

The thus obtained peptide fragments were applied to a protein sequencer (Applied Biosystems; 470A) and the amino acid sequence of each of them was analyzed with a sequence analyzer (Applied Biosystems; 120A). The resulting sequences are identified as SEQ ID NOS:52–68 (See the accompanying Sequence Listing). Xaa indicates an unidentified amino acid residue.

These amino acid sequences are in the amino acid sequence (SEQ ID NOS:4 and 6) to be derived from the cDNA sequence obtained in the previous Example 1. The fact surely indicates that the cDNA as obtained herein codes for the enzyme showing the transglutaminase activity as functioning in a living body of a *pagrus major*.

10. Comparison of the enzymatic characteristics between guinea pig-derived transglutaminase and fish-derived transglutaminase The enzymatic characteristics of fish-derived transglutaminase (hereinafter referred to as FTG) were compared with those of guinea pig (marmot)-derived transglutaminase (hereinafter referred to as MTG), and the differences between them were investigated. In particular, the industrial superiority of FTG to MTG was investigated by the comparison.

(a) Relative activity

The enzymatic relative activity of the pure Alaska pollack transglutaminase as obtained in the previous example was compared with that of a commercial MTG by a fluorescent method. MTG samples used herein were one from Takara Shuzo and one from Sigma. Takara Shuzo's MTG had a purity of 95%; and Sigma's MTG had a similar purity.

The above-mentioned three transglutaminase products were prepared to have the same enzymatic concentration (as measured by Biorad's protein assay kit for the protein concentration), and the transglutaminase activity of each sample was measured at a pH value of 8.5 of being near to the respective optimum pH. As a result, it was found that the relative activity of FTG was 10 times as high as that of MTG (Takara Shuzo) and was 20 times as high as that of MTG (Sigma).

The above-mentioned three transglutaminase products each having a controlled concentration were developed with SDS-PAGE, stained with Coomassie Brilliant Blue and applied to a densitometer (LKB; Ultro Scan XL Laser Densitometer) to determine the quantity of the transglutaminase of each sample product. As a result, it was found that the transglutaminase quantity in FTG was about 4 times as high as those of the MTG'S. From the fact, it was found that the transglutaminase relative activity of FTG by a fluorescent method was 2.5 to 5 times as high as that of MTG.

As mentioned above, the relative activity of FTG is higher than that of MTG. Thus, in view of the industrial use of the enzyme, the amount of the FTG to be used for attaining expression of the same effect may be reduced below that of the MTG. Accordingly, the industrial advantage of FTG is noticeable because of the reduction of the cost of producing it.

(b) Thermal stability

Next, FTG and MTG were compared with each other with respect to the easiness of thermal deactivation of them. The amount of the enzyme used for the test was such that would show the activity of the same degree. Each transglutaminase product was first put in a Tris-HCl buffer (pH 8.5) (in the form of a solution comprising 250 microliters of 0.5M Tris-HCl buffer (pH 8.5), 80 microliters of 100 mM DTT, 37 microliters of 1 mM monodansylcadaverine and 1300 microliters of water as the composition) and treated at 0° C., 20° C., 25° C., 30° C., 37° C., 40° C., 42° C., 50° C. or 60° C. for 10 minutes, then cooled with ice for 3 minutes to stop the thermal treatment of the product. Next, 250 microliters of 10 mg/ml dimethylated casein solution and 500 microliters of 50 mM calcium chloride solution were added thereto and reacted at 37° C. for 60 minutes. Afterwards, 100 microliters of 0.5M EDTA was added to each of the reaction liquids so that the enzymatic reaction was stopped.

Figure 13:
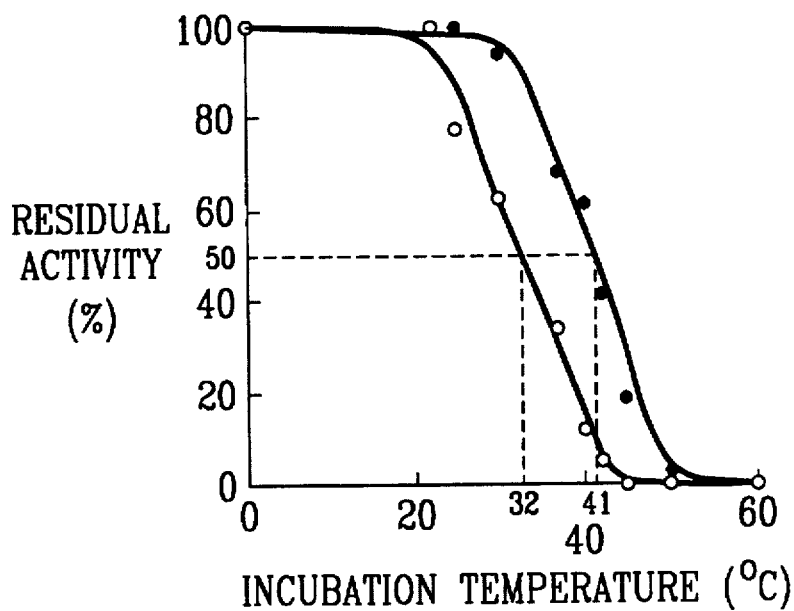
FIG. 13 shows a comparison between the thermal stability of Alaska pollack-derived transglutaminase (FTG) and that of guinea pig-derived transglutaminase (MTG), where ○—○ indicates the relative residual activity of FTG, and ●—● indicates the relative residual activity of MTG.

The fluorescent intensity of each of the thus prepared reaction liquids was measured in the manner as mentioned above, whereby the thermal stability of the enzyme tested was determined. As a result, it was clarified that the temperature of treating FTG for giving the residual activity of 50% was lower than that of MTG by about 9° C., as shown in FIG. 13. The fact indicates that FTG is more easily deactivated than MTG. In combination with the result in the previous relative activity study (a), it is concluded that FTG has a higher enzymatic reactivity and may more easily be deactivated by mere heat treatment of the reaction product than MTG.

(c) Reactivity with actomyosin

Actomyosin (AM) was prepared in the manner mentioned below. First, about 60 ml of a 20 mM Tris-HCl buffer (pH 7.5) containing 0.5M sodium chloride was added to about 30 g of frozen surimi of Alaska pollack (SA grade product by Taiyo Fishery) and homogenized with Excellauto Homogenizer (manufactured by Nissei Industry). This was then subjected to centrifugation three times, each time at 10,000 rpm for 30 seconds, using Hitachi's Himac CR20B2 Model Centrifuge (with rotor of RPR20-2), so that insoluble substances were removed therefrom. The resulting supernatant was put in a dialytic tube (Seamless Cellulose Tubing, imported by Sanko Pure Chemicals) and subjected to dialysis to a 20 mM Tris-HCl buffer (pH 7.5) containing 0.5M sodium chloride for 3 hours and then for 16 hours.

Afterwards, the dialyzed liquid was subjected to centrifugation at 14,000 rpm for 60 minutes to obtain the supernatant. This was filtered through a cotton gauze cloth to prepare an actomyosin solution (about 27 ml). The protein concentration of the solution was measured with BioRad's Protein Assay Kit to be 26.1 mg/ml.

Using the actomyosin as prepared in the manner mentioned above, MTG and FTG were compared with each other with respect to the action and effect thereof on polymerization of the myocin protein. Studies show that polymerization of myocin is an index having a close relation to the "good taste" of marine paste products, including the elasticity displaying function of kamaboko (boiled fish paste product) (see *Nippon Suisan Gakkaishi*, vol. 51, pp. 1559–1565 (1985) and *Nippon Suisan Gakkaishi*, vol. 56, pp. 125–132 (1990)).

The actomyosin as prepared in the manner mentioned above was formed into a solution having a concentration of 10 mg/ml, using a 20 mM Tris-HCl buffer (pH 7.5) containing 0.5M sodium chloride, and one ml of this was put in a test tube (washed test tube Larbo, by Terumo; 15.5×100 mm). Plural test tubes each containing it were prepared. To each of them was added 200 microliters of 50 mM calcium chloride and stirred. Then, 200 microliters of a separately prepared FTG or MTG (both having the same activity as measured by a fluorescent activity measuring method) was added thereto and fully stirred. MTG was one produced by Sigma.

After addition of each transglutaminase, it was reacted at 37° C. for 15 minutes, 30 minutes, 45 minutes and 60 minutes. After the reaction, 100 microliters of the reaction solution was sampled from each test tube, and 100 microliters of a 20 mM Tris-HCl buffer (pH 8.5) containing 8M urea, 2% SDS and 2% beta-mercaptoethanol was added thereto so that the reaction was stopped. Next, 300 microliters of a 125 mM Tris-HCl buffer (pH 6.8) containing 4% SDS, 10% beta-mercaptoethanol, 20% glycerin and 0.002% bromophenol blue was added thereto, and the sample was then heated at 100° C. for one minute to give a sample for SDS-PAGE.

Figure 14:
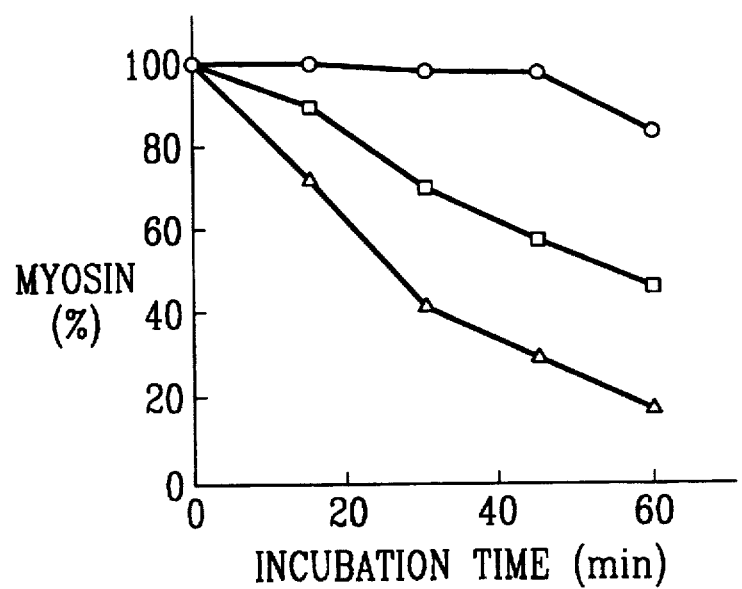
FIG. 14 shows a comparison between the reactivity of Alaska pollack-derived transglutaminase (FTG) and guinea pig-derived transglutaminase (MTG) in polymerization of myosin H chain, where △—△ indicates the reactivity of FTG, □—□ indicates that of MTG, and ○—○ indicates that of a control (no enzyme).

5 microliters of each of the thus prepared samples was applied to SDS-PAGE for electrophoresis, then stained with Coomassie Brilliant Blue, and the monomer amount of the myocin H chain was measured with a densitometer (Ultro Scan XL Laser Densitometer, by LKB). From this, the effect of the transglutaminase tested on the polymerization of the myocin protein was analyzed. The result is shown in FIG. 14, from which it was found that FTG could more rapidly polymerize the myocin protein than MTG. The fact further indicates that FTG is better than MTG also in applications of the transglutaminase enzyme to marine paste products because of reduction of the manufacture cost.

In the past, the sources which could be used to supply transglutaminase have included actinomyces and guinea pigs, but the present invention provides a DNA fragment coding for a fish-derived transglutaminase, a polypeptide which retains and reinforces the texture of traditional processed marine products, such as the boiled fish paste known as "kamaboko", etc., and the function of which is known in naturally occurring substances. By applying recombinant technology to the fish transglutaminase gene obtained according to the present invention, mass production of transglutaminase is possible. Further, applications of the recombinantly-produced enzyme may result in altering the properties of edible protein and improving the nutritional value of foods. In addition to food products, this enzyme may be applied to processing and preparation of pharmaceuticals, and in the manufacture of chemical products.

Obviously, numerous modifications and variations of the present invention are possible in light of the above teachings. It is therefore to be understood that, within the scope of the appended claims, the invention may be practiced otherwise than as specifically described herein.

---

What is claimed as new and desired to be secured by Letters Patent of the United States is:

1. A DNA fragment having a sequence derived from fish, said sequence encoding a polypeptide which possesses transglutaminase activity, said polypeptide having an amino acid sequence selected from the group of sequences consisting of SEQ ID NO:8, SEQ ID NO:10, SEQ ID NO:31, and SEQ ID NO:70.

2. A DNA fragment of claim 1 having a nucleotide sequence selected from the group of sequences consisting of SEQ ID NO:7, SEQ ID NO:9, SEQ ID NO:30, SEQ ID NO:32, SEQ ID NO:69 and SEQ ID NO:71.

3. A DNA fragment derived from *Theragra chalcogramma*, said DNA fragment having the sequence of SEQ ID NO:28.

4. A polypeptide encoded by the DNA fragment of claim 3.

5. A recombinant plasmid which comprises the DNA fragment of any one of claims 1, 2 or 3 and a plasmid vector.

6. The recombinant plasmid of claim 5, wherein said plasmid is an expression vector.

7. A transformant transformed with the recombinant plasmid of claim 5.

8. A transformant transformed with the recombinant plasmid of claim 6.

9. The DNA fragment of either of claim 1 or claim 2, wherein said fish is *Theragra chalcogramma*.

10. The DNA fragment of either of claim 1 or claim 2, wherein said fish is *Paralichthys olivaceus*.

11. A method for the production of a fish-derived polypeptide possessing transglutaminase activity, comprising culturing the transformant of claim 7.

12. A method for the production of a fish-derived polypeptide possessing transglutaminase activity, comprising culturing the transformant of claim 8.

13. A fish-derived polypeptide possessing transglutaminase activity, obtained by culturing the transformant of claim 7.

14. A fish-derived polypeptide possessing transglutaminase activity, obtained by culturing the transformant of claim 8.

* * * * *

UNITED STATES PATENT AND TRADEMARK OFFICE
CERTIFICATE OF CORRECTION

PATENT NO. : 5,607,849
DATED : MARCH 4, 1997
INVENTOR(S) : HISASHI YASUEDA ET AL

It is certified that error appears in the above-identified patent and that said Letters Patent is hereby corrected as shown below:

Column 1, line 67, "TGase belived" should read
    TGase is believed--.

Column 2, line 26, "compriing" should read --comprising--.

Column 3, line 46, "fish-drived" should read --fish-derived--.

Column 5, line 41, "mult-copies" should read --multi-copies--.

Column 7, line 55, "A" should read --a--.

Column 12, line 17, "hours." should read --hour.--.

Column 13, line 49, "*J. Blochem.*" should read --*J. Biochem.*--.

Signed and Sealed this

Seventh Day of July, 1998

Attest:

BRUCE LEHMAN

*Attesting Officer*   *Commissioner of Patents and Trademarks*

SEQUENCE LISTING ( 1 ) GENERAL INFORMATION:

( i i i ) NUMBER OF SEQUENCES: 72

( 2 ) INFORMATION FOR SEQ ID NO:1:

( i ) SEQUENCE CHARACTERISTICS:
        ( A ) LENGTH: 125 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
AATTCATCGA  TTAGTAAGGA  GGTTTAAAAT  GGCTTCTTAT  AAAGGTCTGA  TTGTTGATGT      60

TAATGGTCGT  TCTCATGAAA  ACAACCTGGC  ACATCGTACG  CGTGAAATCG  ACCGTGAGCG     120

CCTGA                                                                     125
```

( 2 ) INFORMATION FOR SEQ ID NO:2:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:2:

```
Tyr  Gly  Gln  Cys  Trp  Val  Phe  Ala
1                  5
```

( 2 ) INFORMATION FOR SEQ ID NO:3:

( i ) SEQUENCE CHARACTERISTICS:
    ( A ) LENGTH: 2085 base pairs
    ( B ) TYPE: nucleic acid
    ( C ) STRANDEDNESS: double
    ( D ) TOPOLOGY: linear ( i i ) MOLECULE TYPE: cDNA to mRNA ( v i ) ORIGINAL SOURCE:
    ( A ) ORGANISM: Pagrus major
    ( F ) TISSUE TYPE: liver ( i x ) FEATURE:
    ( A ) NAME/KEY: CDS
    ( B ) LOCATION: 1..2082

( x i ) SEQUENCE DESCRIPTION: SEQ ID NO:3:

```
GCC  AGC  TAC  AAG  GGG  TTG  ATT  GTT  GAT  GTG  AAT  GGG  AGA  AGT  CAT  GAA     48
Ala  Ser  Tyr  Lys  Gly  Leu  Ile  Val  Asp  Val  Asn  Gly  Arg  Ser  His  Glu
1                  5                      10                     15

AAC  AAC  TTG  GCT  CAC  CGC  ACC  AGG  GAG  ATT  GAT  CGG  GAG  CGC  CTG  ATC     96
Asn  Asn  Leu  Ala  His  Arg  Thr  Arg  Glu  Ile  Asp  Arg  Glu  Arg  Leu  Ile
                   20                      25                     30

GTC  CGC  AGA  GGT  CAA  CCC  TTC  TCC  ATC  ACT  TTG  CAG  TGC  TCT  GAC  TCT    144
Val  Arg  Arg  Gly  Gln  Pro  Phe  Ser  Ile  Thr  Leu  Gln  Cys  Ser  Asp  Ser
          35                      40                          45

CTG  CCG  CCC  AAA  CAC  CAC  CTG  GAG  CTG  GTC  CTG  CAC  CTC  GGT  AAG  AGA    192
Leu  Pro  Pro  Lys  His  His  Leu  Glu  Leu  Val  Leu  His  Leu  Gly  Lys  Arg
     50                      55                          60

GAC  GAG  GTG  GTG  ATC  AAG  GTT  CAG  AAG  GAA  CAT  GGG  GCC  AGA  GAC  AAG    240
Asp  Glu  Val  Val  Ile  Lys  Val  Gln  Lys  Glu  His  Gly  Ala  Arg  Asp  Lys
65                      70                      75                          80

TGG  TGG  TTT  AAC  CAG  CAG  GGA  GCT  CAG  GAT  GAA  ATA  CTG  CTG  ACT  CTG    288
Trp  Trp  Phe  Asn  Gln  Gln  Gly  Ala  Gln  Asp  Glu  Ile  Leu  Leu  Thr  Leu
                    85                      90                      95

CAC  AGC  CCA  GCG  AAC  GCT  GTC  ATT  GGC  CAC  TAC  CGT  CTG  GCT  GTG  TTG    336
His  Ser  Pro  Ala  Asn  Ala  Val  Ile  Gly  His  Tyr  Arg  Leu  Ala  Val  Leu
                    100                     105                     110

GTG  ATG  TCA  CCA  GAT  GGT  CAC  ATC  GTA  GAG  AGG  GCA  GAC  AAA  ATT  AGC    384
Val  Met  Ser  Pro  Asp  Gly  His  Ile  Val  Glu  Arg  Ala  Asp  Lys  Ile  Ser
          115                     120                     125

TTC  CAC  ATG  CTC  TTC  AAC  CCG  TGG  TGC  AGA  GAT  GAT  ATG  GTT  TAC  CTC    432
Phe  His  Met  Leu  Phe  Asn  Pro  Trp  Cys  Arg  Asp  Asp  Met  Val  Tyr  Leu
     130                     135                     140

CCT  GAT  GAG  AGT  AAG  CTC  CAG  GAG  TAT  GTC  ATG  AAT  GAA  GAT  GGA  GTG    480
Pro  Asp  Glu  Ser  Lys  Leu  Gln  Glu  Tyr  Val  Met  Asn  Glu  Asp  Gly  Val
145                     150                     155                     160

ATT  TAC  ATG  GGG  ACC  TGG  GAT  TAC  ATC  AGA  AGT  ATA  CCC  TGG  AAT  TAT    528
Ile  Tyr  Met  Gly  Thr  Trp  Asp  Tyr  Ile  Arg  Ser  Ile  Pro  Trp  Asn  Tyr
                    165                     170                     175

GGA  CAG  TTT  GAG  GAC  TAT  GTG  ATG  GAC  ATC  TGT  TTT  GAA  GTC  TTG  GAC    576
Gly  Gln  Phe  Glu  Asp  Tyr  Val  Met  Asp  Ile  Cys  Phe  Glu  Val  Leu  Asp
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 180 |     |     |     |     | 185 |     |     |     |     | 190 |     |     |      |
| AAC | TCC | CCA | GCT | GCC | TTG | AAA | AAC | TCA | GAG | ATG | GAC | ATT | GAG | CAC | AGA | 624  |
| Asn | Ser | Pro | Ala | Ala | Leu | Lys | Asn | Ser | Glu | Met | Asp | Ile | Glu | His | Arg |      |
|     |     | 195 |     |     |     |     | 200 |     |     |     |     | 205 |     |     |     |      |
| TCA | GAC | CCC | GTC | TAT | GTC | GGC | AGG | ACA | ATC | ACT | GCA | ATG | GTG | AAC | TCT | 672  |
| Ser | Asp | Pro | Val | Tyr | Val | Gly | Arg | Thr | Ile | Thr | Ala | Met | Val | Asn | Ser |      |
|     | 210 |     |     |     |     | 215 |     |     |     |     | 220 |     |     |     |     |      |
| AAC | GGT | GAC | AGG | GGT | GTG | TTG | ACT | GGT | CGC | TGG | GAG | GAG | CCG | TAC | ACT | 720  |
| Asn | Gly | Asp | Arg | Gly | Val | Leu | Thr | Gly | Arg | Trp | Glu | Glu | Pro | Tyr | Thr |      |
| 225 |     |     |     | 230 |     |     |     |     | 235 |     |     |     |     | 240 |     |      |
| GAT | GGG | GTC | GCA | CCG | TAT | CGA | TGG | ACC | GGC | AGC | GTG | CCG | ATC | CTC | CAA | 768  |
| Asp | Gly | Val | Ala | Pro | Tyr | Arg | Trp | Thr | Gly | Ser | Val | Pro | Ile | Leu | Gln |      |
|     |     |     |     | 245 |     |     |     |     | 250 |     |     |     |     | 255 |     |      |
| CAG | TGG | AGC | AAG | GCC | GGG | GTG | AGG | CCG | GTC | AAA | TAT | GGC | CAG | TGC | TGG | 816  |
| Gln | Trp | Ser | Lys | Ala | Gly | Val | Arg | Pro | Val | Lys | Tyr | Gly | Gln | Cys | Trp |      |
|     |     |     |     | 260 |     |     |     |     | 265 |     |     |     |     | 270 |     |      |
| GTG | TTT | GCT | GCC | GTC | GCC | TGC | ACA | GTG | CTG | CGC | TGC | CTG | GGA | ATC | CCA | 864  |
| Val | Phe | Ala | Ala | Val | Ala | Cys | Thr | Val | Leu | Arg | Cys | Leu | Gly | Ile | Pro |      |
|     |     | 275 |     |     |     |     | 280 |     |     |     |     | 285 |     |     |     |      |
| ACA | CGC | CCC | ATC | ACC | AAC | TTC | GCT | TCA | GCC | CAT | GAT | GTC | GAT | GGT | AAC | 912  |
| Thr | Arg | Pro | Ile | Thr | Asn | Phe | Ala | Ser | Ala | His | Asp | Val | Asp | Gly | Asn |      |
|     | 290 |     |     |     |     | 295 |     |     |     |     | 300 |     |     |     |     |      |
| CTC | TCG | GTA | GAC | TTC | CTG | CTG | AAT | GAG | AGA | CTG | GAG | AGC | TTG | GAC | AGT | 960  |
| Leu | Ser | Val | Asp | Phe | Leu | Leu | Asn | Glu | Arg | Leu | Glu | Ser | Leu | Asp | Ser |      |
| 305 |     |     |     |     | 310 |     |     |     |     | 315 |     |     |     |     | 320 |      |
| AGA | CAG | AGA | AGT | GAC | AGT | AGC | TGG | AAC | TTC | CAC | TGT | TGG | GTT | GAA | TCC | 1008 |
| Arg | Gln | Arg | Ser | Asp | Ser | Ser | Trp | Asn | Phe | His | Cys | Trp | Val | Glu | Ser |      |
|     |     |     |     | 325 |     |     |     |     | 330 |     |     |     |     | 335 |     |      |
| TGG | ATG | AGC | AGA | GAG | GAT | CTC | CCT | GAA | GGA | AAT | GAT | GGC | TGG | CAG | GTT | 1056 |
| Trp | Met | Ser | Arg | Glu | Asp | Leu | Pro | Glu | Gly | Asn | Asp | Gly | Trp | Gln | Val |      |
|     |     |     | 340 |     |     |     |     | 345 |     |     |     |     | 350 |     |     |      |
| TTG | GAT | CCC | ACC | CCT | CAA | GAA | CTG | AGT | GAT | GGT | GAG | TTT | TGC | TGT | GGT | 1104 |
| Leu | Asp | Pro | Thr | Pro | Gln | Glu | Leu | Ser | Asp | Gly | Glu | Phe | Cys | Cys | Gly |      |
|     |     | 355 |     |     |     |     | 360 |     |     |     |     | 365 |     |     |     |      |
| CCG | TGT | CCA | GTG | GCG | GCC | ATC | AAG | GAG | GGA | AAT | CTG | GGA | GTG | AAG | TAC | 1152 |
| Pro | Cys | Pro | Val | Ala | Ala | Ile | Lys | Glu | Gly | Asn | Leu | Gly | Val | Lys | Tyr |      |
|     | 370 |     |     |     |     | 375 |     |     |     |     | 380 |     |     |     |     |      |
| GAC | GCC | CCC | TTT | GTA | TTC | GCT | GAG | GTG | AAC | GCT | GAC | ACC | ATC | TAC | TGG | 1200 |
| Asp | Ala | Pro | Phe | Val | Phe | Ala | Glu | Val | Asn | Ala | Asp | Thr | Ile | Tyr | Trp |      |
| 385 |     |     |     |     | 390 |     |     |     |     | 395 |     |     |     |     | 400 |      |
| ATC | GTC | CAA | AAA | GAT | GGC | CAA | CGA | CGG | AAG | ATC | ACA | GAG | GAC | CAT | GCT | 1248 |
| Ile | Val | Gln | Lys | Asp | Gly | Gln | Arg | Arg | Lys | Ile | Thr | Glu | Asp | His | Ala |      |
|     |     |     |     | 405 |     |     |     |     | 410 |     |     |     |     | 415 |     |      |
| AGT | GTG | GGG | AAG | AAC | ATC | AGC | ACA | AAA | AGC | GTT | TAC | GGC | AAC | CAC | AGA | 1296 |
| Ser | Val | Gly | Lys | Asn | Ile | Ser | Thr | Lys | Ser | Val | Tyr | Gly | Asn | His | Arg |      |
|     |     |     | 420 |     |     |     |     | 425 |     |     |     |     | 430 |     |     |      |
| GAA | GAT | GTC | ACT | CTG | CAC | TAC | AAA | TAT | CCT | GAA | GGC | TCC | CAG | AAG | GAG | 1344 |
| Glu | Asp | Val | Thr | Leu | His | Tyr | Lys | Tyr | Pro | Glu | Gly | Ser | Gln | Lys | Glu |      |
|     |     | 435 |     |     |     |     | 440 |     |     |     |     | 445 |     |     |     |      |
| AGG | GAA | GTG | TAC | AAG | AAG | GCG | GGA | CGC | CGG | GTC | ACA | GAG | CCA | TCC | AAC | 1392 |
| Arg | Glu | Val | Tyr | Lys | Lys | Ala | Gly | Arg | Arg | Val | Thr | Glu | Pro | Ser | Asn |      |
|     | 450 |     |     |     |     | 455 |     |     |     |     | 460 |     |     |     |     |      |
| GAG | ATC | GCA | GAA | CAA | GGA | AGA | CTT | CAG | CTG | TCA | ATC | AAG | CAT | GCC | CAG | 1440 |
| Glu | Ile | Ala | Glu | Gln | Gly | Arg | Leu | Gln | Leu | Ser | Ile | Lys | His | Ala | Gln |      |
| 465 |     |     |     |     | 470 |     |     |     |     | 475 |     |     |     |     | 480 |      |
| CCT | GTA | TTT | GGG | ACA | GAC | TTT | GAT | GTG | ATT | GTT | GAG | GTG | AAG | AAT | GAA | 1488 |
| Pro | Val | Phe | Gly | Thr | Asp | Phe | Asp | Val | Ile | Val | Glu | Val | Lys | Asn | Glu |      |
|     |     |     |     | 485 |     |     |     |     | 490 |     |     |     |     | 495 |     |      |
| GGA | GGC | AGA | GAT | GCT | CAT | GCT | CAG | CTG | ACC | ATG | CTG | GCC | ATG | GCA | GTA | 1536 |
| Gly | Gly | Arg | Asp | Ala | His | Ala | Gln | Leu | Thr | Met | Leu | Ala | Met | Ala | Val |      |

| | | | | | | | | | | | | | | | | |
|---|---|---|---|---|---|---|---|---|---|---|---|---|---|---|---|---|
| | | | | 500 | | | | | 505 | | | | | 510 | | |
| ACT | TAC | AAT | TCT | CTC | CGC | CGG | GGG | GAG | TGC | CAG | AGA | AAA | ACA | ATC | AGT | 1584 |
| Thr | Tyr | Asn | Ser | Leu | Arg | Arg | Gly | Glu | Cys | Gln | Arg | Lys | Thr | Ile | Ser | |
| | | 515 | | | | 520 | | | | | 525 | | | | | |
| GTG | ACT | GTG | CCC | GCT | CAC | AAA | GCC | CAC | AAG | GAG | GTT | ATG | CGT | CTG | CAC | 1632 |
| Val | Thr | Val | Pro | Ala | His | Lys | Ala | His | Lys | Glu | Val | Met | Arg | Leu | His | |
| | 530 | | | | | 535 | | | | | 540 | | | | | |
| TAC | GAC | GAC | TAT | GTC | AGG | TGT | GTC | TCT | GAG | CAT | CAC | CTG | ATC | AGG | GTG | 1680 |
| Tyr | Asp | Asp | Tyr | Val | Arg | Cys | Val | Ser | Glu | His | His | Leu | Ile | Arg | Val | |
| 545 | | | | | 550 | | | | | 555 | | | | | 560 | |
| AAA | GCG | CTC | TTA | GAC | GCT | CCA | GGG | GAG | AAC | GGG | CCC | ATC | ATG | ACC | GTG | 1728 |
| Lys | Ala | Leu | Leu | Asp | Ala | Pro | Gly | Glu | Asn | Gly | Pro | Ile | Met | Thr | Val | |
| | | | | 565 | | | | | 570 | | | | | 575 | | |
| GCC | AAC | ATC | CCA | CTG | AGC | ACG | CCT | GAA | CTC | CTT | GTA | CAG | GTG | CCT | GGG | 1776 |
| Ala | Asn | Ile | Pro | Leu | Ser | Thr | Pro | Glu | Leu | Leu | Val | Gln | Val | Pro | Gly | |
| | | | 580 | | | | | 585 | | | | | 590 | | | |
| AAG | GCT | GTT | GTA | TGG | GAA | CCA | CTG | ACA | GCC | TAC | GTC | TCC | TTC | ACC | AAT | 1824 |
| Lys | Ala | Val | Val | Trp | Glu | Pro | Leu | Thr | Ala | Tyr | Val | Ser | Phe | Thr | Asn | |
| | | 595 | | | | | 600 | | | | | 605 | | | | |
| CCT | CTG | CCA | GTT | CCT | CTG | AAG | GGT | GGC | GTT | TTC | ACT | TTG | GAG | GGT | GCT | 1872 |
| Pro | Leu | Pro | Val | Pro | Leu | Lys | Gly | Gly | Val | Phe | Thr | Leu | Glu | Gly | Ala | |
| | 610 | | | | | 615 | | | | | 620 | | | | | |
| GGC | CTG | CTG | TCT | GCC | ACT | CAG | ATC | CAT | GTT | AAT | GGT | GCT | GTA | GCT | CCA | 1920 |
| Gly | Leu | Leu | Ser | Ala | Thr | Gln | Ile | His | Val | Asn | Gly | Ala | Val | Ala | Pro | |
| 625 | | | | | 630 | | | | | 635 | | | | | 640 | |
| AGT | GGG | AAA | GTG | TCT | GTC | AAG | CTC | TCT | TTC | TCC | CCC | ATG | CGC | ACC | GGG | 1968 |
| Ser | Gly | Lys | Val | Ser | Val | Lys | Leu | Ser | Phe | Ser | Pro | Met | Arg | Thr | Gly | |
| | | | | 645 | | | | | 650 | | | | | 655 | | |
| GTG | AGG | AAG | CTC | CTG | GTG | GAC | TTT | GAC | TCT | GAC | AGA | CTG | AAG | GAC | GTG | 2016 |
| Val | Arg | Lys | Leu | Leu | Val | Asp | Phe | Asp | Ser | Asp | Arg | Leu | Lys | Asp | Val | |
| | | | 660 | | | | | 665 | | | | | 670 | | | |
| AAG | GGT | GTC | ACC | ACC | GTG | GTT | GTC | CAC | AAG | AAA | TAC | AGA | TCT | CTA | ATT | 2064 |
| Lys | Gly | Val | Thr | Thr | Val | Val | Val | His | Lys | Lys | Tyr | Arg | Ser | Leu | Ile | |
| | | 675 | | | | | 680 | | | | | 685 | | | | |
| ACT | GGA | CTT | CAC | ACA | GAC | TAA | | | | | | | | | | 2085 |
| Thr | Gly | Leu | His | Thr | Asp | | | | | | | | | | | |
| 690 | | | | | | | | | | | | | | | | |

(2) INFORMATION FOR SEQ ID NO:4:

(i) SEQUENCE CHARACTERISTICS:
  (A) LENGTH: 694 amino acids
  (B) TYPE: amino acid
  (D) TOPOLOGY: linear (ii) MOLECULE TYPE: protein (xi) SEQUENCE DESCRIPTION: SEQ ID NO:4:

| | | | | | | | | | | | | | | |
|---|---|---|---|---|---|---|---|---|---|---|---|---|---|---|
| Ala | Ser | Tyr | Lys | Gly | Leu | Ile | Val | Asp | Val | Asn | Gly | Arg | Ser | His | Glu |
| 1 | | | | 5 | | | | | 10 | | | | | 15 | |
| Asn | Asn | Leu | Ala | His | Arg | Thr | Arg | Glu | Ile | Asp | Arg | Glu | Arg | Leu | Ile |
| | | | 20 | | | | | 25 | | | | | 30 | | |
| Val | Arg | Arg | Gly | Gln | Pro | Phe | Ser | Ile | Thr | Leu | Gln | Cys | Ser | Asp | Ser |
| | | 35 | | | | | 40 | | | | | 45 | | | |
| Leu | Pro | Pro | Lys | His | His | Leu | Glu | Leu | Val | Leu | His | Leu | Gly | Lys | Arg |
| | 50 | | | | | 55 | | | | | 60 | | | | |
| Asp | Glu | Val | Val | Ile | Lys | Val | Gln | Lys | Glu | His | Gly | Ala | Arg | Asp | Lys |
| 65 | | | | | 70 | | | | | 75 | | | | | 80 |
| Trp | Trp | Phe | Asn | Gln | Gln | Gly | Ala | Gln | Asp | Glu | Ile | Leu | Leu | Thr | Leu |
| | | | 85 | | | | | 90 | | | | | 95 | | |

| His | Ser | Pro | Ala | Asn | Ala | Val | Ile | Gly | His | Tyr | Arg | Leu | Ala | Val | Leu |
|---|---|---|---|---|---|---|---|---|---|---|---|---|---|---|---|
| | | | 100 | | | | 105 | | | | | | 110 | | |
| Val | Met | Ser | Pro | Asp | Gly | His | Ile | Val | Glu | Arg | Ala | Asp | Lys | Ile | Ser |
| | | 115 | | | | 120 | | | | | 125 | | | | |
| Phe | His | Met | Leu | Phe | Asn | Pro | Trp | Cys | Arg | Asp | Asp | Met | Val | Tyr | Leu |
| | 130 | | | | 135 | | | | | 140 | | | | | |
| Pro | Asp | Glu | Ser | Lys | Leu | Gln | Glu | Tyr | Val | Met | Asn | Glu | Asp | Gly | Val |
| 145 | | | | | 150 | | | | | 155 | | | | | 160 |
| Ile | Tyr | Met | Gly | Thr | Trp | Asp | Tyr | Ile | Arg | Ser | Ile | Pro | Trp | Asn | Tyr |
| | | | | 165 | | | | | 170 | | | | | 175 | |
| Gly | Gln | Phe | Glu | Asp | Tyr | Val | Met | Asp | Ile | Cys | Phe | Glu | Val | Leu | Asp |
| | | | | 180 | | | | 185 | | | | | 190 | | |
| Asn | Ser | Pro | Ala | Ala | Leu | Lys | Asn | Ser | Glu | Met | Asp | Ile | Glu | His | Arg |
| | | | 195 | | | | 200 | | | | | 205 | | | |
| Ser | Asp | Pro | Val | Tyr | Val | Gly | Arg | Thr | Ile | Thr | Ala | Met | Val | Asn | Ser |
| | 210 | | | | | 215 | | | | | 220 | | | | |
| Asn | Gly | Asp | Arg | Gly | Val | Leu | Thr | Gly | Arg | Trp | Glu | Glu | Pro | Tyr | Thr |
| 225 | | | | | 230 | | | | | 235 | | | | | 240 |
| Asp | Gly | Val | Ala | Pro | Tyr | Arg | Trp | Thr | Gly | Ser | Val | Pro | Ile | Leu | Gln |
| | | | | 245 | | | | | 250 | | | | | 255 | |
| Gln | Trp | Ser | Lys | Ala | Gly | Val | Arg | Pro | Val | Lys | Tyr | Gly | Gln | Cys | Trp |
| | | | 260 | | | | | 265 | | | | | 270 | | |
| Val | Phe | Ala | Ala | Val | Ala | Cys | Thr | Val | Leu | Arg | Cys | Leu | Gly | Ile | Pro |
| | | 275 | | | | | 280 | | | | | 285 | | | |
| Thr | Arg | Pro | Ile | Thr | Asn | Phe | Ala | Ser | Ala | His | Asp | Val | Asp | Gly | Asn |
| | 290 | | | | | 295 | | | | | 300 | | | | |
| Leu | Ser | Val | Asp | Phe | Leu | Leu | Asn | Glu | Arg | Leu | Glu | Ser | Leu | Asp | Ser |
| 305 | | | | | 310 | | | | | 315 | | | | | 320 |
| Arg | Gln | Arg | Ser | Asp | Ser | Ser | Trp | Asn | Phe | His | Cys | Trp | Val | Glu | Ser |
| | | | | 325 | | | | | 330 | | | | | 335 | |
| Trp | Met | Ser | Arg | Glu | Asp | Leu | Pro | Glu | Gly | Asn | Asp | Gly | Trp | Gln | Val |
| | | | 340 | | | | | 345 | | | | | 350 | | |
| Leu | Asp | Pro | Thr | Pro | Gln | Glu | Leu | Ser | Asp | Gly | Glu | Phe | Cys | Cys | Gly |
| | | 355 | | | | | 360 | | | | | 365 | | | |
| Pro | Cys | Pro | Val | Ala | Ala | Ile | Lys | Glu | Gly | Asn | Leu | Gly | Val | Lys | Tyr |
| | 370 | | | | | 375 | | | | | 380 | | | | |
| Asp | Ala | Pro | Phe | Val | Phe | Ala | Glu | Val | Asn | Ala | Asp | Thr | Ile | Tyr | Trp |
| 385 | | | | | 390 | | | | | 395 | | | | | 400 |
| Ile | Val | Gln | Lys | Asp | Gly | Gln | Arg | Arg | Lys | Ile | Thr | Glu | Asp | His | Ala |
| | | | | 405 | | | | | 410 | | | | | 415 | |
| Ser | Val | Gly | Lys | Asn | Ile | Ser | Thr | Lys | Ser | Val | Tyr | Gly | Asn | His | Arg |
| | | | 420 | | | | | 425 | | | | | 430 | | |
| Glu | Asp | Val | Thr | Leu | His | Tyr | Lys | Tyr | Pro | Glu | Gly | Ser | Gln | Lys | Glu |
| | | 435 | | | | | 440 | | | | | 445 | | | |
| Arg | Glu | Val | Tyr | Lys | Lys | Ala | Gly | Arg | Arg | Val | Thr | Glu | Pro | Ser | Asn |
| | 450 | | | | | 455 | | | | | 460 | | | | |
| Glu | Ile | Ala | Glu | Gln | Gly | Arg | Leu | Gln | Leu. | Ser | Ile | Lys | His | Ala | Gln |
| 465 | | | | | 470 | | | | | 475 | | | | | 480 |
| Pro | Val | Phe | Gly | Thr | Asp | Phe | Asp | Val | Ile | Val | Glu | Val | Lys | Asn | Glu |
| | | | | 485 | | | | | 490 | | | | | 495 | |
| Gly | Gly | Arg | Asp | Ala | His | Ala | Gln | Leu | Thr | Met | Leu | Ala | Met | Ala | Val |
| | | | 500 | | | | | 505 | | | | | 510 | | |
| Thr | Tyr | Asn | Ser | Leu | Arg | Arg | Gly | Glu | Cys | Gln | Arg | Lys | Thr | Ile | Ser |
| | | | 515 | | | | | 520 | | | | | 525 | | |

| | | | | | | | | | | | | | | | |
|---|---|---|---|---|---|---|---|---|---|---|---|---|---|---|---|
| Val | Thr<br>530 | Val | Pro | Ala | His | Lys<br>535 | Ala | His | Lys | Glu<br>540 | Val | Met | Arg | Leu | His |
| Tyr<br>545 | Asp | Asp | Tyr | Val | Arg<br>550 | Cys | Val | Ser | Glu | His<br>555 | His | Leu | Ile | Arg | Val<br>560 |
| Lys | Ala | Leu | Leu | Asp<br>565 | Ala | Pro | Gly | Glu | Asn<br>570 | Gly | Pro | Ile | Met | Thr<br>575 | Val |
| Ala | Asn | Ile | Pro<br>580 | Leu | Ser | Thr | Pro | Glu<br>585 | Leu | Leu | Val | Gln | Val<br>590 | Pro | Gly |
| Lys | Ala | Val<br>595 | Val | Trp | Glu | Pro | Leu<br>600 | Thr | Ala | Tyr | Val | Ser<br>605 | Phe | Thr | Asn |
| Pro | Leu<br>610 | Pro | Val | Pro | Leu | Lys<br>615 | Gly | Gly | Val | Phe | Thr<br>620 | Leu | Glu | Gly | Ala |
| Gly<br>625 | Leu | Leu | Ser | Ala | Thr<br>630 | Gln | Ile | His | Val | Asn<br>635 | Gly | Ala | Val | Ala | Pro<br>640 |
| Ser | Gly | Lys | Val | Ser<br>645 | Val | Lys | Leu | Ser | Phe<br>650 | Ser | Pro | Met | Arg | Thr<br>655 | Gly |
| Val | Arg | Lys | Leu<br>660 | Leu | Val | Asp | Phe | Asp<br>665 | Ser | Asp | Arg | Leu | Lys<br>670 | Asp | Val |
| Lys | Gly | Val<br>675 | Thr | Thr | Val | Val | Val<br>680 | His | Lys | Lys | Tyr | Arg<br>685 | Ser | Leu | Ile |
| Thr | Gly<br>690 | Leu | His | Thr | Asp | | | | | | | | | | |

( 2 ) INFORMATION FOR SEQ ID NO:5:

( i ) SEQUENCE CHARACTERISTICS:
        ( A ) LENGTH: 2520 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: Pagrus major
        ( F ) TISSUE TYPE: liver ( i x ) FEATURE:
        ( A ) NAME/KEY: CDS
        ( B ) LOCATION: 34..2121

( x i ) SEQUENCE DESCRIPTION: SEQ ID NO:5:

| | | | | | | | | | | |
|---|---|---|---|---|---|---|---|---|---|---|
| CTTTAACAGA | CTTTGATAGG | AAGAAGATCT | GCG<br> | ATG<br>Met<br>1 | GCC<br>Ala | AGC<br>Ser | TAC<br>Tyr | AAG<br>Lys<br>5 | GGG<br>Gly | TTG<br>Leu | 54 |
| ATT<br>Ile | GTT<br>Val | GAT<br>Asp<br>10 | GTG<br>Val | AAT<br>Asn | GGG<br>Gly | AGA<br>Arg | AGT<br>Ser<br>15 | CAT<br>His | GAA<br>Glu | AAC<br>Asn | AAC<br>Asn | TTG<br>Leu<br>20 | GCT<br>Ala | CAC<br>His | CGC<br>Arg | 102 |
| ACC<br>Thr | AGG<br>Arg<br>25 | GAG<br>Glu | ATT<br>Ile | GAT<br>Asp | CGG<br>Arg | GAG<br>Glu<br>30 | CGC<br>Arg | CTG<br>Leu | ATC<br>Ile | GTC<br>Val | CGC<br>Arg<br>35 | AGA<br>Arg | GGT<br>Gly | CAA<br>Gln | CCC<br>Pro | 150 |
| TTC<br>Phe<br>40 | TCC<br>Ser | ATC<br>Ile | ACT<br>Thr | TTG<br>Leu | CAG<br>Gln<br>45 | TGC<br>Cys | TCT<br>Ser | GAC<br>Asp | TCT<br>Ser | CTG<br>Leu<br>50 | CCG<br>Pro | CCC<br>Pro | AAA<br>Lys | CAC<br>His | CAC<br>His<br>55 | 198 |
| CTG<br>Leu | GAG<br>Glu | CTG<br>Leu | GTC<br>Val | CTG<br>Leu<br>60 | CAC<br>His | CTC<br>Leu | GGT<br>Gly | AAG<br>Lys | AGA<br>Arg<br>65 | GAC<br>Asp | GAG<br>Glu | GTG<br>Val | GTG<br>Val | ATC<br>Ile<br>70 | AAG<br>Lys | 246 |
| GTT<br>Val | CAG<br>Gln | AAG<br>Lys | GAA<br>Glu | CAT<br>His<br>75 | GGG<br>Gly | GCC<br>Ala | AGA<br>Arg | GAC<br>Asp | AAG<br>Lys<br>80 | TGG<br>Trp | TGG<br>Trp | TTT<br>Phe | AAC<br>Asn | CAG<br>Gln<br>85 | CAG<br>Gln | 294 |
| GGA<br>Gly | GCT<br>Ala | CAG<br>Gln | GAT<br>Asp | GAA<br>Glu | ATA<br>Ile | CTG<br>Leu | CTG<br>Leu | ACT<br>Thr | CTG<br>Leu | CAC<br>His | AGC<br>Ser | CCA<br>Pro | GCG<br>Ala | AAC<br>Asn | GCT<br>Ala | 342 |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Gly | Ala | Gln | Asp | Glu | Ile | Leu | Leu | Thr | Leu | His | Ser | Pro | Ala | Asn | Ala |      |
|     |     | 90  |     |     |     |     | 95  |     |     |     |     | 100 |     |     |     |      |
| GTC | ATT | GGC | CAC | TAC | CGT | CTG | GCT | GTG | TTG | GTG | ATG | TCA | CCA | GAT | GGT | 390  |
| Val | Ile | Gly | His | Tyr | Arg | Leu | Ala | Val | Leu | Val | Met | Ser | Pro | Asp | Gly |      |
|     |     | 105 |     |     |     | 110 |     |     |     |     | 115 |     |     |     |     |      |
| CAC | ATC | GTA | GAG | AGG | GCA | GAC | AAA | ATT | AGC | TTC | CAC | ATG | CTC | TTC | AAC | 438  |
| His | Ile | Val | Glu | Arg | Ala | Asp | Lys | Ile | Ser | Phe | His | Met | Leu | Phe | Asn |      |
|     | 120 |     |     |     |     | 125 |     |     |     |     | 130 |     |     |     | 135 |      |
| CCG | TGG | TGC | AGA | GAT | GAT | ATG | GTT | TAC | CTC | CCT | GAT | GAG | AGT | AAG | CTC | 486  |
| Pro | Trp | Cys | Arg | Asp | Asp | Met | Val | Tyr | Leu | Pro | Asp | Glu | Ser | Lys | Leu |      |
|     |     |     |     | 140 |     |     |     |     | 145 |     |     |     |     | 150 |     |      |
| CAG | GAG | TAT | GTC | ATG | AAT | GAA | GAT | GGA | GTG | ATT | TAC | ATG | GGG | ACC | TGG | 534  |
| Gln | Glu | Tyr | Val | Met | Asn | Glu | Asp | Gly | Val | Ile | Tyr | Met | Gly | Thr | Trp |      |
|     |     |     |     | 155 |     |     |     |     | 160 |     |     |     |     | 165 |     |      |
| GAT | TAC | ATC | AGA | AGT | ATA | CCC | TGG | AAT | TAT | GGA | CAG | TTT | GAG | GAC | TAT | 582  |
| Asp | Tyr | Ile | Arg | Ser | Ile | Pro | Trp | Asn | Tyr | Gly | Gln | Phe | Glu | Asp | Tyr |      |
|     |     | 170 |     |     |     |     | 175 |     |     |     |     | 180 |     |     |     |      |
| GTG | ATG | GAC | ATC | TGT | TTT | GAA | GTC | TTG | GAC | AAC | TCC | CCA | GCT | GCC | TTG | 630  |
| Val | Met | Asp | Ile | Cys | Phe | Glu | Val | Leu | Asp | Asn | Ser | Pro | Ala | Ala | Leu |      |
|     | 185 |     |     |     |     | 190 |     |     |     |     | 195 |     |     |     |     |      |
| AAA | AAC | TCA | GAG | ATG | GAC | ATT | GAG | CAC | AGA | TCA | GAC | CCC | GTC | TAT | GTC | 678  |
| Lys | Asn | Ser | Glu | Met | Asp | Ile | Glu | His | Arg | Ser | Asp | Pro | Val | Tyr | Val |      |
| 200 |     |     |     |     | 205 |     |     |     |     | 210 |     |     |     |     | 215 |      |
| GGC | AGG | ACA | ATC | ACT | GCA | ATG | GTG | AAC | TCT | AAC | GGT | GAC | AGG | GGT | GTG | 726  |
| Gly | Arg | Thr | Ile | Thr | Ala | Met | Val | Asn | Ser | Asn | Gly | Asp | Arg | Gly | Val |      |
|     |     |     |     | 220 |     |     |     |     | 225 |     |     |     |     | 230 |     |      |
| TTG | ACT | GGT | CGC | TGG | GAG | GAG | CCG | TAC | ACT | GAT | GGG | GTC | GCA | CCG | TAT | 774  |
| Leu | Thr | Gly | Arg | Trp | Glu | Glu | Pro | Tyr | Thr | Asp | Gly | Val | Ala | Pro | Tyr |      |
|     |     |     | 235 |     |     |     |     | 240 |     |     |     |     | 245 |     |     |      |
| CGA | TGG | ACC | GGC | AGC | GTG | CCG | ATC | CTC | CAA | CAG | TGG | AGC | AAG | GCC | GGG | 822  |
| Arg | Trp | Thr | Gly | Ser | Val | Pro | Ile | Leu | Gln | Gln | Trp | Ser | Lys | Ala | Gly |      |
|     |     | 250 |     |     |     |     | 255 |     |     |     |     | 260 |     |     |     |      |
| GTG | AGG | CCG | GTC | AAA | TAT | GGC | CAG | TGC | TGG | GTG | TTT | GCT | GCC | GTC | GCC | 870  |
| Val | Arg | Pro | Val | Lys | Tyr | Gly | Gln | Cys | Trp | Val | Phe | Ala | Ala | Val | Ala |      |
|     | 265 |     |     |     |     | 270 |     |     |     |     | 275 |     |     |     |     |      |
| TGC | ACA | GTG | CTG | CGC | TGC | CTG | GGA | ATC | CCA | ACA | CGC | CCC | ATC | ACC | AAC | 918  |
| Cys | Thr | Val | Leu | Arg | Cys | Leu | Gly | Ile | Pro | Thr | Arg | Pro | Ile | Thr | Asn |      |
| 280 |     |     |     |     | 285 |     |     |     |     | 290 |     |     |     |     | 295 |      |
| TTC | GCT | TCA | GCC | CAT | GAT | GTC | GAT | GGT | AAC | CTC | TCG | GTA | GAC | TTC | CTG | 966  |
| Phe | Ala | Ser | Ala | His | Asp | Val | Asp | Gly | Asn | Leu | Ser | Val | Asp | Phe | Leu |      |
|     |     |     |     | 300 |     |     |     |     | 305 |     |     |     |     | 310 |     |      |
| CTG | AAT | GAG | AGA | CTG | GAG | AGC | TTG | GAC | AGT | AGA | CAG | AGA | AGT | GAC | AGT | 1014 |
| Leu | Asn | Glu | Arg | Leu | Glu | Ser | Leu | Asp | Ser | Arg | Gln | Arg | Ser | Asp | Ser |      |
|     |     |     | 315 |     |     |     |     | 320 |     |     |     |     | 325 |     |     |      |
| AGC | TGG | AAC | TTC | CAC | TGT | TGG | GTT | GAA | TCC | TGG | ATG | AGC | AGA | GAG | GAT | 1062 |
| Ser | Trp | Asn | Phe | His | Cys | Trp | Val | Glu | Ser | Trp | Met | Ser | Arg | Glu | Asp |      |
|     |     | 330 |     |     |     |     | 335 |     |     |     |     | 340 |     |     |     |      |
| CTC | CCT | GAA | GGA | AAT | GAT | GGC | TGG | CAG | GTT | TTG | GAT | CCC | ACC | CCT | CAA | 1110 |
| Leu | Pro | Glu | Gly | Asn | Asp | Gly | Trp | Gln | Val | Leu | Asp | Pro | Thr | Pro | Gln |      |
|     | 345 |     |     |     |     | 350 |     |     |     |     | 355 |     |     |     |     |      |
| GAA | CTG | AGT | GAT | GGT | GAG | TTT | TGC | TGT | GGT | CCG | TGT | CCA | GTG | GCG | GCC | 1158 |
| Glu | Leu | Ser | Asp | Gly | Glu | Phe | Cys | Cys | Gly | Pro | Cys | Pro | Val | Ala | Ala |      |
| 360 |     |     |     |     | 365 |     |     |     |     | 370 |     |     |     |     | 375 |      |
| ATC | AAG | GAG | GGA | AAT | CTG | GGA | GTG | AAG | TAC | GAC | GCC | CCC | TTT | GTA | TTC | 1206 |
| Ile | Lys | Glu | Gly | Asn | Leu | Gly | Val | Lys | Tyr | Asp | Ala | Pro | Phe | Val | Phe |      |
|     |     |     |     | 380 |     |     |     |     | 385 |     |     |     |     | 390 |     |      |
| GCT | GAG | GTG | AAC | GCT | GAC | ACC | ATC | TAC | TGG | ATC | GTC | CAA | AAA | GAT | GGC | 1254 |
| Ala | Glu | Val | Asn | Ala | Asp | Thr | Ile | Tyr | Trp | Ile | Val | Gln | Lys | Asp | Gly |      |
|     |     |     | 395 |     |     |     |     | 400 |     |     |     |     | 405 |     |     |      |
| CAA | CGA | CGG | AAG | ATC | ACA | GAG | GAC | CAT | GCT | AGT | GTG | GGG | AAG | AAC | ATC | 1302 |

| | | | | | | | | | | | | | | |
|---|---|---|---|---|---|---|---|---|---|---|---|---|---|---|
| Gln | Arg | Arg 410 | Lys | Ile | Thr | Glu | Asp 415 | His | Ala | Ser | Val | Gly 420 | Lys | Asn | Ile |

| AGC | ACA | AAA | AGC | GTT | TAC | GGC | AAC | CAC | AGA | GAA | GAT | GTC | ACT | CTG | CAC | 1350 |
|---|---|---|---|---|---|---|---|---|---|---|---|---|---|---|---|---|
| Ser | Thr 425 | Lys | Ser | Val | Tyr | Gly 430 | Asn | His | Arg | Glu | Asp 435 | Val | Thr | Leu | His | |

| TAC | AAA | TAT | CCT | GAA | GGC | TCC | CAG | AAG | GAG | AGG | GAA | GTG | TAC | AAG | AAG | 1398 |
|---|---|---|---|---|---|---|---|---|---|---|---|---|---|---|---|---|
| Tyr 440 | Lys | Tyr | Pro | Glu | Gly 445 | Ser | Gln | Lys | Glu | Arg 450 | Glu | Val | Tyr | Lys | Lys 455 | |

| GCG | GGA | CGC | CGG | GTC | ACA | GAG | CCA | TCC | AAC | GAG | ATC | GCA | GAA | CAA | GGA | 1446 |
|---|---|---|---|---|---|---|---|---|---|---|---|---|---|---|---|---|
| Ala | Gly | Arg | Arg | Val 460 | Thr | Glu | Pro | Ser | Asn 465 | Glu | Ile | Ala | Glu | Gln 470 | Gly | |

| AGA | CTT | CAG | CTG | TCA | ATC | AAG | CAT | GCC | CAG | CCT | GTA | TTT | GGG | ACA | GAC | 1494 |
|---|---|---|---|---|---|---|---|---|---|---|---|---|---|---|---|---|
| Arg | Leu | Gln | Leu | Ser 475 | Ile | Lys | His | Ala | Gln 480 | Pro | Val | Phe | Gly | Thr 485 | Asp | |

| TTT | GAT | GTG | ATT | GTT | GAG | GTG | AAG | AAT | GAA | GGA | GGC | AGA | GAT | GCT | CAT | 1542 |
|---|---|---|---|---|---|---|---|---|---|---|---|---|---|---|---|---|
| Phe | Asp | Val 490 | Ile | Val | Glu | Val | Lys 495 | Asn | Glu | Gly | Gly | Arg 500 | Asp | Ala | His | |

| GCT | CAG | CTG | ACC | ATG | CTG | GCC | ATG | GCA | GTA | ACT | TAC | AAT | TCT | CTC | CGC | 1590 |
|---|---|---|---|---|---|---|---|---|---|---|---|---|---|---|---|---|
| Ala | Gln | Leu 505 | Thr | Met | Leu | Ala | Met 510 | Ala | Val | Thr | Tyr | Asn 515 | Ser | Leu | Arg | |

| CGG | GGG | GAG | TGC | CAG | AGA | AAA | ACA | ATC | AGT | GTG | ACT | GTG | CCC | GCT | CAC | 1638 |
|---|---|---|---|---|---|---|---|---|---|---|---|---|---|---|---|---|
| Arg 520 | Gly | Glu | Cys | Gln | Arg 525 | Lys | Thr | Ile | Ser | Val 530 | Thr | Val | Pro | Ala | His 535 | |

| AAA | GCC | CAC | AAG | GAG | GTT | ATG | CGT | CTG | CAC | TAC | GAC | GAC | TAT | GTC | AGG | 1686 |
|---|---|---|---|---|---|---|---|---|---|---|---|---|---|---|---|---|
| Lys | Ala | His | Lys | Glu 540 | Val | Met | Arg | Leu | His 545 | Tyr | Asp | Asp | Tyr | Val 550 | Arg | |

| TGT | GTC | TCT | GAG | CAT | CAC | CTG | ATC | AGG | GTG | AAA | GCG | CTC | TTA | GAC | GCT | 1734 |
|---|---|---|---|---|---|---|---|---|---|---|---|---|---|---|---|---|
| Cys | Val | Ser | Glu 555 | His | His | Leu | Ile | Arg 560 | Val | Lys | Ala | Leu | Leu 565 | Asp | Ala | |

| CCA | GGG | GAG | AAC | GGG | CCC | ATC | ATG | ACC | GTG | GCC | AAC | ATC | CCA | CTG | AGC | 1782 |
|---|---|---|---|---|---|---|---|---|---|---|---|---|---|---|---|---|
| Pro | Gly | Glu 570 | Asn | Gly | Pro | Ile | Met 575 | Thr | Val | Ala | Asn | Ile 580 | Pro | Leu | Ser | |

| ACG | CCT | GAA | CTC | CTT | GTA | CAG | GTG | CCT | GGG | AAG | GCT | GTT | GTA | TGG | GAA | 1830 |
|---|---|---|---|---|---|---|---|---|---|---|---|---|---|---|---|---|
| Thr | Pro 585 | Glu | Leu | Leu | Val | Gln 590 | Val | Pro | Gly | Lys | Ala 595 | Val | Val | Trp | Glu | |

| CCA | CTG | ACA | GCC | TAC | GTC | TCC | TTC | ACC | AAT | CCT | CTG | CCA | GTT | CCT | CTG | 1878 |
|---|---|---|---|---|---|---|---|---|---|---|---|---|---|---|---|---|
| Pro 600 | Leu | Thr | Ala | Tyr | Val 605 | Ser | Phe | Thr | Asn | Pro 610 | Leu | Pro | Val | Pro | Leu 615 | |

| AAG | GGT | GGC | GTT | TTC | ACT | TTG | GAG | GGT | GCT | GGC | CTG | CTG | TCT | GCC | ACT | 1926 |
|---|---|---|---|---|---|---|---|---|---|---|---|---|---|---|---|---|
| Lys | Gly | Gly | Val | Phe 620 | Thr | Leu | Glu | Gly | Ala 625 | Gly | Leu | Leu | Ser | Ala 630 | Thr | |

| CAG | ATC | CAT | GTT | AAT | GGT | GCT | GTA | GCT | CCA | AGT | GGG | AAA | GTG | TCT | GTC | 1974 |
|---|---|---|---|---|---|---|---|---|---|---|---|---|---|---|---|---|
| Gln | Ile | His | Val 635 | Asn | Gly | Ala | Val | Ala 640 | Pro | Ser | Gly | Lys | Val 645 | Ser | Val | |

| AAG | CTC | TCT | TTC | TCC | CCC | ATG | CGC | ACC | GGG | GTG | AGG | AAG | CTC | CTG | GTG | 2022 |
|---|---|---|---|---|---|---|---|---|---|---|---|---|---|---|---|---|
| Lys | Leu | Ser 650 | Phe | Ser | Pro | Met | Arg 655 | Thr | Gly | Val | Arg | Lys 660 | Leu | Leu | Val | |

| GAC | TTT | GAC | TCT | GAC | AGA | CTG | AAG | GAC | GTG | AAG | GGT | GTC | ACC | ACC | GTG | 2070 |
|---|---|---|---|---|---|---|---|---|---|---|---|---|---|---|---|---|
| Asp | Phe 665 | Asp | Ser | Asp | Arg | Leu 670 | Lys | Asp | Val | Lys | Gly 675 | Val | Thr | Thr | Val | |

| GTT | GTC | CAC | AAG | AAA | TAC | AGA | TCT | CTA | ATT | ACT | GGA | CTT | CAC | ACA | GAC | 2118 |
|---|---|---|---|---|---|---|---|---|---|---|---|---|---|---|---|---|
| Val 680 | Val | His | Lys | Lys | Tyr 685 | Arg | Ser | Leu | Ile | Thr 690 | Gly | Leu | His | Thr | Asp 695 | |

| TAAAATAGAC | ATATCTTATA | TTATGTGATT | TTGTGACATT | TCCTAGATGT | GAGGTGGAGG | 2178 |
|---|---|---|---|---|---|---|
| TGATGTATAA | GGTAGATGAT | ATCAACCGCT | CAGTGTTATA | ACAGTTTATA | ATGCAAATAA | 2238 |
| GTTCCACTTA | AATGATACTG | TAGCTATGTC | CACGAAGAAA | ATTCTTGACA | CAGTGTTAGT | 2298 |
| TTGATTACCT | TAAAGCCTTA | AAGCCACTGT | ATGTCAGATG | TGAACTTGTC | TGGCTTTGCA | 2358 |
| TTAAAACCTG | GCACATGTTG | CTCACATGGA | AATGCACAGA | AGCACAACAG | GTGACGGCCT | 2418 |

```
CTAGATGGAA AATATGTGCG TTTTGTTTCT GTTACTCCTC TGTTTTATTG CCAAATTCAA    2478

GATGCTTCCT TCTGTCTTCA TTCCAAATGA CTGCTGGTTT TT                       2520
```

( 2 ) INFORMATION FOR SEQ ID NO:6:

( i ) SEQUENCE CHARACTERISTICS:
        ( A ) LENGTH: 695 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Ala  Ser  Tyr  Lys  Gly  Leu  Ile  Val  Asp  Val  Asn  Gly  Arg  Ser  His
 1              5                    10                        15

Glu  Asn  Asn  Leu  Ala  His  Arg  Thr  Arg  Glu  Ile  Asp  Arg  Glu  Arg  Leu
               20                    25                        30

Ile  Val  Arg  Arg  Gly  Gln  Pro  Phe  Ser  Ile  Thr  Leu  Gln  Cys  Ser  Asp
          35                    40                        45

Ser  Leu  Pro  Pro  Lys  His  His  Leu  Glu  Leu  Val  Leu  His  Leu  Gly  Lys
     50                    55                        60

Arg  Asp  Glu  Val  Val  Ile  Lys  Val  Gln  Lys  Glu  His  Gly  Ala  Arg  Asp
65                        70                        75                        80

Lys  Trp  Trp  Phe  Asn  Gln  Gln  Gly  Ala  Gln  Asp  Glu  Ile  Leu  Leu  Thr
                    85                        90                        95

Leu  His  Ser  Pro  Ala  Asn  Ala  Val  Ile  Gly  His  Tyr  Arg  Leu  Ala  Val
               100                       105                      110

Leu  Val  Met  Ser  Pro  Asp  Gly  His  Ile  Val  Glu  Arg  Ala  Asp  Lys  Ile
          115                       120                      125

Ser  Phe  His  Met  Leu  Phe  Asn  Pro  Trp  Cys  Arg  Asp  Met  Val  Tyr
     130                       135                      140

Leu  Pro  Asp  Glu  Ser  Lys  Leu  Gln  Glu  Tyr  Val  Met  Asn  Glu  Asp  Gly
145                       150                       155                      160

Val  Ile  Tyr  Met  Gly  Thr  Trp  Asp  Tyr  Ile  Arg  Ser  Ile  Pro  Trp  Asn
                    165                       170                      175

Tyr  Gly  Gln  Phe  Glu  Asp  Tyr  Val  Met  Asp  Ile  Cys  Phe  Glu  Val  Leu
               180                       185                      190

Asp  Asn  Ser  Pro  Ala  Ala  Leu  Lys  Asn  Ser  Glu  Met  Asp  Ile  Glu  His
               195                       200                      205

Arg  Ser  Asp  Pro  Val  Tyr  Val  Gly  Arg  Thr  Ile  Thr  Ala  Met  Val  Asn
     210                       215                       220

Ser  Asn  Gly  Asp  Arg  Gly  Val  Leu  Thr  Gly  Arg  Trp  Glu  Glu  Pro  Tyr
225                       230                       235                      240

Thr  Asp  Gly  Val  Ala  Pro  Tyr  Arg  Trp  Thr  Gly  Ser  Val  Pro  Ile  Leu
               245                       250                      255

Gln  Gln  Trp  Ser  Lys  Ala  Gly  Val  Arg  Pro  Val  Lys  Tyr  Gly  Gln  Cys
               260                       265                      270

Trp  Val  Phe  Ala  Ala  Val  Ala  Cys  Thr  Val  Leu  Arg  Cys  Leu  Gly  Ile
          275                       280                      285

Pro  Thr  Arg  Pro  Ile  Thr  Asn  Phe  Ala  Ser  Ala  His  Asp  Val  Asp  Gly
     290                       295                      300

Asn  Leu  Ser  Val  Asp  Phe  Leu  Leu  Asn  Glu  Arg  Leu  Glu  Ser  Leu  Asp
305                       310                       315                      320

Ser  Arg  Gln  Arg  Ser  Asp  Ser  Ser  Trp  Asn  Phe  His  Cys  Trp  Val  Glu
               325                       330                      335
```

| | | | | | | | | | | | | | |
|---|---|---|---|---|---|---|---|---|---|---|---|---|---|
| Ser | Trp | Met | Ser 340 | Arg | Glu | Asp | Leu | Pro 345 | Glu | Gly | Asn | Asp | Gly 350 | Trp | Gln |
| Val | Leu | Asp 355 | Pro | Thr | Pro | Gln | Glu 360 | Leu | Ser | Asp | Gly | Glu 365 | Phe | Cys | Cys |
| Gly | Pro 370 | Cys | Pro | Val | Ala | Ala 375 | Ile | Lys | Glu | Gly | Asn 380 | Leu | Gly | Val | Lys |
| Tyr 385 | Asp | Ala | Pro | Phe | Val 390 | Phe | Ala | Glu | Val | Asn 395 | Ala | Asp | Thr | Ile | Tyr 400 |
| Trp | Ile | Val | Gln | Lys 405 | Asp | Gly | Gln | Arg | Arg 410 | Lys | Ile | Thr | Glu | Asp 415 | His |
| Ala | Ser | Val | Gly 420 | Lys | Asn | Ile | Ser | Thr 425 | Lys | Ser | Val | Tyr | Gly 430 | Asn | His |
| Arg | Glu | Asp 435 | Val | Thr | Leu | His | Tyr 440 | Lys | Tyr | Pro | Glu | Gly 445 | Ser | Gln | Lys |
| Glu | Arg 450 | Glu | Val | Tyr | Lys | Lys 455 | Ala | Gly | Arg | Arg | Val 460 | Thr | Glu | Pro | Ser |
| Asn 465 | Glu | Ile | Ala | Glu | Gln 470 | Gly | Arg | Leu | Gln | Leu 475 | Ser | Ile | Lys | His | Ala 480 |
| Gln | Pro | Val | Phe | Gly 485 | Thr | Asp | Phe | Asp | Val 490 | Ile | Val | Glu | Val | Lys 495 | Asn |
| Glu | Gly | Gly | Arg 500 | Asp | Ala | His | Ala | Gln 505 | Leu | Thr | Met | Leu | Ala 510 | Met | Ala |
| Val | Thr | Tyr 515 | Asn | Ser | Leu | Arg | Arg 520 | Gly | Glu | Cys | Gln | Arg 525 | Lys | Thr | Ile |
| Ser | Val 530 | Thr | Val | Pro | Ala | His 535 | Lys | Ala | His | Lys | Glu 540 | Val | Met | Arg | Leu |
| His 545 | Tyr | Asp | Asp | Tyr | Val 550 | Arg | Cys | Val | Ser | Glu 555 | His | His | Leu | Ile | Arg 560 |
| Val | Lys | Ala | Leu | Leu 565 | Asp | Ala | Pro | Gly | Glu 570 | Asn | Gly | Pro | Ile | Met 575 | Thr |
| Val | Ala | Asn | Ile 580 | Pro | Leu | Ser | Thr | Pro 585 | Glu | Leu | Leu | Val | Gln 590 | Val | Pro |
| Gly | Lys | Ala 595 | Val | Val | Trp | Glu | Pro 600 | Leu | Thr | Ala | Tyr | Val 605 | Ser | Phe | Thr |
| Asn | Pro 610 | Leu | Pro | Val | Pro | Leu 615 | Lys | Gly | Gly | Val | Phe 620 | Thr | Leu | Glu | Gly |
| Ala 625 | Gly | Leu | Leu | Ser | Ala 630 | Thr | Gln | Ile | His | Val 635 | Asn | Gly | Ala | Val | Ala 640 |
| Pro | Ser | Gly | Lys | Val 645 | Ser | Val | Lys | Leu | Ser 650 | Phe | Ser | Pro | Met | Arg 655 | Thr |
| Gly | Val | Arg | Lys 660 | Leu | Leu | Val | Asp | Phe 665 | Asp | Ser | Asp | Arg | Leu 670 | Lys | Asp |
| Val | Lys | Gly 675 | Val | Thr | Thr | Val | Val 680 | Val | His | Lys | Lys | Tyr 685 | Arg | Ser | Leu |
| Ile | Thr 690 | Gly | Leu | His | Thr | Asp 695 | | | | | | | | | |

(2) INFORMATION FOR SEQ ID NO:7:

(i) SEQUENCE CHARACTERISTICS:
        (A) LENGTH: 2088 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
  (A) ORGANISM: Theragra chalcogramma
  (F) TISSUE TYPE: liver (ix) FEATURE:
  (A) NAME/KEY: CDS
  (B) LOCATION: 1..2085

(xi) SEQUENCE DESCRIPTION: SEQ ID NO:7:

| | | | | | | | | | | | | | | | | |
|---|---|---|---|---|---|---|---|---|---|---|---|---|---|---|---|---|
| GCC | CAC | ACA | AAC | CGT | TTA | ATT | GCT | GGT | GTT | GAT | CTG | AGA | AGC | CAG | GAA | 48 |
| Ala | His | Thr | Asn | Arg | Leu | Ile | Ala | Gly | Val | Asp | Leu | Arg | Ser | Gln | Glu | |
| 1 | | | | 5 | | | | | 10 | | | | | 15 | | |
| AAC | AAC | CGG | GAA | CAC | CGA | ACT | GAG | GAG | ATT | GAT | AGG | AAG | CGT | TTG | ATT | 96 |
| Asn | Asn | Arg | Glu | His | Arg | Thr | Glu | Glu | Ile | Asp | Arg | Lys | Arg | Leu | Ile | |
| | | | 20 | | | | | 25 | | | | | 30 | | | |
| GTT | CGG | CGG | GGA | CAA | GCC | TTC | TCC | CTG | ACG | GTG | CAC | CTC | TCC | GAC | CCG | 144 |
| Val | Arg | Arg | Gly | Gln | Ala | Phe | Ser | Leu | Thr | Val | His | Leu | Ser | Asp | Pro | |
| | | 35 | | | | | 40 | | | | | 45 | | | | |
| CTG | CAG | TCC | GGC | CAT | GAG | CTG | GCC | CTG | GTC | TTA | AAG | CAG | GAT | AAG | AAC | 192 |
| Leu | Gln | Ser | Gly | His | Glu | Leu | Ala | Leu | Val | Leu | Lys | Gln | Asp | Lys | Asn | |
| | 50 | | | | | 55 | | | | | 60 | | | | | |
| AAC | GAT | GAT | ATT | GTG | ATC | AGA | CAG | CGA | ACG | GCT | GGA | GGG | TCT | GGT | GAC | 240 |
| Asn | Asp | Asp | Ile | Val | Ile | Arg | Gln | Arg | Thr | Ala | Gly | Gly | Ser | Gly | Asp | |
| 65 | | | | | 70 | | | | | 75 | | | | | 80 | |
| AAG | TGG | TGG | TTA | CAC | CAG | CAG | AGC | GCG | AGG | AAC | GAA | TTA | CTG | CTG | ACT | 288 |
| Lys | Trp | Trp | Leu | His | Gln | Gln | Ser | Ala | Arg | Asn | Glu | Leu | Leu | Leu | Thr | |
| | | | | 85 | | | | | 90 | | | | | 95 | | |
| GTG | TAC | AGT | CCT | GCC | CGT | GCT | GCC | GTT | GGC | GAG | TAC | CGC | TTG | GCT | GTT | 336 |
| Val | Tyr | Ser | Pro | Ala | Arg | Ala | Ala | Val | Gly | Glu | Tyr | Arg | Leu | Ala | Val | |
| | | | 100 | | | | | 105 | | | | | 110 | | | |
| GAA | CTG | ATG | TCA | GGG | AAT | AAA | CTT | CTG | GAG | AGG | ACG | GAC | TTT | ACC | AAA | 384 |
| Glu | Leu | Met | Ser | Gly | Asn | Lys | Leu | Leu | Glu | Arg | Thr | Asp | Phe | Thr | Lys | |
| | | 115 | | | | | 120 | | | | | 125 | | | | |
| ATG | TAC | TTG | CTG | TTT | AAT | CCC | TGG | TGC | AAA | GAT | GAT | GCT | GTG | TAC | CTC | 432 |
| Met | Tyr | Leu | Leu | Phe | Asn | Pro | Trp | Cys | Lys | Asp | Asp | Ala | Val | Tyr | Leu | |
| | 130 | | | | | 135 | | | | | 140 | | | | | |
| CCT | GAT | GAA | AGT | CTG | CTC | AAG | GAA | TAC | ATT | ATG | AAC | GAG | AAT | GGT | CGC | 480 |
| Pro | Asp | Glu | Ser | Leu | Leu | Lys | Glu | Tyr | Ile | Met | Asn | Glu | Asn | Gly | Arg | |
| 145 | | | | | 150 | | | | | 155 | | | | | 160 | |
| ATT | TTC | ACT | GGG | AGT | GCG | GAT | TGG | ATG | AGT | GGG | TTG | CCA | TGG | AAT | TTC | 528 |
| Ile | Phe | Thr | Gly | Ser | Ala | Asp | Trp | Met | Ser | Gly | Leu | Pro | Trp | Asn | Phe | |
| | | | | 165 | | | | | 170 | | | | | 175 | | |
| GGA | CAG | TTT | GAA | GAC | AAT | GTG | ATG | GAC | ATC | TGC | TTT | GAG | ATC | CTT | GAC | 576 |
| Gly | Gln | Phe | Glu | Asp | Asn | Val | Met | Asp | Ile | Cys | Phe | Glu | Ile | Leu | Asp | |
| | | | 180 | | | | | 185 | | | | | 190 | | | |
| CGC | TTT | AAG | CCA | GCA | AGG | TCA | GAC | CCC | CCA | AAC | GAC | ATG | CGT | CAG | CGA | 624 |
| Arg | Phe | Lys | Pro | Ala | Arg | Ser | Asp | Pro | Pro | Asn | Asp | Met | Arg | Gln | Arg | |
| | | 195 | | | | | 200 | | | | | 205 | | | | |
| TGG | GAC | CCT | GTC | TAC | ATC | AGC | AGG | GCA | GTC | GTT | GCC | ATG | GTG | AAT | GCC | 672 |
| Trp | Asp | Pro | Val | Tyr | Ile | Ser | Arg | Ala | Val | Val | Ala | Met | Val | Asn | Ala | |
| | 210 | | | | | 215 | | | | | 220 | | | | | |
| AAC | GAT | GAC | GGT | GGA | GTC | TTG | GTG | GGG | AAA | TGG | CAG | GAA | CCT | TAC | ACA | 720 |
| Asn | Asp | Asp | Gly | Gly | Val | Leu | Val | Gly | Lys | Trp | Gln | Glu | Pro | Tyr | Thr | |
| 225 | | | | | 230 | | | | | 235 | | | | | 240 | |
| GGT | GGA | GTA | CAG | CCA | ACC | AAA | TGG | ATG | AGC | AGT | GTG | CCC | ATC | CTG | GAG | 768 |
| Gly | Gly | Val | Gln | Pro | Thr | Lys | Trp | Met | Ser | Ser | Val | Pro | Ile | Leu | Glu | |
| | | | | 245 | | | | | 250 | | | | | 255 | | |
| AAG | TGG | AGC | AAA | TCA | AAG | TCT | GGA | GTG | AAG | TAT | GGC | CAA | TGC | TGG | GTG | 816 |
| Lys | Trp | Ser | Lys | Ser | Lys | Ser | Gly | Val | Lys | Tyr | Gly | Gln | Cys | Trp | Val | |
| | | | 260 | | | | | 265 | | | | | 270 | | | |
| TTT | GCA | GCC | GTG | GCC | TGC | ACA | GTG | CTG | CGA | TGC | CTG | GGC | ATC | CCC | ACA | 864 |
| Phe | Ala | Ala | Val | Ala | Cys | Thr | Val | Leu | Arg | Cys | Leu | Gly | Ile | Pro | Thr | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 275 |     |     |     |     |     | 280 |     |     |     |     |     | 285 |     |      |
| CGC | TGC | ATC | ACC | AAC | TTT | GAG | TCA | GCC | CAT | GAC | ACA | GAC | GGA | AAC | CTC | 912  |
| Arg | Cys | Ile | Thr | Asn | Phe | Glu | Ser | Ala | His | Asp | Thr | Asp | Gly | Asn | Leu |      |
|     | 290 |     |     |     | 295 |     |     |     |     | 300 |     |     |     |     |     |      |
| TCC | ATC | GAC | CGA | GTG | TAC | AAC | ACA | CAT | AGG | CAG | AGT | GTT | AAC | CAT | GCT | 960  |
| Ser | Ile | Asp | Arg | Val | Tyr | Asn | Thr | His | Arg | Gln | Ser | Val | Asn | His | Ala |      |
| 305 |     |     |     | 310 |     |     |     |     | 315 |     |     |     |     |     | 320 |      |
| GAC | AGC | ATC | TGG | AAC | TTT | CAT | TGT | TGG | ATC | GAG | TCT | TAC | ATG | CAG | AGA | 1008 |
| Asp | Ser | Ile | Trp | Asn | Phe | His | Cys | Trp | Ile | Glu | Ser | Tyr | Met | Gln | Arg |      |
|     |     |     |     | 325 |     |     |     |     | 330 |     |     |     |     | 335 |     |      |
| GAA | GAT | CTA | CCT | GAA | GGA | TAT | GGT | GGC | TGG | CAA | GTC | TTG | GAC | CCC | ACA | 1056 |
| Glu | Asp | Leu | Pro | Glu | Gly | Tyr | Gly | Gly | Trp | Gln | Val | Leu | Asp | Pro | Thr |      |
|     |     |     | 340 |     |     |     |     | 345 |     |     |     |     | 350 |     |     |      |
| CCT | CAG | GAG | AGG | AGT | AGT | GGT | ATG | TTT | CGC | TGT | GGC | CCA | TGT | CCA | TTG | 1104 |
| Pro | Gln | Glu | Arg | Ser | Ser | Gly | Met | Phe | Arg | Cys | Gly | Pro | Cys | Pro | Leu |      |
|     |     | 355 |     |     |     |     | 360 |     |     |     |     | 365 |     |     |     |      |
| AAG | GCC | ATT | AAA | GAA | GGG | GAC | CTC | AAT | GTG | AAG | TTT | GAT | GTT | CCA | TTT | 1152 |
| Lys | Ala | Ile | Lys | Glu | Gly | Asp | Leu | Asn | Val | Lys | Phe | Asp | Val | Pro | Phe |      |
|     | 370 |     |     |     |     | 375 |     |     |     |     | 380 |     |     |     |     |      |
| GTC | TTT | GCT | GAG | GTG | AAT | GCA | GAC | ATC | ATC | AAT | TGG | GAA | ATC | AGA | CCA | 1200 |
| Val | Phe | Ala | Glu | Val | Asn | Ala | Asp | Ile | Ile | Asn | Trp | Glu | Ile | Arg | Pro |      |
| 385 |     |     |     |     | 390 |     |     |     |     | 395 |     |     |     |     | 400 |      |
| GAC | GGT | CAG | CGA | ATG | CGG | CTT | TCA | TCC | AAC | TCC | GCA | AAA | GTG | GGG | AGG | 1248 |
| Asp | Gly | Gln | Arg | Met | Arg | Leu | Ser | Ser | Asn | Ser | Ala | Lys | Val | Gly | Arg |      |
|     |     |     |     | 405 |     |     |     |     | 410 |     |     |     |     | 415 |     |      |
| AAC | ATT | AGC | ACC | AAA | AGT | CCT | TAC | AGT | AAC | GAG | AGG | GAA | GAT | ATA | ACC | 1296 |
| Asn | Ile | Ser | Thr | Lys | Ser | Pro | Tyr | Ser | Asn | Glu | Arg | Glu | Asp | Ile | Thr |      |
|     |     |     | 420 |     |     |     |     | 425 |     |     |     |     | 430 |     |     |      |
| CTT | CAG | TAC | AAG | TAC | CAA | GAA | GGT | TCA | GCC | AAG | GAG | CGG | GAG | GTG | TAC | 1344 |
| Leu | Gln | Tyr | Lys | Tyr | Gln | Glu | Gly | Ser | Ala | Lys | Glu | Arg | Glu | Val | Tyr |      |
|     |     | 435 |     |     |     |     | 440 |     |     |     |     | 445 |     |     |     |      |
| AAC | AAG | GCA | GGG | CGG | CGC | ATC | TCC | GGG | CCG | GAT | AGA | GAA | GAG | GAA | TCA | 1392 |
| Asn | Lys | Ala | Gly | Arg | Arg | Ile | Ser | Gly | Pro | Asp | Arg | Glu | Glu | Glu | Ser |      |
|     | 450 |     |     |     |     | 455 |     |     |     |     | 460 |     |     |     |     |      |
| AAA | CCA | GCC | AAT | GAA | CCA | GGA | AAC | GTG | CAG | CTG | GAG | ATC | AGA | TAC | GCC | 1440 |
| Lys | Pro | Ala | Asn | Glu | Pro | Gly | Asn | Val | Gln | Leu | Glu | Ile | Arg | Tyr | Ala |      |
| 465 |     |     |     |     | 470 |     |     |     |     | 475 |     |     |     |     | 480 |      |
| AAG | CCT | GTG | TTC | GGG | ACC | GAC | TTT | GAC | GTC | ATC | TTT | GAG | TTG | GAG | AAC | 1488 |
| Lys | Pro | Val | Phe | Gly | Thr | Asp | Phe | Asp | Val | Ile | Phe | Glu | Leu | Glu | Asn |      |
|     |     |     |     | 485 |     |     |     |     | 490 |     |     |     |     | 495 |     |      |
| ATG | GGA | GAC | GAA | GAA | GTC | AGC | TGC | AAA | TTG | AAC | ATG | ATG | TCA | AAG | GCT | 1536 |
| Met | Gly | Asp | Glu | Glu | Val | Ser | Cys | Lys | Leu | Asn | Met | Met | Ser | Lys | Ala |      |
|     |     |     | 500 |     |     |     |     | 505 |     |     |     |     | 510 |     |     |      |
| GTC | ACG | TAT | AAC | TCG | GTC | CAC | CTG | GGA | GAG | TGC | CAG | AAT | AGC | ACA | GTC | 1584 |
| Val | Thr | Tyr | Asn | Ser | Val | His | Leu | Gly | Glu | Cys | Gln | Asn | Ser | Thr | Val |      |
|     |     | 515 |     |     |     |     | 520 |     |     |     |     | 525 |     |     |     |      |
| AAT | GTT | GTC | ATT | CCT | GCT | CAC | AAA | GTC | CAC | AGG | GAG | ACG | GTG | CGT | CTA | 1632 |
| Asn | Val | Val | Ile | Pro | Ala | His | Lys | Val | His | Arg | Glu | Thr | Val | Arg | Leu |      |
|     | 530 |     |     |     |     | 535 |     |     |     |     | 540 |     |     |     |     |      |
| CTC | TAC | ACT | AAG | TAT | GCA | TCG | TGC | GTC | AGC | GAA | CAC | AAC | ATC | ATC | CGG | 1680 |
| Leu | Tyr | Thr | Lys | Tyr | Ala | Ser | Cys | Val | Ser | Glu | His | Asn | Ile | Ile | Arg |      |
| 545 |     |     |     |     | 550 |     |     |     |     | 555 |     |     |     |     | 560 |      |
| GTG | GTA | GGG | GTG | GCA | AGA | GTG | TCC | GGC | CAG | GAA | AAA | TCC | ATC | CTG | GAG | 1728 |
| Val | Val | Gly | Val | Ala | Arg | Val | Ser | Gly | Gln | Glu | Lys | Ser | Ile | Leu | Glu |      |
|     |     |     |     | 565 |     |     |     |     | 570 |     |     |     |     | 575 |     |      |
| ATG | GTC | AAC | ATC | CCA | CTG | AGC | AAG | CCC | AAA | CTC | AGT | ATT | AAG | GTT | CCT | 1776 |
| Met | Val | Asn | Ile | Pro | Leu | Ser | Lys | Pro | Lys | Leu | Ser | Ile | Lys | Val | Pro |      |
|     |     |     | 580 |     |     |     |     | 585 |     |     |     |     | 590 |     |     |      |
| GGC | TGG | GTG | ATT | TTA | AAT | AGG | AAA | ATC | ACC | ACC | GTC | ATC | ACC | TTC | ACC | 1824 |
| Gly | Trp | Val | Ile | Leu | Asn | Arg | Lys | Ile | Thr | Thr | Val | Ile | Thr | Phe | Thr |      |

|  |  |  |  |  |  |  |  |  |  |  |  |  |  |  |  |
|---|---|---|---|---|---|---|---|---|---|---|---|---|---|---|---|
|  |  |  | 595 |  |  |  | 600 |  |  |  | 605 |  |  |  |  |
| AAT | CCA | TTG | CCA | GTG | CCA | CTG | AAC | CGA | GGA | GTG | TTC | ACT | GTT | GAA | GGG | 1872 |
| Asn | Pro | Leu | Pro | Val | Pro | Leu | Asn | Arg | Gly | Val | Phe | Thr | Val | Glu | Gly |
| 610 |  |  |  |  | 615 |  |  |  |  | 620 |  |  |  |  |  |
| GCT | GGC | CTA | CTT | TCA | ACC | AAA | GAG | ATC | CGC | ATT | TCT | GGT | AGC | ATC | GCT | 1920 |
| Ala | Gly | Leu | Leu | Ser | Thr | Lys | Glu | Ile | Arg | Ile | Ser | Gly | Ser | Ile | Ala |
| 625 |  |  |  |  | 630 |  |  |  |  | 635 |  |  |  |  | 640 |
| CCA | GGC | CAG | CGT | GTG | TCT | GTG | GAG | CTG | TCC | TTC | ACA | CCC | ATG | AGG | GCG | 1968 |
| Pro | Gly | Gln | Arg | Val | Ser | Val | Glu | Leu | Ser | Phe | Thr | Pro | Met | Arg | Ala |
|  |  |  |  | 645 |  |  |  |  | 650 |  |  |  |  | 655 |  |
| GGG | GTC | AGG | GAG | TTC | CTG | GTG | GAC | TTT | GAC | TCC | GAC | AGG | CTC | CAG | GAC | 2016 |
| Gly | Val | Arg | Glu | Phe | Leu | Val | Asp | Phe | Asp | Ser | Asp | Arg | Leu | Gln | Asp |
|  |  |  | 660 |  |  |  |  | 665 |  |  |  |  | 670 |  |  |
| GTG | AAG | GGA | GTC | GCC | ACA | CTG | GTG | GTC | CGC | AAG | ACT | TCA | CCC | TCC | TAT | 2064 |
| Val | Lys | Gly | Val | Ala | Thr | Leu | Val | Val | Arg | Lys | Thr | Ser | Pro | Ser | Tyr |
|  |  | 675 |  |  |  |  | 680 |  |  |  |  | 685 |  |  |  |
| TTT | CCC | ATG | CCC | TAC | ACG | TTG | TGA |  |  |  |  |  |  |  |  | 2088 |
| Phe | Pro | Met | Pro | Tyr | Thr | Leu |  |  |  |  |  |  |  |  |  |
| 690 |  |  |  |  |  | 695 |  |  |  |  |  |  |  |  |  |

( 2 ) INFORMATION FOR SEQ ID NO:8:

( i ) SEQUENCE CHARACTERISTICS:
        ( A ) LENGTH: 695 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| Ala | His | Thr | Asn | Arg | Leu | Ile | Ala | Gly | Val | Asp | Leu | Arg | Ser | Gln | Glu |
|---|---|---|---|---|---|---|---|---|---|---|---|---|---|---|---|
| 1 |  |  |  | 5 |  |  |  |  | 10 |  |  |  |  | 15 |  |
| Asn | Asn | Arg | Glu | His | Arg | Thr | Glu | Glu | Ile | Asp | Arg | Lys | Arg | Leu | Ile |
|  |  |  | 20 |  |  |  |  | 25 |  |  |  |  | 30 |  |  |
| Val | Arg | Arg | Gly | Gln | Ala | Phe | Ser | Leu | Thr | Val | His | Leu | Ser | Asp | Pro |
|  |  | 35 |  |  |  |  | 40 |  |  |  |  | 45 |  |  |  |
| Leu | Gln | Ser | Gly | His | Glu | Leu | Ala | Leu | Val | Leu | Lys | Gln | Asp | Lys | Asn |
|  | 50 |  |  |  |  | 55 |  |  |  |  | 60 |  |  |  |  |
| Asn | Asp | Asp | Ile | Val | Ile | Arg | Gln | Arg | Thr | Ala | Gly | Gly | Ser | Gly | Asp |
| 65 |  |  |  |  | 70 |  |  |  |  | 75 |  |  |  |  | 80 |
| Lys | Trp | Trp | Leu | His | Gln | Gln | Ser | Ala | Arg | Asn | Glu | Leu | Leu | Leu | Thr |
|  |  |  |  | 85 |  |  |  |  | 90 |  |  |  |  | 95 |  |
| Val | Tyr | Ser | Pro | Ala | Arg | Ala | Ala | Val | Gly | Glu | Tyr | Arg | Leu | Ala | Val |
|  |  |  | 100 |  |  |  |  | 105 |  |  |  |  | 110 |  |  |
| Glu | Leu | Met | Ser | Gly | Asn | Lys | Leu | Leu | Glu | Arg | Thr | Asp | Phe | Thr | Lys |
|  |  | 115 |  |  |  |  | 120 |  |  |  |  | 125 |  |  |  |
| Met | Tyr | Leu | Leu | Phe | Asn | Pro | Trp | Cys | Lys | Asp | Ala | Val | Tyr | Leu |  |
| 130 |  |  |  |  | 135 |  |  |  |  | 140 |  |  |  |  |  |
| Pro | Asp | Glu | Ser | Leu | Leu | Lys | Glu | Tyr | Ile | Met | Asn | Glu | Asn | Gly | Arg |
| 145 |  |  |  |  | 150 |  |  |  |  | 155 |  |  |  |  | 160 |
| Ile | Phe | Thr | Gly | Ser | Ala | Asp | Trp | Met | Ser | Gly | Leu | Pro | Trp | Asn | Phe |
|  |  |  |  | 165 |  |  |  |  | 170 |  |  |  |  | 175 |  |
| Gly | Gln | Phe | Glu | Asp | Asn | Val | Met | Asp | Ile | Cys | Phe | Glu | Ile | Leu | Asp |
|  |  |  | 180 |  |  |  |  | 185 |  |  |  |  | 190 |  |  |
| Arg | Phe | Lys | Pro | Ala | Arg | Ser | Asp | Pro | Asn | Asp | Met | Arg | Gln | Arg |  |
|  |  | 195 |  |  |  |  | 200 |  |  |  |  | 205 |  |  |  |
| Trp | Asp | Pro | Val | Tyr | Ile | Ser | Arg | Ala | Val | Val | Ala | Met | Val | Asn | Ala |
| 210 |  |  |  |  | 215 |  |  |  |  | 220 |  |  |  |  |  |

| | | | | | | | | | | | | | | |
|---|---|---|---|---|---|---|---|---|---|---|---|---|---|---|
| Asn 225 | Asp | Asp | Gly | Gly | Val 230 | Leu | Val | Gly | Lys | Trp 235 | Gln | Glu | Pro | Tyr | Thr 240 |
| Gly | Gly | Val | Gln | Pro 245 | Thr | Lys | Trp | Met | Ser 250 | Ser | Val | Pro | Ile | Leu 255 | Glu |
| Lys | Trp | Ser | Lys 260 | Ser | Lys | Ser | Gly | Val 265 | Lys | Tyr | Gly | Gln | Cys 270 | Trp | Val |
| Phe | Ala | Ala 275 | Val | Ala | Cys | Thr | Val 280 | Leu | Arg | Cys | Leu | Gly 285 | Ile | Pro | Thr |
| Arg | Cys 290 | Ile | Thr | Asn | Phe | Glu 295 | Ser | Ala | His | Asp | Thr 300 | Asp | Gly | Asn | Leu |
| Ser 305 | Ile | Asp | Arg | Val | Tyr 310 | Asn | Thr | His | Arg | Gln 315 | Ser | Val | Asn | His | Ala 320 |
| Asp | Ser | Ile | Trp | Asn 325 | Phe | His | Cys | Trp | Ile 330 | Glu | Ser | Tyr | Met | Gln 335 | Arg |
| Glu | Asp | Leu | Pro 340 | Glu | Gly | Tyr | Gly | Trp 345 | Gln | Val | Leu | Asp 350 | Pro | Thr |
| Pro | Gln | Glu | Arg 355 | Ser | Ser | Gly | Met 360 | Phe | Arg | Cys | Gly | Pro 365 | Cys | Pro | Leu |
| Lys | Ala 370 | Ile | Lys | Glu | Gly | Asp 375 | Leu | Asn | Val | Lys | Phe 380 | Asp | Val | Pro | Phe |
| Val 385 | Phe | Ala | Glu | Val | Asn 390 | Ala | Asp | Ile | Ile | Asn 395 | Trp | Glu | Ile | Arg | Pro 400 |
| Asp | Gly | Gln | Arg | Met 405 | Arg | Leu | Ser | Ser | Asn 410 | Ser | Ala | Lys | Val | Gly 415 | Arg |
| Asn | Ile | Ser | Thr 420 | Lys | Ser | Pro | Tyr | Ser 425 | Asn | Glu | Arg | Glu | Asp 430 | Ile | Thr |
| Leu | Gln | Tyr | Lys 435 | Tyr | Gln | Glu | Gly | Ser 440 | Ala | Lys | Glu | Arg 445 | Glu | Val | Tyr |
| Asn | Lys 450 | Ala | Gly | Arg | Arg | Ile 455 | Ser | Gly | Pro | Asp | Arg 460 | Glu | Glu | Glu | Ser |
| Lys 465 | Pro | Ala | Asn | Glu | Pro 470 | Gly | Asn | Val | Gln | Leu 475 | Glu | Ile | Arg | Tyr | Ala 480 |
| Lys | Pro | Val | Phe | Gly 485 | Thr | Asp | Phe | Asp | Val 490 | Ile | Phe | Glu | Leu | Glu 495 | Asn |
| Met | Gly | Asp | Glu 500 | Glu | Val | Ser | Cys | Lys 505 | Leu | Asn | Met | Met | Ser 510 | Lys | Ala |
| Val | Thr | Tyr 515 | Asn | Ser | Val | His | Leu 520 | Gly | Glu | Cys | Gln | Asn 525 | Ser | Thr | Val |
| Asn | Val 530 | Val | Ile | Pro | Ala | His 535 | Lys | Val | His | Arg | Glu 540 | Thr | Val | Arg | Leu |
| Leu 545 | Tyr | Thr | Lys | Tyr | Ala 550 | Ser | Cys | Val | Ser | Glu 555 | His | Asn | Ile | Ile | Arg 560 |
| Val | Val | Gly | Val | Ala 565 | Arg | Val | Ser | Gly | Gln 570 | Glu | Lys | Ser | Ile | Leu 575 | Glu |
| Met | Val | Asn | Ile 580 | Pro | Leu | Ser | Lys | Pro 585 | Lys | Leu | Ser | Ile | Lys 590 | Val | Pro |
| Gly | Trp | Val 595 | Ile | Leu | Asn | Arg | Lys 600 | Ile | Thr | Thr | Val | Ile 605 | Thr | Phe | Thr |
| Asn | Pro 610 | Leu | Pro | Val | Pro | Leu 615 | Asn | Arg | Gly | Val | Phe 620 | Thr | Val | Glu | Gly |
| Ala 625 | Gly | Leu | Leu | Ser | Thr 630 | Lys | Glu | Ile | Arg | Ile 635 | Ser | Gly | Ser | Ile | Ala 640 |
| Pro | Gly | Gln | Arg | Val 645 | Ser | Val | Glu | Leu | Ser 650 | Phe | Thr | Pro | Met | Arg 655 | Ala |

```
Gly  Val  Arg  Glu  Phe  Leu  Val  Asp  Phe  Asp  Ser  Asp  Arg  Leu  Gln  Asp
               660                      665                      670

Val  Lys  Gly  Val  Ala  Thr  Leu  Val  Arg  Lys  Thr  Ser  Pro  Ser  Tyr
          675                     680                     685

Phe  Pro  Met  Pro  Tyr  Thr  Leu
     690                     695
```

( 2 ) INFORMATION FOR SEQ ID NO:9:

( i ) SEQUENCE CHARACTERISTICS:
        ( A ) LENGTH: 2921 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: Theragra chalcogramma
        ( F ) TISSUE TYPE: liver ( i x ) FEATURE:
        ( A ) NAME/KEY: CDS
        ( B ) LOCATION: 32..2122

( x i ) SEQUENCE DESCRIPTION: SEQ ID NO:9:

```
AGCAACTCTT  GGAAAGAATT  TAGCAAAGAT  A  ATG  GCC  CAC  ACA  AAC  CGT  TTA                52
                                       Met  Ala  His  Thr  Asn  Arg  Leu
                                        1                     5

ATT  GCT  GGT  GTT  GAT  CTG  AGA  AGC  CAG  GAA  AAC  AAC  CGG  GAA  CAC  CGA         100
Ile  Ala  Gly  Val  Asp  Leu  Arg  Ser  Gln  Glu  Asn  Asn  Arg  Glu  His  Arg
               10                     15                     20

ACT  GAG  GAG  ATT  GAT  AGG  AAG  CGT  TTG  ATT  GTT  CGG  CGG  GGA  CAA  GCC         148
Thr  Glu  Glu  Ile  Asp  Arg  Lys  Arg  Leu  Ile  Val  Arg  Arg  Gly  Gln  Ala
     25                     30                     35

TTC  TCC  CTG  ACG  GTG  CAC  CTC  TCC  GAC  CCG  CTG  CAG  TCC  GGC  CAT  GAG         196
Phe  Ser  Leu  Thr  Val  His  Leu  Ser  Asp  Pro  Leu  Gln  Ser  Gly  His  Glu
40                       45                     50                          55

CTG  GCC  CTG  GTC  TTA  AAG  CAG  GAT  AAG  AAC  AAC  GAT  GAT  ATT  GTG  ATC         244
Leu  Ala  Leu  Val  Leu  Lys  Gln  Asp  Lys  Asn  Asn  Asp  Asp  Ile  Val  Ile
               60                     65                     70

AGA  CAG  CGA  ACG  GCT  GGA  GGG  TCT  GGT  GAC  AAG  TGG  TGG  TTA  CAC  CAG         292
Arg  Gln  Arg  Thr  Ala  Gly  Gly  Ser  Gly  Asp  Lys  Trp  Trp  Leu  His  Gln
Arg            75                     80                     85

CAG  AGC  GCG  AGG  AAC  GAA  TTA  CTG  CTG  ACT  GTG  TAC  AGT  CCT  GCC  CGT         340
Gln  Ser  Ala  Arg  Asn  Glu  Leu  Leu  Leu  Thr  Val  Tyr  Ser  Pro  Ala  Arg
          90                     95                     100

GCT  GCC  GTT  GGC  GAG  TAC  CGC  TTG  GCT  GTT  GAA  CTG  ATG  TCA  GGG  AAT         388
Ala  Ala  Val  Gly  Glu  Tyr  Arg  Leu  Ala  Val  Glu  Leu  Met  Ser  Gly  Asn
     105                     110                     115

AAA  CTT  CTG  GAG  AGG  ACG  GAC  TTT  ACC  AAA  ATG  TAC  TTG  CTG  TTT  AAT         436
Lys  Leu  Leu  Glu  Arg  Thr  Asp  Phe  Thr  Lys  Met  Tyr  Leu  Leu  Phe  Asn
120                      125                     130                         135

CCC  TGG  TGC  AAA  GAT  GAT  GCT  GTG  TAC  CTC  CCT  GAT  GAA  AGT  CTG  CTC         484
Pro  Trp  Cys  Lys  Asp  Asp  Ala  Val  Tyr  Leu  Pro  Asp  Glu  Ser  Leu  Leu
               140                    145                     150

AAG  GAA  TAC  ATT  ATG  AAC  GAG  AAT  GGT  CGC  ATT  TTC  ACT  GGG  AGT  GCG         532
Lys  Glu  Tyr  Ile  Met  Asn  Glu  Asn  Gly  Arg  Ile  Phe  Thr  Gly  Ser  Ala
          155                    160                     165

GAT  TGG  ATG  AGT  GGG  TTG  CCA  TGG  AAT  TTC  GGA  CAG  TTT  GAA  GAC  AAT         580
Asp  Trp  Met  Ser  Gly  Leu  Pro  Trp  Asn  Phe  Gly  Gln  Phe  Glu  Asp  Asn
     170                     175                     180

GTG  ATG  GAC  ATC  TGC  TTT  GAG  ATC  CTT  GAC  CGC  TTT  AAG  CCA  GCA  AGG         628
```

| | | | | | | | | | | | | | | |
|---|---|---|---|---|---|---|---|---|---|---|---|---|---|---|
| Val | Met | Asp | Ile | Cys | Phe | Glu | Ile | Leu | Asp | Arg | Phe | Lys | Pro | Ala | Arg |
| | 185 | | | | 190 | | | | | 195 | | | | |

| TCA | GAC | CCC | CCA | AAC | GAC | ATG | CGT | CAG | CGA | TGG | GAC | CCT | GTC | TAC | ATC | 676 |
|---|---|---|---|---|---|---|---|---|---|---|---|---|---|---|---|---|
| Ser | Asp | Pro | Pro | Asn | Asp | Met | Arg | Gln | Arg | Trp | Asp | Pro | Val | Tyr | Ile | |
| 200 | | | | | 205 | | | | | 210 | | | | | 215 | |

| AGC | AGG | GCA | GTC | GTT | GCC | ATG | GTG | AAT | GCC | AAC | GAT | GAC | GGT | GGA | GTC | 724 |
|---|---|---|---|---|---|---|---|---|---|---|---|---|---|---|---|---|
| Ser | Arg | Ala | Val | Val | Ala | Met | Val | Asn | Ala | Asn | Asp | Asp | Gly | Gly | Val | |
| | | | | 220 | | | | | 225 | | | | | 230 | | |

| TTG | GTG | GGG | AAA | TGG | CAG | GAA | CCT | TAC | ACA | GGT | GGA | GTA | CAG | CCA | ACC | 772 |
|---|---|---|---|---|---|---|---|---|---|---|---|---|---|---|---|---|
| Leu | Val | Gly | Lys | Trp | Gln | Glu | Pro | Tyr | Thr | Gly | Gly | Val | Gln | Pro | Thr | |
| | | | | 235 | | | | | 240 | | | | | 245 | | |

| AAA | TGG | ATG | AGC | AGT | GTG | CCC | ATC | CTG | GAG | AAG | TGG | AGC | AAA | TCA | AAG | 820 |
|---|---|---|---|---|---|---|---|---|---|---|---|---|---|---|---|---|
| Lys | Trp | Met | Ser | Ser | Val | Pro | Ile | Leu | Glu | Lys | Trp | Ser | Lys | Ser | Lys | |
| | | | 250 | | | | | 255 | | | | | 260 | | | |

| TCT | GGA | GTG | AAG | TAT | GGC | CAA | TGC | TGG | GTG | TTT | GCA | GCC | GTG | GCC | TGC | 868 |
|---|---|---|---|---|---|---|---|---|---|---|---|---|---|---|---|---|
| Ser | Gly | Val | Lys | Tyr | Gly | Gln | Cys | Trp | Val | Phe | Ala | Ala | Val | Ala | Cys | |
| | | | 265 | | | | | 270 | | | | | 275 | | | |

| ACA | GTG | CTG | CGA | TGC | CTG | GGC | ATC | CCC | ACA | CGC | TGC | ATC | ACC | AAC | TTT | 916 |
|---|---|---|---|---|---|---|---|---|---|---|---|---|---|---|---|---|
| Thr | Val | Leu | Arg | Cys | Leu | Gly | Ile | Pro | Thr | Arg | Cys | Ile | Thr | Asn | Phe | |
| 280 | | | | | 285 | | | | | 290 | | | | | 295 | |

| GAG | TCA | GCC | CAT | GAC | ACA | GAC | GGA | AAC | CTC | TCC | ATC | GAC | CGA | GTG | TAC | 964 |
|---|---|---|---|---|---|---|---|---|---|---|---|---|---|---|---|---|
| Glu | Ser | Ala | His | Asp | Thr | Asp | Gly | Asn | Leu | Ser | Ile | Asp | Arg | Val | Tyr | |
| | | | | 300 | | | | | 305 | | | | | 310 | | |

| AAC | ACA | CAT | AGG | CAG | AGT | GTT | AAC | CAT | GCT | GAC | AGC | ATC | TGG | AAC | TTT | 1012 |
|---|---|---|---|---|---|---|---|---|---|---|---|---|---|---|---|---|
| Asn | Thr | His | Arg | Gln | Ser | Val | Asn | His | Ala | Asp | Ser | Ile | Trp | Asn | Phe | |
| | | | 315 | | | | | 320 | | | | | 325 | | | |

| CAT | TGT | TGG | ATC | GAG | TCT | TAC | ATG | CAG | AGA | GAA | GAT | CTA | CCT | GAA | GGA | 1060 |
|---|---|---|---|---|---|---|---|---|---|---|---|---|---|---|---|---|
| His | Cys | Trp | Ile | Glu | Ser | Tyr | Met | Gln | Arg | Glu | Asp | Leu | Pro | Glu | Gly | |
| | | | 330 | | | | | 335 | | | | | 340 | | | |

| TAT | GGT | GGC | TGG | CAA | GTC | TTG | GAC | CCC | ACA | CCT | CAG | GAG | AGG | AGT | AGT | 1108 |
|---|---|---|---|---|---|---|---|---|---|---|---|---|---|---|---|---|
| Tyr | Gly | Gly | Trp | Gln | Val | Leu | Asp | Pro | Thr | Pro | Gln | Glu | Arg | Ser | Ser | |
| | 345 | | | | | 350 | | | | | 355 | | | | | |

| GGT | ATG | TTT | CGC | TGT | GGC | CCA | TGT | CCA | TTG | AAG | GCC | ATT | AAA | GAA | GGG | 1156 |
|---|---|---|---|---|---|---|---|---|---|---|---|---|---|---|---|---|
| Gly | Met | Phe | Arg | Cys | Gly | Pro | Cys | Pro | Leu | Lys | Ala | Ile | Lys | Glu | Gly | |
| 360 | | | | | 365 | | | | | 370 | | | | | 375 | |

| GAC | CTC | AAT | GTG | AAG | TTT | GAT | GTT | CCA | TTT | GTC | TTT | GCT | GAG | GTG | AAT | 1204 |
|---|---|---|---|---|---|---|---|---|---|---|---|---|---|---|---|---|
| Asp | Leu | Asn | Val | Lys | Phe | Asp | Val | Pro | Phe | Val | Phe | Ala | Glu | Val | Asn | |
| | | | | 380 | | | | | 385 | | | | | 390 | | |

| GCA | GAC | ATC | ATC | AAT | TGG | GAA | ATC | AGA | CCA | GAC | GGT | CAG | CGA | ATG | CGG | 1252 |
|---|---|---|---|---|---|---|---|---|---|---|---|---|---|---|---|---|
| Ala | Asp | Ile | Ile | Asn | Trp | Glu | Ile | Arg | Pro | Asp | Gly | Gln | Arg | Met | Arg | |
| | | | 395 | | | | | 400 | | | | | 405 | | | |

| CTT | TCA | TCC | AAC | TCC | GCA | AAA | GTG | GGG | AGG | AAC | ATT | AGC | ACC | AAA | AGT | 1300 |
|---|---|---|---|---|---|---|---|---|---|---|---|---|---|---|---|---|
| Leu | Ser | Ser | Asn | Ser | Ala | Lys | Val | Gly | Arg | Asn | Ile | Ser | Thr | Lys | Ser | |
| | | 410 | | | | | 415 | | | | | 420 | | | | |

| CCT | TAC | AGT | AAC | GAG | AGG | GAA | GAT | ATA | ACC | CTT | CAG | TAC | AAG | TAC | CAA | 1348 |
|---|---|---|---|---|---|---|---|---|---|---|---|---|---|---|---|---|
| Pro | Tyr | Ser | Asn | Glu | Arg | Glu | Asp | Ile | Thr | Leu | Gln | Tyr | Lys | Tyr | Gln | |
| | 425 | | | | | 430 | | | | | 435 | | | | | |

| GAA | GGT | TCA | GCC | AAG | GAG | CGG | GAG | GTG | TAC | AAC | AAG | GCA | GGG | CGG | CGC | 1396 |
|---|---|---|---|---|---|---|---|---|---|---|---|---|---|---|---|---|
| Glu | Gly | Ser | Ala | Lys | Glu | Arg | Glu | Val | Tyr | Asn | Lys | Ala | Gly | Arg | Arg | |
| 440 | | | | | 445 | | | | | 450 | | | | | 455 | |

| ATC | TCC | GGG | CCG | GAT | AGA | GAA | GAG | GAA | TCA | AAA | CCA | GCC | AAT | GAA | CCA | 1444 |
|---|---|---|---|---|---|---|---|---|---|---|---|---|---|---|---|---|
| Ile | Ser | Gly | Pro | Asp | Arg | Glu | Glu | Glu | Ser | Lys | Pro | Ala | Asn | Glu | Pro | |
| | | | | 460 | | | | | 465 | | | | | 470 | | |

| GGA | AAC | GTG | CAG | CTG | GAG | ATC | AGA | TAC | GCC | AAG | CCT | GTG | TTC | GGG | ACC | 1492 |
|---|---|---|---|---|---|---|---|---|---|---|---|---|---|---|---|---|
| Gly | Asn | Val | Gln | Leu | Glu | Ile | Arg | Tyr | Ala | Lys | Pro | Val | Phe | Gly | Thr | |
| | | | 475 | | | | | 480 | | | | | 485 | | | |

| GAC | TTT | GAC | GTC | ATC | TTT | GAG | TTG | GAG | AAC | ATG | GGA | GAC | GAA | GAA | GTC | 1540 |
|---|---|---|---|---|---|---|---|---|---|---|---|---|---|---|---|---|
| Asp | Phe | Asp | Val | Ile | Phe | Glu | Leu | Glu | Asn | Met | Gly | Asp | Glu | Glu | Val | |
| | | 490 | | | | | 495 | | | | | 500 | | | | |

| AGC | TGC | AAA | TTG | AAC | ATG | ATG | TCA | AAG | GCT | GTC | ACG | TAT | AAC | TCG | GTC | 1588 |

-continued

| | | | | | | | | | | | | | | | | |
|---|---|---|---|---|---|---|---|---|---|---|---|---|---|---|---|---|
| Ser | Cys 505 | Lys | Leu | Asn | Met | Met 510 | Ser | Lys | Ala | Val | Thr 515 | Tyr | Asn | Ser | Val | |
| CAC His 520 | CTG Leu | GGA Gly | GAG Glu | TGC Cys | CAG Gln 525 | AAT Asn | AGC Ser | ACA Thr | GTC Val | AAT Asn 530 | GTT Val | GTC Val | ATT Ile | CCT Pro | GCT Ala 535 | 1636 |
| CAC His | AAA Lys | GTC Val | CAC His | AGG Arg 540 | GAG Glu | ACG Thr | GTG Val | CGT Arg | CTA Leu | CTC Leu 545 | TAC Tyr | ACT Thr | AAG Lys | TAT Tyr 550 | GCA Ala | 1684 |
| TCG Ser | TGC Cys | GTC Val | AGC Ser 555 | GAA Glu | CAC His | AAC Asn | ATC Ile | ATC Ile | CGG Arg 560 | GTG Val | GTA Val | GGG Gly | GTG Val 565 | GCA Ala | AGA Arg | 1732 |
| GTG Val | TCC Ser | GGC Gly 570 | CAG Gln | GAA Glu | AAA Lys | TCC Ser | ATC Ile 575 | CTG Leu | GAG Glu | ATG Met | GTC Val | AAC Asn 580 | ATC Ile | CCA Pro | CTG Leu | 1780 |
| AGC Ser | AAG Lys 585 | CCC Pro | AAA Lys | CTC Leu | AGT Ser | ATT Ile 590 | AAG Lys | GTT Val | CCT Pro | GGC Gly | TGG Trp 595 | GTG Val | ATT Ile | TTA Leu | AAT Asn | 1828 |
| AGG Arg 600 | AAA Lys | ATC Ile | ACC Thr | ACC Thr | GTC Val 605 | ATC Ile | ACC Thr | TTC Phe | ACC Thr | AAT Asn 610 | CCA Pro | TTG Leu | CCA Pro | GTG Val | CCA Pro 615 | 1876 |
| CTG Leu | AAC Asn | CGA Arg | GGA Gly | GTG Val 620 | TTC Phe | ACT Thr | GTT Val | GAA Glu | GGG Gly 625 | GCT Ala | GGC Gly | CTA Leu | CTT Leu | TCA Ser 630 | ACC Thr | 1924 |
| AAA Lys | GAG Glu | ATC Ile | CGC Arg 635 | ATT Ile | TCT Ser | GGT Gly | AGC Ser | ATC Ile 640 | GCT Ala | CCA Pro | GGC Gly | CAG Gln | CGT Arg 645 | GTG Val | TCT Ser | 1972 |
| GTG Val | GAG Glu | CTG Leu 650 | TCC Ser | TTC Phe | ACA Thr | CCC Pro | ATG Met 655 | AGG Arg | GCG Ala | GGG Gly | GTC Val | AGG Arg 660 | GAG Glu | TTC Phe | CTG Leu | 2020 |
| GTG Val | GAC Asp 665 | TTT Phe | GAC Asp | TCC Ser | GAC Asp | AGG Arg 670 | CTC Leu | CAG Gln | GAC Asp | GTG Val | AAG Lys 675 | GGA Gly | GTC Val | GCC Ala | ACA Thr | 2068 |
| CTG Leu 680 | GTG Val | GTC Val | CGC Arg | AAG Lys | ACT Thr 685 | TCA Ser | CCC Pro | TCC Ser | TAT Tyr | TTT Phe 690 | CCC Pro | ATG Met | CCC Pro | TAC Tyr | ACG Thr 695 | 2116 |
| TTG Leu | TGATCAAACC | | TATAGCTGTC | | AACAGGGCTC | | TGGCACTCAT | | TCTTATACTA | | | | | | | 2169 |

| | | | | |
|---|---|---|---|---|
| ACAAATATAT | TTAGCAAAGT | CAAGCAAGGG. | TTTCACTTTT | CTTAATATAC | CATGATGTGT | 2229 |
| AGCGCTGATT | CAATTAATGA | ATAAATTAAT | TCAATTAAT | GTGAAGAAAA | TGCAAACATT | 2289 |
| GCCTTAATTC | TTTGCAATGT | CACAGGAATA | GCGTAAATCA | TGGCTCATTG | ATATTAAATG | 2349 |
| TAGTATTGAC | ATATATCCAT | GCATTTTGCA | CTTCTGCAAA | TCACCATTTT | GTTGTTAATC | 2409 |
| AATGTTTTAC | CACGATTTTT | GCATCTATTC | TTGTTTAATT | GTAATCAAGA | CATTTACATG | 2469 |
| ATTGTGGGGG | CCAAAGTATA | TAGATGTTGT | GGTTGGGAAA | TGGGGCAATA | ATAGGGGAAG | 2529 |
| GGTTAATTAT | AGGGTCAGTG | TTAGTAATTG | GTTAAGGTTA | CTAATAGGGT | AAGTGTTACA | 2589 |
| GTGTAAAGAT | AAGCCTTTGA | TTTTGTTAAA | TTTATTATGC | CTTTCATCAA | CAGTGGTTTG | 2649 |
| GGGTTTTATA | ACAACAATTA | AAGTGCTTAA | CTACTGGTGA | ACGACGTTGC | AGAACGTATA | 2709 |
| TGGTACAAGT | TTGTGTTGAT | CGCATGGAAA | AGGGAATAAC | CAGTTACAAC | TTATATGGTA | 2769 |
| AGAGCCTGGT | AATACCATGG | AAACAAACGA | GGCTTCCTTT | TACAGTACAG | TTTCAGCGTC | 2829 |
| ATGAATATTT | GGCCTGTTAA | GCCCTTTGAG | ACTGTAATGG | TGATTAAGGG | CTATACAAAT | 2889 |
| AAAATTGAAT | TGAATTGAAT | TAAAAAAAAA | AA | | | 2921 |

( 2 ) INFORMATION FOR SEQ ID NO:10:

( i ) SEQUENCE CHARACTERISTICS:

( A ) LENGTH: 696 amino acids
( B ) TYPE: amino acid
( D ) TOPOLOGY: linear ( i i ) MOLECULE TYPE: protein ( x i ) SEQUENCE DESCRIPTION: SEQ ID NO:10:

| Met | Ala | His | Thr | Asn | Arg | Leu | Ile | Ala | Gly | Val | Asp | Leu | Arg | Ser | Gln |
|---|---|---|---|---|---|---|---|---|---|---|---|---|---|---|---|
| 1 | | | | 5 | | | | | 10 | | | | | 15 | |
| Glu | Asn | Asn | Arg | Glu | His | Arg | Thr | Glu | Glu | Ile | Asp | Arg | Lys | Arg | Leu |
| | | | 20 | | | | | 25 | | | | | 30 | | |
| Ile | Val | Arg | Arg | Gly | Gln | Ala | Phe | Ser | Leu | Thr | Val | His | Leu | Ser | Asp |
| | | | 35 | | | | 40 | | | | | 45 | | | |
| Pro | Leu | Gln | Ser | Gly | His | Glu | Leu | Ala | Leu | Val | Leu | Lys | Gln | Asp | Lys |
| | | 50 | | | | 55 | | | | | 60 | | | | |
| Asn | Asn | Asp | Asp | Ile | Val | Ile | Arg | Gln | Arg | Thr | Ala | Gly | Gly | Ser | Gly |
| 65 | | | | | 70 | | | | | 75 | | | | | 80 |
| Asp | Lys | Trp | Trp | Leu | His | Gln | Gln | Ser | Ala | Arg | Asn | Glu | Leu | Leu | Leu |
| | | | | 85 | | | | | 90 | | | | | 95 | |
| Thr | Val | Tyr | Ser | Pro | Ala | Arg | Ala | Ala | Val | Gly | Glu | Tyr | Arg | Leu | Ala |
| | | | | 100 | | | | | 105 | | | | | 110 | |
| Val | Glu | Leu | Met | Ser | Gly | Asn | Lys | Leu | Leu | Glu | Arg | Thr | Asp | Phe | Thr |
| | | | | 115 | | | | | 120 | | | | 125 | | |
| Lys | Met | Tyr | Leu | Leu | Phe | Asn | Pro | Trp | Cys | Lys | Asp | Asp | Ala | Val | Tyr |
| | 130 | | | | | 135 | | | | | 140 | | | | |
| Leu | Pro | Asp | Glu | Ser | Leu | Leu | Lys | Glu | Tyr | Ile | Met | Asn | Glu | Asn | Gly |
| 145 | | | | | 150 | | | | | 155 | | | | | 160 |
| Arg | Ile | Phe | Thr | Gly | Ser | Ala | Asp | Trp | Met | Ser | Gly | Leu | Pro | Trp | Asn |
| | | | | 165 | | | | | 170 | | | | | 175 | |
| Phe | Gly | Gln | Phe | Glu | Asp | Asn | Val | Met | Asp | Ile | Cys | Phe | Glu | Ile | Leu |
| | | | 180 | | | | | 185 | | | | | 190 | | |
| Asp | Arg | Phe | Lys | Pro | Ala | Arg | Ser | Asp | Pro | Pro | Asn | Asp | Met | Arg | Gln |
| | | | 195 | | | | 200 | | | | | 205 | | | |
| Arg | Trp | Asp | Pro | Val | Tyr | Ile | Ser | Arg | Ala | Val | Val | Ala | Met | Val | Asn |
| | 210 | | | | | 215 | | | | | 220 | | | | |
| Ala | Asn | Asp | Asp | Gly | Gly | Val | Leu | Val | Gly | Lys | Trp | Gln | Glu | Pro | Tyr |
| 225 | | | | | 230 | | | | | 235 | | | | | 240 |
| Thr | Gly | Gly | Val | Gln | Pro | Thr | Lys | Trp | Met | Ser | Ser | Val | Pro | Ile | Leu |
| | | | | 245 | | | | | 250 | | | | | 255 | |
| Glu | Lys | Trp | Ser | Lys | Ser | Lys | Ser | Gly | Val | Lys | Tyr | Gly | Gln | Cys | Trp |
| | | | 260 | | | | | 265 | | | | | 270 | | |
| Val | Phe | Ala | Ala | Val | Ala | Cys | Thr | Val | Leu | Arg | Cys | Leu | Gly | Ile | Pro |
| | | 275 | | | | | 280 | | | | | 285 | | | |
| Thr | Arg | Cys | Ile | Thr | Asn | Phe | Glu | Ser | Ala | His | Asp | Thr | Asp | Gly | Asn |
| | 290 | | | | | 295 | | | | | 300 | | | | |
| Leu | Ser | Ile | Asp | Arg | Val | Tyr | Asn | Thr | His | Arg | Gln | Ser | Val | Asn | His |
| 305 | | | | | 310 | | | | | 315 | | | | | 320 |
| Ala | Asp | Ser | Ile | Trp | Asn | Phe | His | Cys | Trp | Ile | Glu | Ser | Tyr | Met | Gln |
| | | | | 325 | | | | | 330 | | | | | 335 | |
| Arg | Glu | Asp | Leu | Pro | Glu | Gly | Tyr | Gly | Gly | Trp | Gln | Val | Leu | Asp | Pro |
| | | | 340 | | | | | 345 | | | | | 350 | | |
| Thr | Pro | Gln | Glu | Arg | Ser | Ser | Gly | Met | Phe | Arg | Cys | Gly | Pro | Cys | Pro |
| | | 355 | | | | | 360 | | | | | 365 | | | |
| Leu | Lys | Ala | Ile | Lys | Glu | Gly | Asp | Leu | Asn | Val | Lys | Phe | Asp | Val | Pro |
| | 370 | | | | | 375 | | | | | 380 | | | | |

| | | | | | | | | | | | | | | |
|---|---|---|---|---|---|---|---|---|---|---|---|---|---|---|
| Phe<br>385 | Val | Phe | Ala | Glu | Val<br>390 | Asn | Ala | Asp | Ile | Ile<br>395 | Asn | Trp | Glu | Ile | Arg<br>400 |
| Pro | Asp | Gly | Gln | Arg<br>405 | Met | Arg | Leu | Ser | Ser<br>410 | Asn | Ser | Ala | Lys | Val<br>415 | Gly |
| Arg | Asn | Ile | Ser<br>420 | Thr | Lys | Ser | Pro | Tyr<br>425 | Ser | Asn | Glu | Arg | Glu<br>430 | Asp | Ile |
| Thr | Leu | Gln<br>435 | Tyr | Lys | Tyr | Gln | Glu<br>440 | Gly | Ser | Ala | Lys | Glu<br>445 | Arg | Glu | Val |
| Tyr | Asn<br>450 | Lys | Ala | Gly | Arg | Arg<br>455 | Ile | Ser | Gly | Pro | Asp<br>460 | Arg | Glu | Glu | Glu |
| Ser<br>465 | Lys | Pro | Ala | Asn | Glu<br>470 | Pro | Gly | Asn | Val | Gln<br>475 | Leu | Glu | Ile | Arg | Tyr<br>480 |
| Ala | Lys | Pro | Val | Phe<br>485 | Gly | Thr | Asp | Phe | Asp<br>490 | Val | Ile | Phe | Glu | Leu<br>495 | Glu |
| Asn | Met | Gly | Asp<br>500 | Glu | Glu | Val | Ser | Cys<br>505 | Lys | Leu | Asn | Met | Met<br>510 | Ser | Lys |
| Ala | Val | Thr<br>515 | Tyr | Asn | Ser | Val | His<br>520 | Leu | Gly | Glu | Cys | Gln<br>525 | Asn | Ser | Thr |
| Val | Asn<br>530 | Val | Val | Ile | Pro | Ala<br>535 | His | Lys | Val | His | Arg<br>540 | Glu | Thr | Val | Arg |
| Leu<br>545 | Leu | Tyr | Thr | Lys | Tyr<br>550 | Ala | Ser | Cys | Val | Ser<br>555 | Glu | His | Asn | Ile | Ile<br>560 |
| Arg | Val | Val | Gly | Val<br>565 | Ala | Arg | Val | Ser | Gly<br>570 | Gln | Glu | Lys | Ser | Ile<br>575 | Leu |
| Glu | Met | Val | Asn<br>580 | Ile | Pro | Leu | Ser | Lys<br>585 | Pro | Lys | Leu | Ser | Ile<br>590 | Lys | Val |
| Pro | Gly | Trp<br>595 | Val | Ile | Leu | Asn | Arg<br>600 | Lys | Ile | Thr | Thr | Val<br>605 | Ile | Thr | Phe |
| Thr | Asn<br>610 | Pro | Leu | Pro | Val | Pro<br>615 | Leu | Asn | Arg | Gly | Val<br>620 | Phe | Thr | Val | Glu |
| Gly<br>625 | Ala | Gly | Leu | Leu | Ser<br>630 | Thr | Lys | Glu | Ile | Arg<br>635 | Ile | Ser | Gly | Ser | Ile<br>640 |
| Ala | Pro | Gly | Gln | Arg<br>645 | Val | Ser | Val | Glu | Leu<br>650 | Ser | Phe | Thr | Pro | Met<br>655 | Arg |
| Ala | Gly | Val | Arg<br>660 | Glu | Phe | Leu | Val | Asp<br>665 | Phe | Asp | Ser | Asp | Arg<br>670 | Leu | Gln |
| Asp | Val | Lys<br>675 | Gly | Val | Ala | Thr | Leu<br>680 | Val | Val | Arg | Lys | Thr<br>685 | Ser | Pro | Ser |
| Tyr | Phe<br>690 | Pro | Met | Pro | Tyr | Thr<br>695 | Leu | | | | | | | | |

( 2 ) INFORMATION FOR SEQ ID NO:11:

( i ) SEQUENCE CHARACTERISTICS:
    ( A ) LENGTH: 29 base pairs
    ( B ) TYPE: nucleic acid
    ( C ) STRANDEDNESS: unknown
    ( D ) TOPOLOGY: linear ( i i ) MOLECULE TYPE: DNA (genomic)

( x i ) SEQUENCE DESCRIPTION: SEQ ID NO:11:

GTCAAGTACG GCCAGTGCTG GGTCTTCGC    29

( 2 ) INFORMATION FOR SEQ ID NO:12:

( i ) SEQUENCE CHARACTERISTICS:
    ( A ) LENGTH: 30 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:12:

AATTCATCGA TTAGTAAGGA GGTTTAAAAT     30

(2) INFORMATION FOR SEQ ID NO:13:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:13:

GGCTTCTTAT AAAGGTCTGA TTGTTGATGT     30

(2) INFORMATION FOR SEQ ID NO:14:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:14:

TAATGGTCGT TCTCATGAAA ACAACCTGGC AC     32

(2) INFORMATION FOR SEQ ID NO:15:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:15:

ATCGTACGCG TGAAATCGAC CGTGAGCGCC TGA     33

(2) INFORMATION FOR SEQ ID NO:16:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:16:

AGCCATTTTA AACCTCCTTA CTAATCGATG     30

(2) INFORMATION FOR SEQ ID NO:17:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

( x i ) SEQUENCE DESCRIPTION: SEQ ID NO:17:

ATTAACATCA ACAATCAGAC CTTTATAAGA 30

( 2 ) INFORMATION FOR SEQ ID NO:18:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

CGATGTGCCA GGTTGTTTTC ATGAGAACGA CC 32

( 2 ) INFORMATION FOR SEQ ID NO:19:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

AGCTTCAGGC GCTCACGGTC GATTTCACGC GTA 33

( 2 ) INFORMATION FOR SEQ ID NO:20:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Pagrus major
        ( F ) TISSUE TYPE: liver ( x i ) SEQUENCE DESCRIPTION: SEQ ID NO:20:

Val Lys Tyr Gly Gln Cys Trp Val Phe Ala Ala Val Ala Cys Thr Val
1                 5                       10                      15

Leu Arg Cys Leu Gly Ile Pro Thr Arg
                 20                       25

( 2 ) INFORMATION FOR SEQ ID NO:21:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

TTGGAAGCTT GTAAGAGCAA CTCTTGGAAA 30

( 2 ) INFORMATION FOR SEQ ID NO:22:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

TTGTACACTC GATCGATGGA GAGGT 25

( 2 ) INFORMATION FOR SEQ ID NO:23:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

TCTGCTTTGG GATCCTTGAC CGCT 24

( 2 ) INFORMATION FOR SEQ ID NO:24:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

TGAAGGAGAG CTCCACAGAC ACA 23

( 2 ) INFORMATION FOR SEQ ID NO:25:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

ATGATGTCAA AGGCTGTCAC 20

( 2 ) INFORMATION FOR SEQ ID NO:26:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

TCTTACCATA TAAGTTGTAA 20

( 2 ) INFORMATION FOR SEQ ID NO:27:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

( 2 ) INFORMATION FOR SEQ ID NO:28:

( i ) SEQUENCE CHARACTERISTICS:
        ( A ) LENGTH: 1921 base pairs
        ( B ) TYPE: nucleic acid
        ( C ) STRANDEDNESS: unknown
        ( D ) TOPOLOGY: unknown ( i i ) MOLECULE TYPE: DNA (genomic)

( v i ) ORIGINAL SOURCE:
        ( A ) ORGANISM: Theragra chalcogramma
        ( F ) TISSUE TYPE: muscle ( x i ) SEQUENCE DESCRIPTION: SEQ ID NO:28:

```
ATTGATTAAC AACAAAATGG                                                    20

GCCCACACAA ACCGTTTAAT TGCTGGTGTT GATCTGAGAA GCCAGGAAAA CAACCGGGAA         60
CACCGAACTG AGGAGATTGA TAGGAAGCGT TTGATTGTTC GGCGGGGACA AGCCTTCTCC       120
CTGACGGTGC ACCTCTCCGA CCCGCTGCAG TCCGGCCATG AGCTGGCCCT GGTCTTAAAG       180
CAGGATAAAA TCAACGATGA TATTGTGATC AGACAGCGAA CGACTGGAGG GTCCGGTGAC       240
AAGTGGTGGT TACACCAGCA GAGCGCGAAC AACGAATTAC TGCTGACTGT GTACAGTCCC       300
GCCCGTGCTG CCGTTGGCGA GTACCGCTTG GCTGTTGAAC TGATGTCAGG GAATAAACTT       360
CTGGAGAGGA CGGACTTTAC CAAAATGTAC TTGCTGTTTA ATCCCTGGTG CAAAGAAGAT       420
GCCGTGTACC TCCCTGATGA GTGTCTGCTC AAGGAATACA TTATGAACGA GAATGGTCGC       480
ATTTTCACTG GGAGTGCGGA TTGGATGAGT GGGTTGCCAT GGAATTTCGG ACAGTTTGAA       540
GATAATGTGA TGGACATCTG CTTTGAGATC CTTGACCGCT TAACCCAGC GAGGTCAGAC        600
CCCCCAAGCG ACATGCTTCA GCGATGGGAC CCTGTCTACA TCAGCAGGGC AGTCGTTGCC       660
ATGGTGAATG CCAACGATGA TGACGGTGGA GTCGTGGTGG GTCGATGGCA GGAACCTTAC       720
ACAGGTGGAG TACAGCCAAC CAAATGGATG AGCAGTGTGC CCATCCTGGA AGAGTGGAGC       780
AAATCAAAGT CTGGAGTGAA ATATGGCCAA TGCTGGGTGT TTGCAGCCGT GGCCTGCACA       840
GTGATGCGAT GCCTGGGCAT CCCCACACGC TGCATCACCA ACTTTCAGTC GGCCCATGAC       900
ACAGACGGAA ACCTCTCCAT CGACCGAGTG TACAACATAC ATAGGCAGCT AGTTGACGGT       960
GATGACAGTA TCTGGAACTT TCATTGTTGG ATCGAGTCTT ACATGCAGAG AGAAGATCTA      1020
CCTGAAGGAT ATGGTGGCTG GCAAGTCTTG GACCCCACAC CTCAGGAGAG GAGTAGTGGT      1080
ATGTTTCGCT GTGGCCCATG TCCTTTGAAG GCCATTAAAG AAGGGGACCT CAATGTGAAG      1140
TTTGATGTTC CATTTGTCTT TGCTGAGGTG AATGCAGACA TCATCAATTG GAAATCAGA       1200
CCAGACGGTC AGCGAAAGCG GCTTTCATCC AACTCTGCAA ATGTGGGGAG GAACATTAGC      1260
ACCAAAAGTC CTTATGGTAA CGAGAGGGAA GATATAACCC ATCAGTACAA GTACCAAGAA      1320
GGTTCAGCCA AGGAGCGGGA GGTGTACAAC AAGGCAGGGC GGCGCATCTC CGGGCCGGAT      1380
GGAGAAGAGG AATCAAAACC AGGAAACGTG CAGCTGGAGA TCAAGCACGC CAAACCTGTG      1440
TTCGGGACCG ACTTTGACGT CATCTTTGAG TTGGAGAACA TGGGAGACAA AGAAGTCAGC      1500
TGCAAATTAA ACATGATGTC AGAGGCTGTC ACCTATAACT CAGTTCACCT TGGACGGTTC      1560
CAGAACAGCA CGGTCAATGT TGTCATTCCT GCTCACAAAG TCCACAGTGA GACGGTGCGT      1620
CTACTCTACA CTAAGTATGC CTCAGTTGTC AGCGAGCACA ACATCATCCG GGTGACAGGG      1680
GTGGCGGAAG TGTCCGGCCA GGAAAAATCC ATCCTGGAGA TGGTCAACAT CCCACTGAGC      1740
AAGCCCAAAC TCAGTATTAA GGTTCCTGGC TGGGTGATTT TAAATAGGAA AATCACCACC      1800
TTCATCTCCT TCACCAATCC ATTGCCAGTG CCACTGAACC GAGGAGTGTT CACTGTTGAA      1860
```

```
                                                       5,607,849
                        73                                                          74
                                                    -continued GGGGCTGGCC TACTTCCCAC CAAAGAGATC CGCATTTCTG GTAGCATCGC TCCAGGCCAG                    1920

C                                                                                   1921

( 2 ) INFORMATION FOR SEQ ID NO:29:

( i ) SEQUENCE CHARACTERISTICS:
                ( A ) LENGTH: 19 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:29:

ACACTGCCGG TCCATCGAA                                                                  19

( 2 ) INFORMATION FOR SEQ ID NO:30:

( i ) SEQUENCE CHARACTERISTICS:
                ( A ) LENGTH: 2064 base pairs
                ( B ) TYPE: nucleic acid
                ( C ) STRANDEDNESS: double
                ( D ) TOPOLOGY: linear ( i i ) MOLECULE TYPE: cDNA to mRNA ( v i ) ORIGINAL SOURCE:
                ( A ) ORGANISM: Paralichthys olivaceus
                ( F ) TISSUE TYPE: liver ( i x ) FEATURE:
                ( A ) NAME/KEY: CDS
                ( B ) LOCATION: 1..2061

( x i ) SEQUENCE DESCRIPTION: SEQ ID NO:30:
```

```
GAC  AAT  CAG  AAC  ATT  CCG  ATC  ACT  GAT  GTG  GAT  GTG  AGA  AGT  CAT  GAA        48
Asp  Asn  Gln  Asn  Ile  Pro  Ile  Thr  Asp  Val  Asp  Val  Arg  Ser  His  Glu
 1              5                        10                       15

AAC  AAC  TTG  GCT  CAC  CGC  ACC  AGG  GAG  ATT  GAT  CGG  GAG  CGC  TTG  ATC        96
Asn  Asn  Leu  Ala  His  Arg  Thr  Arg  Glu  Ile  Asp  Arg  Glu  Arg  Leu  Ile
              20                       25                       30

GTC  CGC  AGG  GGT  CAA  CCC  TTC  TCC  ATA  TCT  CTG  CAG  TGC  TGC  GAC  TCG       144
Val  Arg  Arg  Gly  Gln  Pro  Phe  Ser  Ile  Ser  Leu  Gln  Cys  Cys  Asp  Ser
         35                       40                       45

CTG  ACC  CGG  AAT  CAC  CAT  CTG  GAA  CTG  TCC  CTG  CAC  CTC  GGT  AAG  AAA       192
Leu  Thr  Arg  Asn  His  His  Leu  Glu  Leu  Ser  Leu  His  Leu  Gly  Lys  Lys
     50                       55                       60

GAT  GAG  GTG  GTG  ATT  AAG  GTG  CAC  AAT  GAG  CCT  GAG  GCT  GGA  GGC  AAG       240
Asp  Glu  Val  Val  Ile  Lys  Val  His  Asn  Glu  Pro  Glu  Ala  Gly  Gly  Lys
65                       70                       75                       80

TGG  TGG  TTT  AAC  CAT  CAG  AAA  GTG  CAG  GAT  GAA  ATT  CTG  CTG  ACT  CTA       288
Trp  Trp  Phe  Asn  His  Gln  Lys  Val  Gln  Asp  Glu  Ile  Leu  Leu  Thr  Leu
                     85                       90                       95

CAC  AGT  CCA  GCG  GAC  GCC  ATA  ATT  GGC  GAG  TAC  CAC  CTG  ACT  GTG  TTG       336
His  Ser  Pro  Ala  Asp  Ala  Ile  Ile  Gly  Glu  Tyr  His  Leu  Thr  Val  Leu
               100                      105                      110

ATC  AAG  TCA  CCG  GAT  GGA  CAC  TTT  GTG  AAG  AAG  ACT  AAG  AAC  ATT  GGA       384
Ile  Lys  Ser  Pro  Asp  Gly  His  Phe  Val  Lys  Lys  Thr  Lys  Asn  Ile  Gly
          115                      120                      125

TTC  CAC  CTG  CTC  TTT  AAC  CCC  TGG  TGC  AAA  GAT  GAT  GCT  GTG  TAC  CTC       432
Phe  His  Leu  Leu  Phe  Asn  Pro  Trp  Cys  Lys  Asp  Asp  Ala  Val  Tyr  Leu
     130                      135                      140

CCT  GAT  GAA  AGG  ATG  CTC  GAC  GAG  TAT  GTT  ATG  AAT  GAG  GAG  GGG  ATC       480
Pro  Asp  Glu  Arg  Met  Leu  Asp  Glu  Tyr  Val  Met  Asn  Glu  Glu  Gly  Ile
145                      150                      155                      160
```

| | | | | | | | | | | | | | | | | |
|---|---|---|---|---|---|---|---|---|---|---|---|---|---|---|---|---|
| ATT | TAC | AGG | GGA | ACC | TCG | AAT | CAC | ATC | AGT | AGC | ATA | CCC | TGG | AAT | TAC | 528 |
| Ile | Tyr | Arg | Gly | Thr 165 | Ser | Asn | His | Ile | Ser 170 | Ser | Ile | Pro | Trp | Asn 175 | Tyr | |
| GGA | CAG | TTT | GAG | GAC | TAT | GTG | ATG | GAC | ATC | TGT | TTT | CAA | GTT | CTG | GAC | 576 |
| Gly | Gln | Phe | Glu 180 | Asp | Tyr | Val | Met | Asp 185 | Ile | Cys | Phe | Gln | Val 190 | Leu | Asp | |
| AAC | TCC | AAG | GAA | GCC | CTG | AAG | AAT | TCA | AAG | ATG | GAC | ATT | GAG | AAG | AGA | 624 |
| Asn | Ser | Lys 195 | Glu | Ala | Leu | Lys | Asn 200 | Ser | Lys | Met | Asp | Ile 205 | Glu | Lys | Arg | |
| TCT | GAC | CCT | GTC | TAT | GTC | AGC | AGG | ATG | ATC | ACT | GCG | ATG | GTG | AAC | TCT | 672 |
| Ser | Asp 210 | Pro | Val | Tyr | Val | Ser 215 | Arg | Met | Ile | Thr | Ala 220 | Met | Val | Asn | Ser | |
| AAC | GGT | GAC | AGG | GGT | GTG | CTG | ACT | GGT | CAG | TGG | CAC | GAG | CCA | TAC | ACT | 720 |
| Asn 225 | Gly | Asp | Arg | Gly | Val 230 | Leu | Thr | Gly | Gln | Trp 235 | His | Glu | Pro | Tyr | Thr 240 | |
| GGC | GGG | TTC | TCA | CCA | CTT | CGA | TGG | ACC | GGC | AGC | GTG | CCC | ATC | CTC | CGG | 768 |
| Gly | Gly | Phe | Ser | Pro 245 | Leu | Arg | Trp | Thr | Gly 250 | Ser | Val | Pro | Ile | Leu 255 | Arg | |
| AAG | TGG | AGC | AAG | GCC | GAG | GTC | AGG | GCG | GTC | AAA | TAT | GGC | CAG | TGC | TGG | 816 |
| Lys | Trp | Ser | Lys 260 | Ala | Glu | Val | Arg | Ala 265 | Val | Lys | Tyr | Gly | Gln 270 | Cys | Trp | |
| GTG | TTT | GCT | GCT | GTC | GCC | TGC | ACA | GTG | CTG | CGT | TGT | CTG | GGA | ATC | CCA | 864 |
| Val | Phe | Ala 275 | Ala | Val | Ala | Cys | Thr 280 | Val | Leu | Arg | Cys | Leu 285 | Gly | Ile | Pro | |
| ACA | CGC | AAC | ATC | ACT | AAC | TTC | AAT | TCA | GCA | CAT | GAT | GTC | GAT | GGA | AAC | 912 |
| Thr | Arg 290 | Asn | Ile | Thr | Asn | Phe 295 | Asn | Ser | Ala | His | Asp 300 | Val | Asp | Gly | Asn | |
| CTC | TCC | GTC | GAC | ATC | GTG | TTG | AAC | AAA | GAA | ATG | GAG | AGC | GTT | GGC | AAG | 960 |
| Leu 305 | Ser | Val | Asp | Ile | Val 310 | Leu | Asn | Lys | Glu | Met 315 | Glu | Ser | Val | Gly | Lys 320 | |
| AAG | GAC | AGT | AGC | TGG | AAC | TTC | CAC | TGT | TGG | ATC | GAG | TCC | TGG | ATG | AGG | 1008 |
| Lys | Asp | Ser | Ser | Trp 325 | Asn | Phe | His | Cys | Trp 330 | Ile | Glu | Ser | Trp | Met 335 | Arg | |
| AGA | GAC | GAC | CTC | TCT | AAA | GGA | AAT | GAC | GGC | TGG | CAG | GTT | TTG | GAC | CCC | 1056 |
| Arg | Asp | Asp | Leu 340 | Ser | Lys | Gly | Asn | Asp 345 | Gly | Trp | Gln | Val | Leu 350 | Asp | Pro | |
| ACC | CCT | CAA | GAA | CTG | AGT | GAT | GGT | GAG | TAT | TGC | TGC | GGC | CCG | TGT | CCA | 1104 |
| Thr | Pro | Gln 355 | Glu | Leu | Ser | Asp | Gly 360 | Glu | Tyr | Cys | Cys | Gly 365 | Pro | Cys | Pro | |
| GTC | ACC | GCC | ATC | AAG | GAG | GGA | AAT | CTG | AGT | GTG | AAG | TAC | GAC | GCT | CCG | 1152 |
| Val | Thr | Ala 370 | Ile | Lys | Glu | Gly | Asn 375 | Leu | Ser | Val | Lys | Tyr 380 | Asp | Ala | Pro | |
| TTT | ATC | TTC | GCT | GAG | GTG | AAC | GCT | GAC | ATC | ATC | TAC | TGG | ATG | GCT | GGA | 1200 |
| Phe 385 | Ile | Phe | Ala | Glu | Val 390 | Asn | Ala | Asp | Ile | Ile 395 | Tyr | Trp | Met | Ala | Gly 400 | |
| CCA | GGA | GGC | GAA | CGG | AAG | AAG | ATC | GAT | GTG | GAC | CAG | AGT | GGT | GTG | GGG | 1248 |
| Pro | Gly | Gly | Glu | Arg 405 | Lys | Lys | Ile | Asp | Val 410 | Asp | Gln | Ser | Gly | Val 415 | Gly | |
| AAG | AAC | ATC | AGC | ACC | AAA | AGT | CTT | TAT | GGC | GAC | TAC | AGG | GAG | GAT | GTC | 1296 |
| Lys | Asn | Ile | Ser 420 | Thr | Lys | Ser | Leu | Tyr 425 | Gly | Asp | Tyr | Arg | Glu 430 | Asp | Val | |
| ACT | CTG | CAC | TAC | AAA | TAC | CCC | GAA | GGC | TCC | AAG | AAG | GAG | AGA | GAG | GTG | 1344 |
| Thr | Leu | His 435 | Tyr | Lys | Tyr | Pro | Glu 440 | Gly | Ser | Lys | Lys | Glu 445 | Arg | Glu | Val | |
| TAC | CAG | AAG | GCC | GGA | CAC | CGA | ATC | AAA | GAG | CAG | ATC | TGT | GAA | AAC | AAA | 1392 |
| Tyr | Gln | Lys 450 | Ala | Gly | His | Arg | Ile 455 | Lys | Glu | Gln | Ile | Cys 460 | Glu | Asn | Lys | |
| GGT | CCA | CAA | CAA | CTG | CAG | CTG | TCA | GTC | AAG | CAC | GGG | AAA | CCT | GTA | TTT | 1440 |
| Gly 465 | Pro | Gln | Gln | Leu | Gln 470 | Leu | Ser | Val | Lys | His 475 | Gly | Lys | Pro | Val | Phe 480 | |

| | | | | | | | | | | | | | | | | |
|---|---|---|---|---|---|---|---|---|---|---|---|---|---|---|---|---|
| GGC | ACT | GAC | TTC | GAT | GTG | ATA | GTT | GAG | GTG | AAG | AAT | GAA | GGA | CAG | AAA | 1488 |
| Gly | Thr | Asp | Phe | Asp 485 | Val | Ile | Val | Glu | Val 490 | Lys | Asn | Glu | Gly | Gln 495 | Lys | |
| GAC | ACC | AGT | CCA | CAG | CTG | CTG | ATT | GTG | GTC | ATG | GCC | GTG | ACC | TAC | AAT | 1536 |
| Asp | Thr | Ser | Pro 500 | Gln | Leu | Leu | Ile | Val 505 | Val | Met | Ala | Val | Thr 510 | Tyr | Asn | |
| TCC | ATC | AAT | CAA | GGG | GAG | TGT | CAG | AGG | AAG | GCG | ACC | ATA | GTG | ACC | GTG | 1584 |
| Ser | Ile | Asn 515 | Gln | Gly | Glu | Cys | Gln 520 | Arg | Lys | Ala | Thr | Ile 525 | Val | Thr | Val | |
| CCG | GCT | CGC | AAA | ACC | CAC | AAG | GAA | GTG | CTG | CGT | CTG | CGC | TAC | GAC | GAC | 1632 |
| Pro | Ala 530 | Arg | Lys | Thr | His | Lys 535 | Glu | Val | Leu | Arg | Leu 540 | Arg | Tyr | Asp | Asp | |
| TAT | GTC | AAA | TGT | GTC | TCT | GAG | CAC | CAT | CTG | ATC | AGG | GTG | AAA | GCG | CTC | 1680 |
| Tyr 545 | Val | Lys | Cys | Val | Ser 550 | Glu | His | His | Leu | Ile 555 | Arg | Val | Lys | Ala | Leu 560 | |
| ATG | GAG | GTT | CCA | GGG | GAC | AAC | AAA | CCC | GTC | ATG | AGT | GTG | GCC | AAC | ATT | 1728 |
| Met | Glu | Val | Pro | Gly 565 | Asp | Asn | Lys | Pro | Val 570 | Met | Ser | Val | Ala | Asn 575 | Ile | |
| CCA | CTG | AGC | ATG | CCT | GAG | CTC | CTG | GTA | GAG | GTA | CCT | GGG | AGC | ATC | ATT | 1776 |
| Pro | Leu | Ser | Met 580 | Pro | Glu | Leu | Leu | Val 585 | Glu | Val | Pro | Gly | Ser 590 | Ile | Ile | |
| GTT | CAG | GAG | AAG | GTG | ACA | GCC | TTC | ATC | TCC | TTC | ACA | AAT | CCT | CTA | ACT | 1824 |
| Val | Gln | Glu 595 | Lys | Val | Thr | Ala | Phe 600 | Ile | Ser | Phe | Thr | Asn 605 | Pro | Leu | Thr | |
| GTC | CCA | CTG | AAG | CGT | GGC | ATG | TTC | ACC | GTT | GAG | GGG | TCC | GGA | CTA | CTG | 1872 |
| Val | Pro 610 | Leu | Lys | Arg | Gly | Met 615 | Phe | Thr | Val | Glu | Gly 620 | Ser | Gly | Leu | Leu | |
| TCT | GCC | TCT | GAG | ATC | TAT | GTG | AAA | GGG | GAC | ATT | GCT | CCA | GGC | CAG | AAG | 1920 |
| Ser | Ala | Ser 625 | Glu | Ile | Tyr | Val 630 | Lys | Gly | Asp | Ile | Ala 635 | Pro | Gly | Gln | Lys 640 | |
| GTT | TCT | GTC | AAG | ATC | ACC | TTC | ACG | CCC | ATG | AGG | GTC | GGG | GTG | AGG | AAG | 1968 |
| Val | Ser | Val | Lys | Ile 645 | Thr | Phe | Thr | Pro | Met 650 | Arg | Val | Gly | Val | Arg 655 | Lys | |
| CTC | CTG | GTG | GAC | TTT | GAC | TCT | GAC | AGG | CTG | AAG | GAT | GTG | AAA | GGA | GTC | 2016 |
| Leu | Leu | Val | Asp 660 | Phe | Asp | Ser | Asp | Arg 665 | Leu | Lys | Asp | Val | Lys 670 | Gly | Val | |
| ACG | ACA | GTG | GTC | GTC | CGC | AAG | AAA | TCC | TGT | TTT | ATT | AGG | TGT | CCT | | 2061 |
| Thr | Thr | Val 675 | Val | Val | Arg | Lys | Lys 680 | Ser | Cys | Phe | Ile | Arg 685 | Cys | Pro | | |
| TAA | | | | | | | | | | | | | | | | 2064 |

( 2 ) INFORMATION FOR SEQ ID NO:31:

( i ) SEQUENCE CHARACTERISTICS:
        ( A ) LENGTH: 687 amino acids
        ( B ) TYPE: amino acid
        ( D ) TOPOLOGY: linear ( i i ) MOLECULE TYPE: protein ( x i ) SEQUENCE DESCRIPTION: SEQ ID NO:31:

| | | | | | | | | | | | | | | |
|---|---|---|---|---|---|---|---|---|---|---|---|---|---|---|
| Asp 1 | Asn | Gln | Asn | Ile 5 | Pro | Ile | Thr | Asp | Val 10 | Asp | Val | Arg | Ser | His 15 | Glu |
| Asn | Asn | Leu | Ala 20 | His | Arg | Thr | Arg | Glu 25 | Ile | Asp | Arg | Glu | Arg 30 | Leu | Ile |
| Val | Arg | Arg 35 | Gly | Gln | Pro | Phe | Ser 40 | Ile | Ser | Leu | Gln | Cys 45 | Cys | Asp | Ser |
| Leu | Thr 50 | Arg | Asn | His | His | Leu 55 | Glu | Leu | Ser | Leu | His 60 | Leu | Gly | Lys | Lys |
| Asp | Glu | Val | Val | Ile | Lys | Val | His | Asn | Glu | Pro | Glu | Ala | Gly | Gly | Lys |

-continued

| 65 | | | | | 70 | | | | | 75 | | | | | 80 |
|---|---|---|---|---|---|---|---|---|---|---|---|---|---|---|---|
| Trp | Trp | Phe | Asn | His<br>85 | Gln | Lys | Val | Gln | Asp<br>90 | Glu | Ile | Leu | Leu | Thr<br>95 | Leu |
| His | Ser | Pro | Ala<br>100 | Asp | Ala | Ile | Ile | Gly<br>105 | Glu | Tyr | His | Leu | Thr<br>110 | Val | Leu |
| Ile | Lys | Ser<br>115 | Pro | Asp | Gly | His | Phe<br>120 | Val | Lys | Lys | Thr | Lys<br>125 | Asn | Ile | Gly |
| Phe | His<br>130 | Leu | Leu | Phe | Asn | Pro<br>135 | Trp | Cys | Lys | Asp | Ala<br>140 | Val | Tyr | Leu |  |
| Pro<br>145 | Asp | Glu | Arg | Met | Leu<br>150 | Asp | Glu | Tyr | Val | Met<br>155 | Asn | Glu | Glu | Gly | Ile<br>160 |
| Ile | Tyr | Arg | Gly | Thr<br>165 | Ser | Asn | His | Ile | Ser<br>170 | Ser | Ile | Pro | Trp | Asn<br>175 | Tyr |
| Gly | Gln | Phe | Glu<br>180 | Asp | Tyr | Val | Met | Asp<br>185 | Ile | Cys | Phe | Gln | Val<br>190 | Leu | Asp |
| Asn | Ser | Lys<br>195 | Glu | Ala | Leu | Lys | Asn<br>200 | Ser | Lys | Met | Asp | Ile<br>205 | Glu | Lys | Arg |
| Ser | Asp<br>210 | Pro | Val | Tyr | Val | Ser<br>215 | Arg | Met | Ile | Thr | Ala<br>220 | Met | Val | Asn | Ser |
| Asn<br>225 | Gly | Asp | Arg | Gly | Val<br>230 | Leu | Thr | Gly | Gln | Trp<br>235 | His | Glu | Pro | Tyr | Thr<br>240 |
| Gly | Gly | Phe | Ser | Pro<br>245 | Leu | Arg | Trp | Thr | Gly<br>250 | Ser | Val | Pro | Ile | Leu<br>255 | Arg |
| Lys | Trp | Ser | Lys<br>260 | Ala | Glu | Val | Arg | Ala<br>265 | Val | Lys | Tyr | Gly | Gln<br>270 | Cys | Trp |
| Val | Phe | Ala<br>275 | Ala | Val | Ala | Cys<br>280 | Thr | Val | Leu | Arg | Cys<br>285 | Leu | Gly | Ile | Pro |
| Thr | Arg<br>290 | Asn | Ile | Thr | Asn | Phe<br>295 | Asn | Ser | Ala | His | Asp<br>300 | Val | Asp | Gly | Asn |
| Leu<br>305 | Ser | Val | Asp | Ile | Val<br>310 | Leu | Asn | Lys | Glu | Met<br>315 | Glu | Ser | Val | Gly<br>320 | Lys |
| Lys | Asp | Ser | Ser | Trp<br>325 | Asn | Phe | His | Cys | Trp<br>330 | Ile | Glu | Ser | Trp | Met<br>335 | Arg |
| Arg | Asp | Asp | Leu<br>340 | Ser | Lys | Gly | Asn | Asp<br>345 | Gly | Trp | Gln | Val | Leu<br>350 | Asp | Pro |
| Thr | Pro | Gln<br>355 | Glu | Leu | Ser | Asp | Gly<br>360 | Glu | Tyr | Cys | Cys | Gly<br>365 | Pro | Cys | Pro |
| Val | Thr<br>370 | Ala | Ile | Lys | Glu | Gly<br>375 | Asn | Leu | Ser | Val | Lys<br>380 | Tyr | Asp | Ala | Pro |
| Phe<br>385 | Ile | Phe | Ala | Glu | Val<br>390 | Asn | Ala | Asp | Ile | Ile<br>395 | Tyr | Trp | Met | Ala | Gly<br>400 |
| Pro | Gly | Gly | Glu | Arg<br>405 | Lys | Lys | Ile | Asp | Val<br>410 | Asp | Gln | Ser | Gly | Val<br>415 | Gly |
| Lys | Asn | Ile | Ser<br>420 | Thr | Lys | Ser | Leu | Tyr<br>425 | Gly | Asp | Tyr | Arg | Glu<br>430 | Asp | Val |
| Thr | Leu | His<br>435 | Tyr | Lys | Tyr | Pro | Glu<br>440 | Gly | Ser | Lys | Lys | Glu<br>445 | Arg | Glu | Val |
| Tyr | Gln<br>450 | Lys | Ala | Gly | His | Arg<br>455 | Ile | Lys | Glu | Gln | Ile<br>460 | Cys | Glu | Asn | Lys |
| Gly<br>465 | Pro | Gln | Gln | Leu | Gln<br>470 | Leu | Ser | Val | Lys | His<br>475 | Gly | Lys | Pro | Val | Phe<br>480 |
| Gly | Thr | Asp | Phe | Asp<br>485 | Val | Ile | Val | Glu | Val<br>490 | Lys | Asn | Glu | Gly | Gln<br>495 | Lys |

| Asp | Thr | Ser | Pro 500 | Gln | Leu | Leu | Ile | Val 505 | Val | Met | Ala | Val | Thr 510 | Tyr | Asn |
| Ser | Ile | Asn 515 | Gln | Gly | Glu | Cys | Gln 520 | Arg | Lys | Ala | Thr | Ile 525 | Val | Thr | Val |
| Pro | Ala 530 | Arg | Lys | Thr | His | Lys 535 | Glu | Val | Leu | Arg | Leu 540 | Arg | Tyr | Asp | Asp |
| Tyr 545 | Val | Lys | Cys | Val | Ser 550 | Glu | His | His | Leu | Ile 555 | Arg | Val | Lys | Ala | Leu 560 |
| Met | Glu | Val | Pro | Gly 565 | Asp | Asn | Lys | Pro | Val 570 | Met | Ser | Val | Ala | Asn 575 | Ile |
| Pro | Leu | Ser | Met 580 | Pro | Glu | Leu | Leu | Val 585 | Glu | Val | Pro | Gly | Ser 590 | Ile | Ile |
| Val | Gln | Glu 595 | Lys | Val | Thr | Ala | Phe 600 | Ile | Ser | Phe | Thr | Asn 605 | Pro | Leu | Thr |
| Val | Pro 610 | Leu | Lys | Arg | Gly | Met 615 | Phe | Thr | Val | Glu | Gly 620 | Ser | Gly | Leu | Leu |
| Ser 625 | Ala | Ser | Glu | Ile | Tyr 630 | Val | Lys | Gly | Asp | Ile 635 | Ala | Pro | Gly | Gln | Lys 640 |
| Val | Ser | Val | Lys | Ile 645 | Thr | Phe | Thr | Pro | Met 650 | Arg | Val | Gly | Val | Arg 655 | Lys |
| Leu | Leu | Val | Asp 660 | Phe | Asp | Ser | Asp | Arg 665 | Leu | Lys | Asp | Val | Lys 670 | Gly | Val |
| Thr | Thr | Val 675 | Val | Val | Arg | Lys | Lys 680 | Ser | Cys | Phe | Ile | Arg 685 | Cys | Pro | |

( 2 ) INFORMATION FOR SEQ ID NO:32:

( i ) SEQUENCE CHARACTERISTICS:
        ( A ) LENGTH: 2064 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: Paralichthys olivaceus
        ( F ) TISSUE TYPE: liver ( i x ) FEATURE:
        ( A ) NAME/KEY: CDS
        ( B ) LOCATION: 1..2061

( x i ) SEQUENCE DESCRIPTION: SEQ ID NO:32:

| GAC | AAT | CAG | AAC | ATT | CCG | ATC | ACT | GAT | GTG | GAT | GTG | AGA | AGT | CAT | GAA | 48 |
| Asp 1 | Asn | Gln | Asn | Ile 5 | Pro | Ile | Thr | Asp | Val 10 | Asp | Val | Arg | Ser | His 15 | Glu | |
| AAC | AAC | TTG | GCT | CAC | CGC | ACC | AGG | GAG | ATT | GAT | CGG | GAG | CGC | TTG | ATC | 96 |
| Asn | Asn | Leu | Ala 20 | His | Arg | Thr | Arg | Glu 25 | Ile | Asp | Arg | Glu | Arg 30 | Leu | Ile | |
| GTC | CGC | AGG | GGT | CAA | CCC | TTC | TCC | ATA | TCT | CTG | CAG | TGC | TGC | GAC | TCG | 144 |
| Val | Arg | Arg 35 | Gly | Gln | Pro | Phe | Ser 40 | Ile | Ser | Leu | Gln | Cys 45 | Cys | Asp | Ser | |
| CTG | ACC | CGG | AAT | CAC | CAT | CTG | GAA | CTG | TCC | CTG | CAC | CTC | GGT | AAG | AAA | 192 |
| Leu | Thr 50 | Arg | Asn | His | His 55 | Leu | Glu | Leu | Ser | Leu 60 | His | Leu | Gly | Lys | Lys | |
| GAT | GAG | GTG | GTG | ATT | AAG | GTG | CAC | AAT | GAG | CCT | GAG | GCT | GGA | GGC | AAG | 240 |
| Asp | Glu | Val | Val | Ile 70 | Lys | Val | His | Asn | Glu 75 | Pro | Glu | Ala | Gly | Gly | Lys 80 | |
| | | | | | | | | | | | | | | | | |
| Asp 65 | | | | | | | | | | | | | | | | |
| TGG | TGG | TTT | AAC | CAT | CAG | AAA | GTG | CAG | GAT | GAA | ATT | CTG | CTG | ACT | CTA | 288 |
| Trp | Trp | Phe | Asn | His 85 | Gln | Lys | Val | Gln | Asp 90 | Glu | Ile | Leu | Leu | Thr 95 | Leu | |

| | | | | | | | | | | | | | | | | |
|---|---|---|---|---|---|---|---|---|---|---|---|---|---|---|---|---|
| CAC | AGT | CCA | GCG | GAC | GCC | ATA | ATT | GGC | GAG | TAC | CAC | CTG | ACT | GTG | TTG | 336 |
| His | Ser | Pro | Ala | Asp | Ala | Ile | Ile | Gly | Glu | Tyr | His | Leu | Thr | Val | Leu | |
| | | | 100 | | | | 105 | | | | | | 110 | | | |
| ATC | AAG | TCA | CCG | GAT | GGA | CAC | TTT | GTG | AAG | AAG | ACT | AAG | AAC | ATT | GGA | 384 |
| Ile | Lys | Ser | Pro | Asp | Gly | His | Phe | Val | Lys | Lys | Thr | Lys | Asn | Ile | Gly | |
| | | 115 | | | | | 120 | | | | | 125 | | | | |
| TTC | CAC | CTG | CTC | TTT | AAC | CCC | TGG | TGC | AAA | GAT | GAT | GCT | GTG | TAC | CTC | 432 |
| Phe | His | Leu | Leu | Phe | Asn | Pro | Trp | Cys | Lys | Asp | Asp | Ala | Val | Tyr | Leu | |
| | 130 | | | | | 135 | | | | | 140 | | | | | |
| CCT | GAT | GAA | AGG | ATG | CTC | GAC | GAG | TAT | GTT | ATG | AAT | GAG | GAG | GGG | ATC | 480 |
| Pro | Asp | Glu | Arg | Met | Leu | Asp | Glu | Tyr | Val | Met | Asn | Glu | Glu | Gly | Ile | |
| 145 | | | | | 150 | | | | | 155 | | | | | 160 | |
| ATT | TAC | AGG | GGA | ACC | TCG | AAT | CAC | ATC | AGT | AGC | ATA | CCC | TGG | AAT | TAC | 528 |
| Ile | Tyr | Arg | Gly | Thr | Ser | Asn | His | Ile | Ser | Ser | Ile | Pro | Trp | Asn | Tyr | |
| | | | 165 | | | | | 170 | | | | | | 175 | | |
| GGA | CAG | TTT | GAG | GAC | TAT | GTG | ATG | GAC | ATC | TGT | TTT | CAA | GTT | CTG | GAC | 576 |
| Gly | Gln | Phe | Glu | Asp | Tyr | Val | Met | Asp | Ile | Cys | Phe | Gln | Val | Leu | Asp | |
| | | | 180 | | | | | 185 | | | | | 190 | | | |
| AAC | TCC | AAG | GAA | GCC | CTG | AAG | AAT | TCA | AAG | ATG | GAC | ATT | GAG | AAG | AGA | 624 |
| Asn | Ser | Lys | Glu | Ala | Leu | Lys | Asn | Ser | Lys | Met | Asp | Ile | Glu | Lys | Arg | |
| | | 195 | | | | | 200 | | | | | 205 | | | | |
| TCT | GAC | CCT | GTC | TAT | GTC | AGC | AGG | ATG | ATC | ACT | GCG | ATG | GTG | AAC | TCT | 672 |
| Ser | Asp | Pro | Val | Tyr | Val | Ser | Arg | Met | Ile | Thr | Ala | Met | Val | Asn | Ser | |
| | 210 | | | | | 215 | | | | | 220 | | | | | |
| AAC | GGT | GAC | AGG | GGT | GTG | CTG | ACT | GGT | CAG | TGG | CAC | GAG | CCA | TAC | ACT | 720 |
| Asn | Gly | Asp | Arg | Gly | Val | Leu | Thr | Gly | Gln | Trp | His | Glu | Pro | Tyr | Thr | |
| 225 | | | | | 230 | | | | | 235 | | | | | 240 | |
| GGC | GGG | TTC | TCA | CCA | CTT | CGA | TGG | ACC | GGC | AGC | GTG | CCC | ATC | CTC | CGG | 768 |
| Gly | Gly | Phe | Ser | Pro | Leu | Arg | Trp | Thr | Gly | Ser | Val | Pro | Ile | Leu | Arg | |
| | | | | 245 | | | | | 250 | | | | | 255 | | |
| AAG | TGG | AGC | AAG | GCC | GAG | GTC | AGG | GCG | GTC | AAA | TAT | GGC | CAG | TGC | TGG | 816 |
| Lys | Trp | Ser | Lys | Ala | Glu | Val | Arg | Ala | Val | Lys | Tyr | Gly | Gln | Cys | Trp | |
| | | | 260 | | | | | 265 | | | | | 270 | | | |
| GTG | TTT | GCT | GCT | GTC | GCC | TGC | ACA | GTG | CTG | CGT | TGT | CTG | GGA | ATC | CCA | 864 |
| Val | Phe | Ala | Ala | Val | Ala | Cys | Thr | Val | Leu | Arg | Cys | Leu | Gly | Ile | Pro | |
| | | 275 | | | | | 280 | | | | | 285 | | | | |
| ACA | CGC | AAC | ATC | ACT | AAC | TTC | AAT | TCA | GCA | CAT | GAT | GTC | GAT | GGA | AAC | 912 |
| Thr | Arg | Asn | Ile | Thr | Asn | Phe | Asn | Ser | Ala | His | Asp | Val | Asp | Gly | Asn | |
| | 290 | | | | | 295 | | | | | 300 | | | | | |
| CTC | TCC | GTC | GAC | ATC | GTG | TTG | AAC | AAA | GAA | ATG | GAG | AGC | GTT | GGC | AAG | 960 |
| Leu | Ser | Val | Asp | Ile | Val | Leu | Asn | Lys | Glu | Met | Glu | Ser | Val | Gly | Lys | |
| 305 | | | | | 310 | | | | | 315 | | | | | 320 | |
| AAG | GAC | AGT | AGC | TGG | AAC | TTC | CAC | TGT | TGG | ATC | GAG | TCC | TGG | ATG | AGG | 1008 |
| Lys | Asp | Ser | Ser | Trp | Asn | Phe | His | Cys | Trp | Ile | Glu | Ser | Trp | Met | Arg | |
| | | | | 325 | | | | | 330 | | | | | 335 | | |
| AGA | GAC | GAC | CTC | TCT | AAA | GGA | AAT | GAC | GGC | TGG | CAG | GTT | TTG | GAC | CCC | 1056 |
| Arg | Asp | Asp | Leu | Ser | Lys | Gly | Asn | Asp | Gly | Trp | Gln | Val | Leu | Asp | Pro | |
| | | | 340 | | | | | 345 | | | | | 350 | | | |
| ACC | CCT | CAA | GAA | CTG | AGT | GAT | GGT | GAG | TAT | TGC | TGC | GGC | CCG | TGT | CCA | 1104 |
| Thr | Pro | Gln | Glu | Leu | Ser | Asp | Gly | Glu | Tyr | Cys | Cys | Gly | Pro | Cys | Pro | |
| | | 355 | | | | | 360 | | | | | 365 | | | | |
| GTC | ACC | GCC | ATC | AAG | GAG | GGA | AAT | CTG | AGT | GTG | AAG | TAC | GAC | GCT | CCG | 1152 |
| Val | Thr | Ala | Ile | Lys | Glu | Gly | Asn | Leu | Ser | Val | Lys | Tyr | Asp | Ala | Pro | |
| | 370 | | | | | 375 | | | | | 380 | | | | | |
| TTT | ATC | TTC | GCT | GAG | GTG | AAC | GCT | GAC | ATC | ATC | TAC | TGG | ATG | GCT | GGA | 1200 |
| Phe | Ile | Phe | Ala | Glu | Val | Asn | Ala | Asp | Ile | Ile | Tyr | Trp | Met | Ala | Gly | |
| 385 | | | | | 390 | | | | | 395 | | | | | 400 | |
| CCA | GGA | GGC | GAA | CGG | AAG | AAG | ATC | GAT | GTG | GAC | CAG | AGT | GGT | GTG | GGG | 1248 |
| Pro | Gly | Gly | Glu | Arg | Lys | Lys | Ile | Asp | Val | Asp | Gln | Ser | Gly | Val | Gly | |
| | | | | 405 | | | | | 410 | | | | | 415 | | |

```
AAG  AAC  ATC  AGC  ACC  AAA  AGT  CTT  TAT  GGC  GAC  TAC  AGG  GAG  GAT  GTC      1296
Lys  Asn  Ile  Ser  Thr  Lys  Ser  Leu  Tyr  Gly  Asp  Tyr  Arg  Glu  Asp  Val
               420            425                      430

ACT  CTG  CAC  TAC  AAA  TAC  CCC  GAA  GGC  TCC  AAG  AAG  GAG  AGA  GAG  GTG      1344
Thr  Leu  His  Tyr  Lys  Tyr  Pro  Glu  Gly  Ser  Lys  Lys  Glu  Arg  Glu  Val
               435                 440                      445

TAC  CAG  AAG  GCC  GGA  CAC  CGA  ATC  AAA  GAG  CAG  ATC  TGT  GAA  AAC  AAA      1392
Tyr  Gln  Lys  Ala  Gly  His  Arg  Ile  Lys  Glu  Gln  Ile  Cys  Glu  Asn  Lys
     450                      455                 460

GGT  CCA  CAA  CAA  CTG  CAG  CTG  TCA  GTC  AAG  CAC  GGG  AAA  CCT  GTA  TTT      1440
Gly  Pro  Gln  Gln  Leu  Gln  Leu  Ser  Val  Lys  His  Gly  Lys  Pro  Val  Phe
465                      470                 475                           480

GGC  ACT  GAC  TTC  GAT  GTG  ATA  GTT  GAG  GTG  AAG  AAT  GAA  GGA  CAG  AAA      1488
Gly  Thr  Asp  Phe  Asp  Val  Ile  Val  Glu  Val  Lys  Asn  Glu  Gly  Gln  Lys
               485                 490                      495

GAC  ACC  AGT  CCA  CAG  CTG  CTG  ATT  GTG  GTC  ATG  GCC  GTG  ACC  TAC  AAT      1536
Asp  Thr  Ser  Pro  Gln  Leu  Leu  Ile  Val  Val  Met  Ala  Val  Thr  Tyr  Asn
               500                 505                      510

TCC  ATC  AAT  CAA  GGG  GAG  TGT  CAG  AGG  AAG  GCG  ACC  ATA  GTG  ACC  GTG      1584
Ser  Ile  Asn  Gln  Gly  Glu  Cys  Gln  Arg  Lys  Ala  Thr  Ile  Val  Thr  Val
          515                 520                      525

CCG  GCT  CGC  AAA  ACC  CAC  AAG  GAA  GTG  CTG  CGT  CTG  CGC  TAC  GAC  GAC      1632
Pro  Ala  Arg  Lys  Thr  His  Lys  Glu  Val  Leu  Arg  Leu  Arg  Tyr  Asp  Asp
     530                 535                      540

TAT  GTC  AAA  TGT  GTC  TCT  GAG  CAC  CAT  CTG  ATC  AGG  GTG  AAA  GCG  CTC      1680
Tyr  Val  Lys  Cys  Val  Ser  Glu  His  His  Leu  Ile  Arg  Val  Lys  Ala  Leu
545                      550                 555                           560

ATG  GAG  GTT  CCA  GGG  GAC  AAC  AAA  CCC  GTC  ATG  AGT  GTG  GCC  AAC  ATT      1728
Met  Glu  Val  Pro  Gly  Asp  Asn  Lys  Pro  Val  Met  Ser  Val  Ala  Asn  Ile
               565                 570                      575

CCA  CTG  AGC  ATG  CCT  GAG  CTC  CTG  GTA  GAG  GTA  CCT  GGG  AGC  ATC  ATT      1776
Pro  Leu  Ser  Met  Pro  Glu  Leu  Leu  Val  Glu  Val  Pro  Gly  Ser  Ile  Ile
               580                 585                      590

GTT  CAG  GAG  AAG  GTG  ACA  GCC  TTC  ATC  TCC  TTC  ACA  AAT  CCT  CTA  ACT      1824
Val  Gln  Glu  Lys  Val  Thr  Ala  Phe  Ile  Ser  Phe  Thr  Asn  Pro  Leu  Thr
     595                      600                 605

GTC  CCA  CTG  AAG  CGT  GGC  ATG  TTC  ACC  GTG  GAG  GGG  TCC  GGA  CTA  CTG      1872
Val  Pro  Leu  Lys  Arg  Gly  Met  Phe  Thr  Val  Glu  Gly  Ser  Gly  Leu  Leu
     610                      615                 620

TCT  GCC  TCT  GAG  ATC  TAT  GTG  AAA  GGG  GAC  ATT  GCT  CCA  GGC  CAG  AAG      1920
Ser  Ala  Ser  Glu  Ile  Tyr  Val  Lys  Gly  Asp  Ile  Ala  Pro  Gly  Gln  Lys
625                      630                 635                           640

GTT  TCT  GTC  AAG  ATC  ACC  TTC  ACG  CCC  ATG  AGG  GTC  GGG  GTG  AGG  AAG      1968
Val  Ser  Val  Lys  Ile  Thr  Phe  Thr  Pro  Met  Arg  Val  Gly  Val  Arg  Lys
               645                 650                      655

CTC  CTG  GTG  GAC  TTT  GAC  TCT  GAC  AGG  CTG  AAG  GAT  GTG  AAA  GGA  GTC      2016
Leu  Leu  Val  Asp  Phe  Asp  Ser  Asp  Arg  Leu  Lys  Asp  Val  Lys  Gly  Val
               660                 665                      670

ACG  ACA  GTG  GTC  GTC  CGC  AAG  AAA  TCC  TGT  TTT  ATT  AGG  TGT  CCT           2061
Thr  Thr  Val  Val  Val  Arg  Lys  Lys  Ser  Cys  Phe  Ile  Arg  Cys  Pro
               675                 680                      685

TAA                                                                                 2064
```

( 2 ) INFORMATION FOR SEQ ID NO:33:

( i ) SEQUENCE CHARACTERISTICS:
        ( A ) LENGTH: 687 amino acids
        ( B ) TYPE: amino acid
        ( D ) TOPOLOGY: linear ( i i ) MOLECULE TYPE: protein ( x i ) SEQUENCE DESCRIPTION: SEQ ID NO:33:

| Asp | Asn | Gln | Asn | Ile | Pro | Ile | Thr | Asp | Val | Asp | Val | Arg | Ser | His | Glu |
|---|---|---|---|---|---|---|---|---|---|---|---|---|---|---|---|
| 1 | | | | 5 | | | | | 10 | | | | | 15 | |
| Asn | Asn | Leu | Ala | His | Arg | Thr | Arg | Glu | Ile | Asp | Arg | Glu | Arg | Leu | Ile |
| | | | 20 | | | | 25 | | | | | 30 | | | |
| Val | Arg | Arg | Gly | Gln | Pro | Phe | Ser | Ile | Ser | Leu | Gln | Cys | Cys | Asp | Ser |
| | | 35 | | | | 40 | | | | | 45 | | | | |
| Leu | Thr | Arg | Asn | His | His | Leu | Glu | Leu | Ser | Leu | His | Leu | Gly | Lys | Lys |
| | 50 | | | | 55 | | | | | | 60 | | | | |
| Asp | Glu | Val | Val | Ile | Lys | Val | His | Asn | Glu | Pro | Glu | Ala | Gly | Gly | Lys |
| 65 | | | | | 70 | | | | | 75 | | | | | 80 |
| Trp | Trp | Phe | Asn | His | Gln | Lys | Val | Gln | Asp | Glu | Ile | Leu | Leu | Thr | Leu |
| | | | | 85 | | | | | 90 | | | | | 95 | |
| His | Ser | Pro | Ala | Asp | Ala | Ile | Ile | Gly | Glu | Tyr | His | Leu | Thr | Val | Leu |
| | | | 100 | | | | | 105 | | | | | 110 | | |
| Ile | Lys | Ser | Pro | Asp | Gly | His | Phe | Val | Lys | Lys | Thr | Lys | Asn | Ile | Gly |
| | | 115 | | | | 120 | | | | | 125 | | | | |
| Phe | His | Leu | Leu | Phe | Asn | Pro | Trp | Cys | Lys | Asp | Asp | Ala | Val | Tyr | Leu |
| | 130 | | | | | 135 | | | | | 140 | | | | |
| Pro | Asp | Glu | Arg | Met | Leu | Asp | Glu | Tyr | Val | Met | Asn | Glu | Glu | Gly | Ile |
| 145 | | | | | 150 | | | | | 155 | | | | | 160 |
| Ile | Tyr | Arg | Gly | Thr | Ser | Asn | His | Ile | Ser | Ser | Ile | Pro | Trp | Asn | Tyr |
| | | | | 165 | | | | | 170 | | | | | 175 | |
| Gly | Gln | Phe | Glu | Asp | Tyr | Val | Met | Asp | Ile | Cys | Phe | Gln | Val | Leu | Asp |
| | | | 180 | | | | | 185 | | | | | 190 | | |
| Asn | Ser | Lys | Glu | Ala | Leu | Lys | Asn | Ser | Lys | Met | Asp | Ile | Glu | Lys | Arg |
| | | 195 | | | | 200 | | | | | 205 | | | | |
| Ser | Asp | Pro | Val | Tyr | Val | Ser | Arg | Met | Ile | Thr | Ala | Met | Val | Asn | Ser |
| 210 | | | | | 215 | | | | | 220 | | | | | |
| Asn | Gly | Asp | Arg | Gly | Val | Leu | Thr | Gly | Gln | Trp | His | Glu | Pro | Tyr | Thr |
| 225 | | | | | 230 | | | | | 235 | | | | | 240 |
| Gly | Gly | Phe | Ser | Pro | Leu | Arg | Trp | Thr | Gly | Ser | Val | Pro | Ile | Leu | Arg |
| | | | | 245 | | | | | 250 | | | | | 255 | |
| Lys | Trp | Ser | Lys | Ala | Glu | Val | Arg | Ala | Val | Lys | Tyr | Gly | Gln | Cys | Trp |
| | | | 260 | | | | | 265 | | | | | 270 | | |
| Val | Phe | Ala | Ala | Val | Ala | Cys | Thr | Val | Leu | Arg | Cys | Leu | Gly | Ile | Pro |
| | | 275 | | | | 280 | | | | | 285 | | | | |
| Thr | Arg | Asn | Ile | Thr | Asn | Phe | Asn | Ser | Ala | His | Asp | Val | Asp | Gly | Asn |
| | 290 | | | | | 295 | | | | | 300 | | | | |
| Leu | Ser | Val | Asp | Ile | Val | Leu | Asn | Lys | Glu | Met | Glu | Ser | Val | Gly | Lys |
| 305 | | | | | 310 | | | | | 315 | | | | | 320 |
| Lys | Asp | Ser | Ser | Trp | Asn | Phe | His | Cys | Trp | Ile | Glu | Ser | Trp | Met | Arg |
| | | | | 325 | | | | | 330 | | | | | 335 | |
| Arg | Asp | Asp | Leu | Ser | Lys | Gly | Asn | Asp | Gly | Trp | Gln | Val | Leu | Asp | Pro |
| | | | 340 | | | | | 345 | | | | | 350 | | |
| Thr | Pro | Gln | Glu | Leu | Ser | Asp | Gly | Glu | Tyr | Cys | Cys | Gly | Pro | Cys | Pro |
| | | 355 | | | | 360 | | | | | 365 | | | | |
| Val | Thr | Ala | Ile | Lys | Glu | Gly | Asn | Leu | Ser | Val | Lys | Tyr | Asp | Ala | Pro |
| | 370 | | | | | 375 | | | | | 380 | | | | |
| Phe | Ile | Phe | Ala | Glu | Val | Asn | Ala | Asp | Ile | Ile | Tyr | Trp | Met | Ala | Gly |
| 385 | | | | | 390 | | | | | 395 | | | | | 400 |
| Pro | Gly | Gly | Glu | Arg | Lys | Lys | Ile | Asp | Val | Asp | Gln | Ser | Gly | Val | Gly |
| | | | | 405 | | | | | 410 | | | | | 415 | |

| | | | | | | | | | | | | | | |
|---|---|---|---|---|---|---|---|---|---|---|---|---|---|---|
| Lys | Asn | Ile | Ser | Thr | Lys | Ser | Leu | Tyr | Gly | Asp | Tyr | Arg | Glu | Asp | Val |
| | | | 420 | | | | | 425 | | | | 430 | | |
| Thr | Leu | His | Tyr | Lys | Tyr | Pro | Glu | Gly | Ser | Lys | Lys | Glu | Arg | Glu | Val |
| | | 435 | | | | 440 | | | | | 445 | | | |
| Tyr | Gln | Lys | Ala | Gly | His | Arg | Ile | Lys | Glu | Gln | Ile | Cys | Glu | Asn | Lys |
| 450 | | | | | 455 | | | | | 460 | | | | |
| Gly | Pro | Gln | Gln | Leu | Gln | Leu | Ser | Val | Lys | His | Gly | Lys | Pro | Val | Phe |
| 465 | | | | | 470 | | | | | 475 | | | | | 480 |
| Gly | Thr | Asp | Phe | Asp | Val | Ile | Val | Glu | Val | Lys | Asn | Glu | Gly | Gln | Lys |
| | | | | 485 | | | | | 490 | | | | | 495 | |
| Asp | Thr | Ser | Pro | Gln | Leu | Leu | Ile | Val | Val | Met | Ala | Val | Thr | Tyr | Asn |
| | | | 500 | | | | | 505 | | | | | 510 | | |
| Ser | Ile | Asn | Gln | Gly | Glu | Cys | Gln | Arg | Lys | Ala | Thr | Ile | Val | Thr | Val |
| | | 515 | | | | | 520 | | | | | 525 | | | |
| Pro | Ala | Arg | Lys | Thr | His | Lys | Glu | Val | Leu | Arg | Leu | Arg | Tyr | Asp | Asp |
| | 530 | | | | | 535 | | | | | 540 | | | | |
| Tyr | Val | Lys | Cys | Val | Ser | Glu | His | His | Leu | Ile | Arg | Val | Lys | Ala | Leu |
| 545 | | | | | 550 | | | | | 555 | | | | | 560 |
| Met | Glu | Val | Pro | Gly | Asp | Asn | Lys | Pro | Val | Met | Ser | Val | Ala | Asn | Ile |
| | | | | 565 | | | | | 570 | | | | | 575 | |
| Pro | Leu | Ser | Met | Pro | Glu | Leu | Leu | Val | Glu | Val | Pro | Gly | Ser | Ile | Ile |
| | | | 580 | | | | | 585 | | | | | 590 | | |
| Val | Gln | Glu | Lys | Val | Thr | Ala | Phe | Ile | Ser | Phe | Thr | Asn | Pro | Leu | Thr |
| | | 595 | | | | | 600 | | | | | 605 | | | |
| Val | Pro | Leu | Lys | Arg | Gly | Met | Phe | Thr | Val | Glu | Gly | Ser | Gly | Leu | Leu |
| | 610 | | | | | 615 | | | | | 620 | | | | |
| Ser | Ala | Ser | Glu | Ile | Tyr | Val | Lys | Gly | Asp | Ile | Ala | Pro | Gly | Gln | Lys |
| 625 | | | | | 630 | | | | | 635 | | | | | 640 |
| Val | Ser | Val | Lys | Ile | Thr | Phe | Thr | Pro | Met | Arg | Val | Gly | Val | Arg | Lys |
| | | | | 645 | | | | | 650 | | | | | 655 | |
| Leu | Leu | Val | Asp | Phe | Asp | Ser | Asp | Arg | Leu | Lys | Asp | Val | Lys | Gly | Val |
| | | | 660 | | | | | 665 | | | | | 670 | | |
| Thr | Thr | Val | Val | Val | Arg | Lys | Lys | Ser | Cys | Phe | Ile | Arg | Cys | Pro | |
| | | 675 | | | | | 680 | | | | | 685 | | | |

( 2 ) INFORMATION FOR SEQ ID NO:34:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:34:

Glu Ile Asp Arg
    1

( 2 ) INFORMATION FOR SEQ ID NO:35:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:35:

Val Tyr Leu Pro Asp Glu

```
    1               5
```

(2) INFORMATION FOR SEQ ID NO:36:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:36:

```
Val  Met  Asp  Ile  Cys  Phe
1                    5
```

(2) INFORMATION FOR SEQ ID NO:37:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:37:

```
Asp  Gly  Asn  Leu  Ser  Xaa  Asp
1                    5
```

(2) INFORMATION FOR SEQ ID NO:38:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:38:

```
Asp  Ser  Xaa  Trp  Asn  Phe  His  Cys  Trp  Xaa  Glu  Ser
1                    5                         10
```

(2) INFORMATION FOR SEQ ID NO:39:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:39:

```
Gly  Trp  Gln  Val  Leu  Asp  Pro
1                    5
```

(2) INFORMATION FOR SEQ ID NO:40:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:40:

```
Lys  Glu  Arg  Glu  Val  Tyr  Xaa  Lys  Ala  Gly
1                    5                         10
```

(2) INFORMATION FOR SEQ ID NO:41:

( i ) SEQUENCE CHARACTERISTICS:
   ( A ) LENGTH: 10 amino acids
   ( B ) TYPE: amino acid
   ( D ) TOPOLOGY: linear ( i i ) MOLECULE TYPE: peptide ( x i ) SEQUENCE DESCRIPTION: SEQ ID NO:41:

Pro Val Phe Gly Thr Asp Phe Asp Val Ile
1               5                   10

( 2 ) INFORMATION FOR SEQ ID NO:42:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:42:

Ala Val Thr Tyr Asn Ser
1               5

( 2 ) INFORMATION FOR SEQ ID NO:43:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:43:

Pro Ala Xaa Lys Xaa His
1               5

( 2 ) INFORMATION FOR SEQ ID NO:44:

( i ) SEQUENCE CHARACTERISTICS:
      ( A ) LENGTH: 4 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:44:

Val Ser Glu His
1

( 2 ) INFORMATION FOR SEQ ID NO:45:

( i ) SEQUENCE CHARACTERISTICS:
      ( A ) LENGTH: 9 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:45:

Leu Val Asp Phe Asp Ser Asp Arg Leu
1               5

( 2 ) INFORMATION FOR SEQ ID NO:46:

( i ) SEQUENCE CHARACTERISTICS:
      ( A ) LENGTH: 7 amino acids
      ( B ) TYPE: amino acid
      ( D ) TOPOLOGY: linear ( i i ) MOLECULE TYPE: peptide ( v i ) ORIGINAL SOURCE:
    ( A ) ORGANISM: Theragra chalcogramma ( x i ) SEQUENCE DESCRIPTION: SEQ ID NO:46:

Xaa Ala Gly Gly Ser Gly Asp
1                        5

( 2 ) INFORMATION FOR SEQ ID NO:47:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:47:

Trp Trp Leu His Gln Gln Ser
1                       5

( 2 ) INFORMATION FOR SEQ ID NO:48:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:48:

Met Tyr Leu Leu Phe Asn Pro
1                       5

( 2 ) INFORMATION FOR SEQ ID NO:49:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:49:

Trp Gln Glu Pro Tyr Thr Gly Gly
1                       5

( 2 ) INFORMATION FOR SEQ ID NO:50:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:50:

Phe Asp Val Pro Phe Val Phe Ala Glu Val Asn Ala Asp
1                       5                       10

( 2 ) INFORMATION FOR SEQ ID NO:51:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:51:

Ser Xaa Tyr Ser Asn Glu
1               5

( 2 ) INFORMATION FOR SEQ ID NO:52:

( i ) SEQUENCE CHARACTERISTICS:
( A ) LENGTH: 10 amino acids
( B ) TYPE: amino acid
( D ) TOPOLOGY: linear ( i i ) MOLECULE TYPE: peptide ( x i ) SEQUENCE DESCRIPTION: SEQ ID NO:52:

His His Leu Glu Leu Val Leu Xaa Leu Gly
1               5                   10

( 2 ) INFORMATION FOR SEQ ID NO:53:

( i ) SEQUENCE CHARACTERISTICS:
( A ) LENGTH: 17 amino acids
( B ) TYPE: amino acid
( D ) TOPOLOGY: linear ( i i ) MOLECULE TYPE: peptide ( x i ) SEQUENCE DESCRIPTION: SEQ ID NO:53:

Xaa Xaa Phe Asn Gln Gln Gly Ala Gln Asp Glu Ile Leu Leu Thr Leu
1               5                   10                  15

His ( 2 ) INFORMATION FOR SEQ ID NO:54:

( i ) SEQUENCE CHARACTERISTICS:
( A ) LENGTH: 9 amino acids
( B ) TYPE: amino acid
( D ) TOPOLOGY: linear ( i i ) MOLECULE TYPE: peptide ( x i ) SEQUENCE DESCRIPTION: SEQ ID NO:54:

Ile Ser Phe His Met Leu Phe Asn Pro
1               5

( 2 ) INFORMATION FOR SEQ ID NO:55:

( i ) SEQUENCE CHARACTERISTICS:
( A ) LENGTH: 16 amino acids
( B ) TYPE: amino acid
( D ) TOPOLOGY: linear ( i i ) MOLECULE TYPE: peptide ( x i ) SEQUENCE DESCRIPTION: SEQ ID NO:55:

Leu Gln Glu Tyr Val Met Asn Glu Asp Gly Val Ile Tyr Met Gly Thr
1               5                   10                  15

( 2 ) INFORMATION FOR SEQ ID NO:56:

( i ) SEQUENCE CHARACTERISTICS:
( A ) LENGTH: 18 amino acids
( B ) TYPE: amino acid
( D ) TOPOLOGY: linear ( i i ) MOLECULE TYPE: peptide ( x i ) SEQUENCE DESCRIPTION: SEQ ID NO:56:

Asn Ser Glu Met Asp Ile Glu His Arg Ser Asp Pro Val Tyr Val Gly

```
                 1               5                    10                       15
           Arg  Thr
```

( 2 ) INFORMATION FOR SEQ ID NO:57:

( i ) SEQUENCE CHARACTERISTICS:
      ( A ) LENGTH: 16 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:57:

```
  Tyr  Asp  Ala  Pro  Phe  Val  Phe  Ala  Glu  Val  Asn  Ala  Asp  Thr  Ile  Tyr
  1                   5                        10                       15
```

( 2 ) INFORMATION FOR SEQ ID NO:58:

( i ) SEQUENCE CHARACTERISTICS:
      ( A ) LENGTH: 14 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:58:

```
  Ser  Val  Tyr  Gly  Asn  His  Arg  Glu  Asp  Val  Thr  Leu  His  Tyr
  1                   5                        10
```

( 2 ) INFORMATION FOR SEQ ID NO:59:

( i ) SEQUENCE CHARACTERISTICS:
      ( A ) LENGTH: 18 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:59:

```
  Ala  Gly  Arg  Arg  Val  Thr  Glu  Pro  Ser  Asn  Glu  Ile  Ala  Ile  Gln  Gly
  1                   5                        10                       15
  Arg  Leu
```

( 2 ) INFORMATION FOR SEQ ID NO:60:

( i ) SEQUENCE CHARACTERISTICS:
      ( A ) LENGTH: 15 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:60:

```
  Xaa  Ala  Gln  Pro  Val  Phe  Gly  Thr  Asp  Phe  Asp  Val  Ile  Val  Glu
  1                   5                        10                       15
```

( 2 ) INFORMATION FOR SEQ ID NO:61:

( i ) SEQUENCE CHARACTERISTICS:
      ( A ) LENGTH: 17 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:61:

```
  Asn  Glu  Gly  Gly  Arg  Asp  Ala  His  Ala  Gln  Leu  Thr  Xaa  Leu  Ala  Xaa
  1                   5                        10                       15
```

Ala (2) INFORMATION FOR SEQ ID NO:62:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:62:

```
Thr Ile Ser Val Thr Val Pro Ala His
1               5
```

(2) INFORMATION FOR SEQ ID NO:63:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:63:

```
Ala Val Val Xaa Glu Pro Leu Thr Ala
1               5
```

(2) INFORMATION FOR SEQ ID NO:64:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:64:

```
Gly Gly Val Phe Thr Leu Glu Gly Ala Gly Leu Leu Ser Ala Thr Gln
1               5                   10                  15
Ile His
```

(2) INFORMATION FOR SEQ ID NO:65:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:65:

```
Leu Ser Phe Ser Pro Met Arg Thr Gly Val Arg
1               5                   10
```

(2) INFORMATION FOR SEQ ID NO:66:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:66:

```
Leu Leu Val Asp Phe Asp Ser Asp Arg Leu
1               5                   10
```

( 2 ) INFORMATION FOR SEQ ID NO:67:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:67:

```
Gly Val Thr Thr Val Val Val His
 1               5
```

( 2 ) INFORMATION FOR SEQ ID NO:68:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:68:

```
Tyr Arg Ser Leu Ile Thr Gly Leu His Thr Asp
 1               5                   10
```

( 2 ) INFORMATION FOR SEQ ID NO:69:

( i ) SEQUENCE CHARACTERISTICS:
        ( A ) LENGTH: 2148 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: Paralichthys olivaceus
        ( F ) TISSUE TYPE: liver ( i x ) FEATURE:
        ( A ) NAME/KEY: CDS
        ( B ) LOCATION: 26..2092

( x i ) SEQUENCE DESCRIPTION: SEQ ID NO:69:

```
GAGAAGACGA GGAAAAAGGT CTGCG ATG GAC AAT CAG AAC ATT CCG ATC ACT           52
                           Met Asp Asn Gln Asn Ile Pro Ile Thr
                            1                   5

GAT GTG GAT GTG AGA AGT CAT GAA AAC AAC TTG GCT CAC CGC ACC AGG          100
Asp Val Asp Val Arg Ser His Glu Asn Asn Leu Ala His Arg Thr Arg
 10              15                  20                  25

GAG ATT GAT CGG GAG CGC TTG ATC GTC CGC AGG GGT CAA CCC TTC TCC          148
Glu Ile Asp Arg Glu Arg Leu Ile Val Arg Arg Gly Gln Pro Phe Ser
                 30                  35                  40

ATA TCT CTG CAG TGC TGC GAC TCG CTG ACC CGG AAT CAC CAT CTG GAA          196
Ile Ser Leu Gln Cys Cys Asp Ser Leu Thr Arg Asn His His Leu Glu
             45                  50                  55

CTG TCC CTG CAC CTC GGT AAG AAA GAT GAG GTG GTG ATT AAG GTG CAC          244
Leu Ser Leu His Leu Gly Lys Lys Asp Glu Val Val Ile Lys Val His
         60                  65                  70

AAT GAG CCT GAG GCT GGA GGC AAG TGG TGG TTT AAC CAT CAG AAA GTG          292
Asn Glu Pro Glu Ala Gly Gly Lys Trp Trp Phe Asn His Gln Lys Val
     75                  80                  85

CAG GAT GAA ATT CTG CTG ACT CTA CAC AGT CCA GCG GAC GCC ATA ATT          340
Gln Asp Glu Ile Leu Leu Thr Leu His Ser Pro Ala Asp Ala Ile Ile
 90                  95                 100                 105

GGC GAG TAC CAC CTG ACT GTG TTG ATC AAG TCA CCG GAT GGA CAC TTT          388
```

|  |  |  |  |  |  |  |  |  |  |  |  |  |  |  |
|---|---|---|---|---|---|---|---|---|---|---|---|---|---|---|
| Gly | Glu | Tyr | His | Leu | Thr | Val | Leu | Ile | Lys | Ser | Pro | Asp | Gly | His | Phe |
|  |  |  |  | 110 |  |  |  |  | 115 |  |  |  |  | 120 |  |

```
GTG AAG AAG ACT AAG AAC ATT GGA TTC CAC CTG CTC TTT AAC CCC TGG    436
Val Lys Lys Thr Lys Asn Ile Gly Phe His Leu Leu Phe Asn Pro Trp
        125             130                 135

TGC AAA GAT GAT GCT GTG TAC CTC CCT GAT GAA AGG ATG CTC GAC GAG    484
Cys Lys Asp Asp Ala Val Tyr Leu Pro Asp Glu Arg Met Leu Asp Glu
        140             145                 150

TAT GTT ATG AAT GAG GAG GGG ATC ATT TAC AGG GGA ACC TCG AAT CAC    532
Tyr Val Met Asn Glu Glu Gly Ile Ile Tyr Arg Gly Thr Ser Asn His
        155             160                 165

ATC AGT AGC ATA CCC TGG AAT TAC GGA CAG TTT GAG GAC TAT GTG ATG    580
Ile Ser Ser Ile Pro Trp Asn Tyr Gly Gln Phe Glu Asp Tyr Val Met
170             175                 180                     185

GAC ATC TGT TTT CAA GTT CTG GAC AAC TCC AAG GAA GCC CTG AAG AAT    628
Asp Ile Cys Phe Gln Val Leu Asp Asn Ser Lys Glu Ala Leu Lys Asn
                190                 195                 200

TCA AAG ATG GAC ATT GAG AAG AGA TCT GAC CCT GTC TAT GTC AGC AGG    676
Ser Lys Met Asp Ile Glu Lys Arg Ser Asp Pro Val Tyr Val Ser Arg
        205                 210                 215

ATG ATC ACT GCG ATG GTG AAC TCT AAC GGT GAC AGG GGT GTG CTG ACT    724
Met Ile Thr Ala Met Val Asn Ser Asn Gly Asp Arg Gly Val Leu Thr
        220                 225                 230

GGT CAG TGG CAC GAG CCA TAC ACT GGC GGG TTC TCA CCA CTT CGA TGG    772
Gly Gln Trp His Glu Pro Tyr Thr Gly Gly Phe Ser Pro Leu Arg Trp
    235                 240                 245

ACC GGC AGC GTG CCC ATC CTC CGG AAG TGG AGC AAG GCC GAG GTC AGG    820
Thr Gly Ser Val Pro Ile Leu Arg Lys Trp Ser Lys Ala Glu Val Arg
250                 255                 260                 265

GCG GTC AAA TAT GGC CAG TGC TGG GTG TTT GCT GCT GTC GCC TGC ACA    868
Ala Val Lys Tyr Gly Gln Cys Trp Val Phe Ala Ala Val Ala Cys Thr
                270                 275                 280

GTG CTG CGT TGT CTG GGA ATC CCA ACA CGC AAC ATC ACT AAC TTC AAT    916
Val Leu Arg Cys Leu Gly Ile Pro Thr Arg Asn Ile Thr Asn Phe Asn
            285                 290                 295

TCA GCA CAT GAT GTC GAT GGA AAC CTC TCC GTC GAC ATC GTG TTG AAC    964
Ser Ala His Asp Val Asp Gly Asn Leu Ser Val Asp Ile Val Leu Asn
        300                 305                 310

AAA GAA ATG GAG AGC GTT GGC AAG AAG GAC AGT AGC TGG AAC TTC CAC   1012
Lys Glu Met Glu Ser Val Gly Lys Lys Asp Ser Ser Trp Asn Phe His
315                 320                 325

TGT TGG ATC GAG TCC TGG ATG AGG AGA GAC GAC CTC TCT AAA GGA AAT   1060
Cys Trp Ile Glu Ser Trp Met Arg Arg Asp Asp Leu Ser Lys Gly Asn
330                 335                 340                 345

GAC GGC TGG CAG GTT TTG GAC CCC ACC CCT CAA GAA CTG AGT GAT GGT   1108
Asp Gly Trp Gln Val Leu Asp Pro Thr Pro Gln Glu Leu Ser Asp Gly
                350                 355                 360

GAG TAT TGC TGC GGC CCG TGT CCA GTC ACC GCC ATC AAG GAG GGA AAT   1156
Glu Tyr Cys Cys Gly Pro Cys Pro Val Thr Ala Ile Lys Glu Gly Asn
            365                 370                 375

CTG AGT GTG AAG TAC GAC GCT CCG TTT ATC TTC GCT GAG GTG AAC GCT   1204
Leu Ser Val Lys Tyr Asp Ala Pro Phe Ile Phe Ala Glu Val Asn Ala
        380                 385                 390

GAC ATC ATC TAC TGG ATG GCT GGA CCA GGA GGC GAA CGG AAG AAG ATC   1252
Asp Ile Ile Tyr Trp Met Ala Gly Pro Gly Gly Glu Arg Lys Lys Ile
        395                 400                 405

GAT GTG GAC CAG AGT GGT GTG GGG AAG AAC ATC AGC ACC AAA AGT CTT   1300
Asp Val Asp Gln Ser Gly Val Gly Lys Asn Ile Ser Thr Lys Ser Leu
410                 415                 420                 425

TAT GGC GAC TAC AGG GAG GAT GTC ACT CTG CAC TAC AAA TAC CCC GAA   1348
```

|     |     |     |     |     |     |     |     |     |     |     |     |     |     |     |     |      |
| --- | --- | --- | --- | --- | --- | --- | --- | --- | --- | --- | --- | --- | --- | --- | --- | --- |
| Tyr | Gly | Asp | Tyr | Arg | Glu | Asp | Val | Thr | Leu | His | Tyr | Lys | Tyr | Pro | Glu |      |
|     |     |     |     | 430 |     |     |     | 435 |     |     |     |     |     | 440 |     |      |
| GGC | TCC | AAG | AAG | GAG | AGA | GAG | GTG | TAC | CAG | AAG | GCC | GGA | CAC | CGA | ATC | 1396 |
| Gly | Ser | Lys | Lys | Glu | Arg | Glu | Val | Tyr | Gln | Lys | Ala | Gly | His | Arg | Ile |      |
|     |     |     | 445 |     |     |     |     | 450 |     |     |     |     | 455 |     |     |      |
| AAA | GAG | CAG | ATC | TGT | GAA | AAC | AAA | GGT | CCA | CAA | CAA | CTG | CAG | CTG | TCA | 1444 |
| Lys | Glu | Gln | Ile | Cys | Glu | Asn | Lys | Gly | Pro | Gln | Gln | Leu | Gln | Leu | Ser |      |
|     |     | 460 |     |     |     |     | 465 |     |     |     |     | 470 |     |     |     |      |
| GTC | AAG | CAC | GGG | AAA | CCT | GTA | TTT | GGC | ACT | GAC | TTC | GAT | GTG | ATA | GTT | 1492 |
| Val | Lys | His | Gly | Lys | Pro | Val | Phe | Gly | Thr | Asp | Phe | Asp | Val | Ile | Val |      |
|     | 475 |     |     |     |     | 480 |     |     |     |     | 485 |     |     |     |     |      |
| GAG | GTG | AAG | AAT | GAA | GGA | CAG | AAA | GAC | ACC | AGT | CCA | CAG | CTG | CTG | ATT | 1540 |
| Glu | Val | Lys | Asn | Glu | Gly | Gln | Lys | Asp | Thr | Ser | Pro | Gln | Leu | Leu | Ile |      |
| 490 |     |     |     |     | 495 |     |     |     |     | 500 |     |     |     |     | 505 |      |
| GTG | GTC | ATG | GCC | GTG | ACC | TAC | AAT | TCC | ATC | AAT | CAA | GGG | GAG | TGT | CAG | 1588 |
| Val | Val | Met | Ala | Val | Thr | Tyr | Asn | Ser | Ile | Asn | Gln | Gly | Glu | Cys | Gln |      |
|     |     |     |     | 510 |     |     |     |     | 515 |     |     |     |     | 520 |     |      |
| AGG | AAG | GCG | ACC | ATA | GTG | ACC | GTG | CCG | GCT | CGC | AAA | ACC | CAC | AAG | GAA | 1636 |
| Arg | Lys | Ala | Thr | Ile | Val | Thr | Val | Pro | Ala | Arg | Lys | Thr | His | Lys | Glu |      |
|     |     |     | 525 |     |     |     |     | 530 |     |     |     |     | 535 |     |     |      |
| GTG | CTG | CGT | CTG | CGC | TAC | GAC | GAC | TAT | GTC | AAA | TGT | GTC | TCT | GAG | CAC | 1684 |
| Val | Leu | Arg | Leu | Arg | Tyr | Asp | Asp | Tyr | Val | Lys | Cys | Val | Ser | Glu | His |      |
|     |     | 540 |     |     |     |     | 545 |     |     |     |     | 550 |     |     |     |      |
| CAT | CTG | ATC | AGG | GTG | AAA | GCG | CTC | ATG | GAG | GTT | CCA | GGG | GAC | AAC | AAA | 1732 |
| His | Leu | Ile | Arg | Val | Lys | Ala | Leu | Met | Glu | Val | Pro | Gly | Asp | Asn | Lys |      |
|     | 555 |     |     |     |     | 560 |     |     |     |     | 565 |     |     |     |     |      |
| CCC | GTC | ATG | AGT | GTG | GCC | AAC | ATT | CCA | CTG | AGC | ATG | CCT | GAG | CTC | CTG | 1780 |
| Pro | Val | Met | Ser | Val | Ala | Asn | Ile | Pro | Leu | Ser | Met | Pro | Glu | Leu | Leu |      |
| 570 |     |     |     |     | 575 |     |     |     |     | 580 |     |     |     |     | 585 |      |
| GTA | GAG | GTA | CCT | GGG | AGC | ATC | ATT | GTT | CAG | GAG | AAG | GTG | ACA | GCC | TTC | 1828 |
| Val | Glu | Val | Pro | Gly | Ser | Ile | Ile | Val | Gln | Glu | Lys | Val | Thr | Ala | Phe |      |
|     |     |     |     | 590 |     |     |     |     | 595 |     |     |     |     | 600 |     |      |
| ATC | TCC | TTC | ACA | AAT | CCT | CTA | ACT | GTC | CCA | CTG | AAG | CGT | GGC | ATG | TTC | 1876 |
| Ile | Ser | Phe | Thr | Asn | Pro | Leu | Thr | Val | Pro | Leu | Lys | Arg | Gly | Met | Phe |      |
|     |     |     | 605 |     |     |     |     | 610 |     |     |     |     | 615 |     |     |      |
| ACC | GTT | GAG | GGG | TCC | GGA | CTA | CTG | TCT | GCC | TCT | GAG | ATC | TAT | GTG | AAA | 1924 |
| Thr | Val | Glu | Gly | Ser | Gly | Leu | Leu | Ser | Ala | Ser | Glu | Ile | Tyr | Val | Lys |      |
|     |     | 620 |     |     |     |     | 625 |     |     |     |     | 630 |     |     |     |      |
| GGG | GAC | ATT | GCT | CCA | GGC | CAG | AAG | GTT | TCT | GTC | AAG | ATC | ACC | TTC | ACG | 1972 |
| Gly | Asp | Ile | Ala | Pro | Gly | Gln | Lys | Val | Ser | Val | Lys | Ile | Thr | Phe | Thr |      |
|     | 635 |     |     |     |     | 640 |     |     |     |     | 645 |     |     |     |     |      |
| CCC | ATG | AGG | GTC | GGG | GTG | AGG | AAG | CTC | CTG | GTG | GAC | TTT | GAC | TCT | GAC | 2020 |
| Pro | Met | Arg | Val | Gly | Val | Arg | Lys | Leu | Leu | Val | Asp | Phe | Asp | Ser | Asp |      |
| 650 |     |     |     |     | 655 |     |     |     |     | 660 |     |     |     |     | 665 |      |
| AGG | CTG | AAG | GAT | GTG | AAA | GGA | GTC | ACG | ACA | GTG | GTC | GTC | CGC | AAG | AAA | 2068 |
| Arg | Leu | Lys | Asp | Val | Lys | Gly | Val | Thr | Thr | Val | Val | Val | Arg | Lys | Lys |      |
|     |     |     |     | 670 |     |     |     |     | 675 |     |     |     |     | 680 |     |      |
| TCC | TGT | TTT | ATT | AGG | TGT | CCT | TAAAAACAGA | | CGGACACGTA | | TTAAAGTGTG | | | | | 2119 |
| Ser | Cys | Phe | Ile | Arg | Cys | Pro |     |     |     |     |     |     |     |     |     |      |
|     |     |     | 685 |     |     |     |     |     |     |     |     |     |     |     |     |      |

AGATAACCTG AGAGGTGTAA CTCCCCTGT                         2148

( 2 ) INFORMATION FOR SEQ ID NO:70:

( i ) SEQUENCE CHARACTERISTICS:
        ( A ) LENGTH: 688 amino acids
        ( B ) TYPE: amino acid
        ( D ) TOPOLOGY: linear ( i i ) MOLECULE TYPE: protein ( x i ) SEQUENCE DESCRIPTION: SEQ ID NO:70:

| | | | | | | | | | | | | | | | |
|---|---|---|---|---|---|---|---|---|---|---|---|---|---|---|---|
| Met | Asp | Asn | Gln | Asn | Ile | Pro | Ile | Thr | Asp | Val | Asp | Val | Arg | Ser | His |
| 1 | | | | 5 | | | | | 10 | | | | | 15 | |
| Glu | Asn | Asn | Leu | Ala | His | Arg | Thr | Arg | Glu | Ile | Asp | Arg | Glu | Arg | Leu |
| | | | 20 | | | | | 25 | | | | | 30 | | |
| Ile | Val | Arg | Arg | Gly | Gln | Pro | Phe | Ser | Ile | Ser | Leu | Gln | Cys | Cys | Asp |
| | | 35 | | | | | 40 | | | | | 45 | | | |
| Ser | Leu | Thr | Arg | Asn | His | His | Leu | Glu | Leu | Ser | Leu | His | Leu | Gly | Lys |
| | | 50 | | | | 55 | | | | | 60 | | | | |
| Lys | Asp | Glu | Val | Val | Ile | Lys | Val | His | Asn | Glu | Pro | Glu | Ala | Gly | Gly |
| 65 | | | | | 70 | | | | 75 | | | | | | 80 |
| Lys | Trp | Trp | Phe | Asn | His | Gln | Lys | Val | Gln | Asp | Glu | Ile | Leu | Leu | Thr |
| | | | | 85 | | | | | 90 | | | | | 95 | |
| Leu | His | Ser | Pro | Ala | Asp | Ala | Ile | Ile | Gly | Glu | Tyr | His | Leu | Thr | Val |
| | | | 100 | | | | | 105 | | | | | 110 | | |
| Leu | Ile | Lys | Ser | Pro | Asp | Gly | His | Phe | Val | Lys | Lys | Thr | Lys | Asn | Ile |
| | | 115 | | | | 120 | | | | | 125 | | | | |
| Gly | Phe | His | Leu | Leu | Phe | Asn | Pro | Trp | Cys | Lys | Asp | Asp | Ala | Val | Tyr |
| | 130 | | | | | 135 | | | | | 140 | | | | |
| Leu | Pro | Asp | Glu | Arg | Met | Leu | Asp | Glu | Tyr | Val | Met | Asn | Glu | Glu | Gly |
| 145 | | | | | 150 | | | | | 155 | | | | | 160 |
| Ile | Ile | Tyr | Arg | Gly | Thr | Ser | Asn | His | Ile | Ser | Ser | Ile | Pro | Trp | Asn |
| | | | | 165 | | | | | 170 | | | | | 175 | |
| Tyr | Gly | Gln | Phe | Glu | Asp | Tyr | Val | Met | Asp | Ile | Cys | Phe | Gln | Val | Leu |
| | | | 180 | | | | | 185 | | | | | 190 | | |
| Asp | Asn | Ser | Lys | Glu | Ala | Leu | Lys | Asn | Ser | Lys | Met | Asp | Ile | Glu | Lys |
| | | | 195 | | | | | 200 | | | | | 205 | | |
| Arg | Ser | Asp | Pro | Val | Tyr | Val | Ser | Arg | Met | Ile | Thr | Ala | Met | Val | Asn |
| | 210 | | | | | 215 | | | | | 220 | | | | |
| Ser | Asn | Gly | Asp | Arg | Gly | Val | Leu | Thr | Gly | Gln | Trp | His | Glu | Pro | Tyr |
| 225 | | | | | 230 | | | | | 235 | | | | | 240 |
| Thr | Gly | Gly | Phe | Ser | Pro | Leu | Arg | Trp | Thr | Gly | Ser | Val | Pro | Ile | Leu |
| | | | | 245 | | | | | 250 | | | | | 255 | |
| Arg | Lys | Trp | Ser | Lys | Ala | Glu | Val | Arg | Ala | Val | Lys | Tyr | Gly | Gln | Cys |
| | | | 260 | | | | | 265 | | | | | 270 | | |
| Trp | Val | Phe | Ala | Ala | Val | Ala | Cys | Thr | Val | Leu | Arg | Cys | Leu | Gly | Ile |
| | | | 275 | | | | | 280 | | | | | 285 | | |
| Pro | Thr | Arg | Asn | Ile | Thr | Asn | Phe | Asn | Ser | Ala | His | Asp | Val | Asp | Gly |
| | 290 | | | | | 295 | | | | | 300 | | | | |
| Asn | Leu | Ser | Val | Asp | Ile | Val | Leu | Asn | Lys | Glu | Met | Glu | Ser | Val | Gly |
| 305 | | | | | 310 | | | | | 315 | | | | | 320 |
| Lys | Lys | Asp | Ser | Ser | Trp | Asn | Phe | His | Cys | Trp | Ile | Glu | Ser | Trp | Met |
| | | | | 325 | | | | | 330 | | | | | 335 | |
| Arg | Arg | Asp | Asp | Leu | Ser | Lys | Gly | Asn | Asp | Gly | Trp | Gln | Val | Leu | Asp |
| | | | 340 | | | | | 345 | | | | | 350 | | |
| Pro | Thr | Pro | Gln | Glu | Leu | Ser | Asp | Gly | Glu | Tyr | Cys | Cys | Gly | Pro | Cys |
| | | 355 | | | | | 360 | | | | | 365 | | | |
| Pro | Val | Thr | Ala | Ile | Lys | Glu | Gly | Asn | Leu | Ser | Val | Lys | Tyr | Asp | Ala |
| | | 370 | | | | | 375 | | | | | 380 | | | |
| Pro | Phe | Ile | Phe | Ala | Glu | Val | Asn | Ala | Asp | Ile | Ile | Tyr | Trp | Met | Ala |
| 385 | | | | | 390 | | | | | 395 | | | | | 400 |
| Gly | Pro | Gly | Gly | Glu | Arg | Lys | Lys | Ile | Asp | Val | Asp | Gln | Ser | Gly | Val |
| | | | | 405 | | | | | 410 | | | | | 415 | |
| Gly | Lys | Asn | Ile | Ser | Thr | Lys | Ser | Leu | Tyr | Gly | Asp | Tyr | Arg | Glu | Asp |

|   |   |   |   |   |   |   | 420 |   |   |   | 425 |   |   |   | 430 |   |   |
|---|---|---|---|---|---|---|---|---|---|---|---|---|---|---|---|---|---|

Val Thr Leu His Tyr Lys Tyr Pro Glu Gly Ser Lys Lys Glu Arg Glu
            435                 440             445

Val Tyr Gln Lys Ala Gly His Arg Ile Lys Glu Gln Ile Cys Glu Asn
    450             455                 460

Lys Gly Pro Gln Gln Leu Gln Leu Ser Val Lys His Gly Lys Pro Val
465             470             475                 480

Phe Gly Thr Asp Phe Asp Val Ile Val Glu Val Lys Asn Glu Gly Gln
                485             490                 495

Lys Asp Thr Ser Pro Gln Leu Leu Ile Val Val Met Ala Val Thr Tyr
            500             505                 510

Asn Ser Ile Asn Gln Gly Glu Cys Gln Arg Lys Ala Thr Ile Val Thr
        515             520             525

Val Pro Ala Arg Lys Thr His Lys Glu Val Leu Arg Leu Arg Tyr Asp
    530             535             540

Asp Tyr Val Lys Cys Val Ser Glu His His Leu Ile Arg Val Lys Ala
545             550             555                 560

Leu Met Glu Val Pro Gly Asp Asn Lys Pro Val Met Ser Val Ala Asn
            565             570             575

Ile Pro Leu Ser Met Pro Glu Leu Leu Val Glu Val Pro Gly Ser Ile
        580             585             590

Ile Val Gln Glu Lys Val Thr Ala Phe Ile Ser Phe Thr Asn Pro Leu
    595             600             605

Thr Val Pro Leu Lys Arg Gly Met Phe Thr Val Glu Gly Ser Gly Leu
    610             615             620

Leu Ser Ala Ser Glu Ile Tyr Val Lys Gly Asp Ile Ala Pro Gly Gln
625             630             635             640

Lys Val Ser Val Lys Ile Thr Phe Thr Pro Met Arg Val Gly Val Arg
            645             650             655

Lys Leu Leu Val Asp Phe Asp Ser Asp Arg Leu Lys Asp Val Lys Gly
            660             665             670

Val Thr Thr Val Val Val Arg Lys Lys Ser Cys Phe Ile Arg Cys Pro
        675             680             685

( 2 ) INFORMATION FOR SEQ ID NO:71:

( i ) SEQUENCE CHARACTERISTICS:
        ( A ) LENGTH: 2148 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: Paralichthys olivaceus
        ( F ) TISSUE TYPE: liver ( i x ) FEATURE:
        ( A ) NAME/KEY: CDS
        ( B ) LOCATION: 26..2092

( x i ) SEQUENCE DESCRIPTION: SEQ ID NO:71:

```
GAGAAGACGA GGAAAAAGGT CTGCG ATG GAC AAT CAG AAC ATT CCG ATC ACT          52
                            Met Asp Asn Gln Asn Ile Pro Ile Thr
                             1               5

GAT GTG GAT GTG AGA AGT CAT GAA AAC AAC TTG GCT CAC CGC ACC AGG         100
Asp Val Asp Val Arg Ser His Glu Asn Asn Leu Ala His Arg Thr Arg
 10              15              20                  25

GAG ATT GAT CGG GAG CGC TTG ATC GTC CGC AGG GGT CAA CCC TTC TCC         148
```

|  |  |  |  |  |  |  |  |  |  |  |  |  |  |  |
|---|---|---|---|---|---|---|---|---|---|---|---|---|---|---|
| Glu | Ile | Asp | Arg | Glu 30 | Arg | Leu | Ile | Val 35 | Arg | Gly | Gln | Pro | Phe 40 | Ser |

| ATA | TCT | CTG | CAG | TGC | TGC | GAC | TCG | CTG | ACC | CGG | AAT | CAC | CAT | CTG | GAA | 196 |
|---|---|---|---|---|---|---|---|---|---|---|---|---|---|---|---|---|
| Ile | Ser | Leu | Gln 45 | Cys | Cys | Asp | Ser | Leu 50 | Thr | Arg | Asn | His | His 55 | Leu | Glu | |

| CTG | TCC | CTG | CAC | CTC | GGT | AAG | AAA | GAT | GAG | GTG | GTG | ATT | AAG | GTG | CAC | 244 |
|---|---|---|---|---|---|---|---|---|---|---|---|---|---|---|---|---|
| Leu | Ser | Leu | His 60 | Leu | Gly | Lys | Lys 65 | Asp | Glu | Val | Val | Ile 70 | Lys | Val | His | |

| AAT | GAG | CCT | GAG | GCT | GGA | GGC | AAG | TGG | TGG | TTT | AAC | CAT | CAG | AAA | GTG | 292 |
|---|---|---|---|---|---|---|---|---|---|---|---|---|---|---|---|---|
| Asn | Glu 75 | Pro | Glu | Ala | Gly | Gly 80 | Lys | Trp | Trp | Phe | Asn 85 | His | Gln | Lys | Val | |

| CAG | GAT | GAA | ATT | CTG | CTG | ACT | CTA | CAC | AGT | CCA | GCG | GAC | GCC | ATA | ATT | 340 |
|---|---|---|---|---|---|---|---|---|---|---|---|---|---|---|---|---|
| Gln 90 | Asp | Glu | Ile | Leu | Leu 95 | Thr | Leu | His | Ser | Pro 100 | Ala | Asp | Ala | Ile | Ile 105 | |

| GGC | GAG | TAC | CAC | CTG | ACT | GTG | TTG | ATC | AAG | TCA | CCG | GAT | GGA | CAC | TTT | 388 |
|---|---|---|---|---|---|---|---|---|---|---|---|---|---|---|---|---|
| Gly | Glu | Tyr | His | Leu 110 | Thr | Val | Leu | Ile | Lys 115 | Ser | Pro | Asp | Gly | His 120 | Phe | |

| GTG | AAG | AAG | ACT | AAG | AAC | ATT | GGA | TTC | CAC | CTG | CTC | TTT | AAC | CCC | TGG | 436 |
|---|---|---|---|---|---|---|---|---|---|---|---|---|---|---|---|---|
| Val | Lys | Lys | Thr 125 | Lys | Asn | Ile | Gly | Phe 130 | His | Leu | Leu | Phe | Asn 135 | Pro | Trp | |

| TGC | AAA | GAT | GAT | GCT | GTG | TAC | CTC | CCT | GAT | GAA | AGG | ATG | CTC | GAC | GAG | 484 |
|---|---|---|---|---|---|---|---|---|---|---|---|---|---|---|---|---|
| Cys | Lys | Asp | Asp 140 | Ala | Val | Tyr | Leu | Pro 145 | Asp | Glu | Arg | Met | Leu 150 | Asp | Glu | |

| TAT | GTT | ATG | AAT | GAG | GAG | GGG | ATC | ATT | TAC | AGG | GGA | ACC | TCG | AAT | CAC | 532 |
|---|---|---|---|---|---|---|---|---|---|---|---|---|---|---|---|---|
| Tyr | Val | Met 155 | Asn | Glu | Glu | Gly | Ile 160 | Ile | Tyr | Arg | Gly | Thr 165 | Ser | Asn | His | |

| ATC | AGT | AGC | ATA | CCC | TGG | AAT | TAC | GGA | CAG | TTT | GAG | GAC | TAT | GTG | ATG | 580 |
|---|---|---|---|---|---|---|---|---|---|---|---|---|---|---|---|---|
| Ile 170 | Ser | Ser | Ile | Pro | Trp 175 | Asn | Tyr | Gly | Gln | Phe 180 | Glu | Asp | Tyr | Val | Met 185 | |

| GAC | ATC | TGT | TTT | CAA | GTT | CTG | GAC | AAC | TCC | AAG | GAA | GCC | CTG | AAG | AAT | 628 |
|---|---|---|---|---|---|---|---|---|---|---|---|---|---|---|---|---|
| Asp | Ile | Cys | Phe | Gln 190 | Val | Leu | Asp | Asn | Ser 195 | Lys | Glu | Ala | Leu | Lys 200 | Asn | |

| TCA | AAG | ATG | GAC | ATT | GAG | AAG | AGA | TCT | GAC | CCT | GTC | TAT | GTC | AGC | AGG | 676 |
|---|---|---|---|---|---|---|---|---|---|---|---|---|---|---|---|---|
| Ser | Lys | Met | Asp 205 | Ile | Glu | Lys | Arg | Ser 210 | Asp | Pro | Val | Tyr | Val 215 | Ser | Arg | |

| ATG | ATC | ACT | GCG | ATG | GTG | AAC | TCT | AAC | GGT | GAC | AGG | GGT | GTG | CTG | ACT | 724 |
|---|---|---|---|---|---|---|---|---|---|---|---|---|---|---|---|---|
| Met | Ile | Thr | Ala 220 | Met | Val | Asn | Ser | Asn 225 | Gly | Asp | Arg | Gly | Val 230 | Leu | Thr | |

| GGT | CAG | TGG | CAC | GAG | CCA | TAC | ACT | GGC | GGG | TTC | TCA | CCA | CTT | CGA | TGG | 772 |
|---|---|---|---|---|---|---|---|---|---|---|---|---|---|---|---|---|
| Gly | Gln | Trp 235 | His | Glu | Pro | Tyr | Thr 240 | Gly | Gly | Phe | Ser | Pro 245 | Leu | Arg | Trp | |

| ACC | GGC | AGC | GTG | CCC | ATC | CTC | CGG | AAG | TGG | AGC | AAG | GCC | GAG | GTC | AGG | 820 |
|---|---|---|---|---|---|---|---|---|---|---|---|---|---|---|---|---|
| Thr 250 | Gly | Ser | Val | Pro | Ile 255 | Leu | Arg | Lys | Trp | Ser 260 | Lys | Ala | Glu | Val | Arg 265 | |

| GCG | GTC | AAA | TAT | GGC | CAG | TGC | TGG | GTG | TTT | GCT | GCT | GTC | GCC | TGC | ACA | 868 |
|---|---|---|---|---|---|---|---|---|---|---|---|---|---|---|---|---|
| Ala | Val | Lys | Tyr | Gly 270 | Gln | Cys | Trp | Val | Phe 275 | Ala | Ala | Val | Ala | Cys 280 | Thr | |

| GTG | CTG | CGT | TGT | CTG | GGA | ATC | CCA | ACA | CGC | AAC | ATC | ACT | AAC | TTC | AAT | 916 |
|---|---|---|---|---|---|---|---|---|---|---|---|---|---|---|---|---|
| Val | Leu | Arg | Cys 285 | Leu | Gly | Ile | Pro | Thr 290 | Arg | Asn | Ile | Thr | Asn 295 | Phe | Asn | |

| TCA | GCA | CAT | GAT | GTC | GAT | GGA | AAC | CTC | TCC | GTC | GAC | ATC | GTG | TTG | AAC | 964 |
|---|---|---|---|---|---|---|---|---|---|---|---|---|---|---|---|---|
| Ser | Ala | His | Asp 300 | Val | Asp | Gly | Asn | Leu 305 | Ser | Val | Asp | Ile | Val 310 | Leu | Asn | |

| AAA | GAA | ATG | GAG | AGC | GTT | GGC | AAG | AAG | GAC | AGT | AGC | TGG | AAC | TTC | CAC | 1012 |
|---|---|---|---|---|---|---|---|---|---|---|---|---|---|---|---|---|
| Lys | Glu | Met 315 | Glu | Ser | Val | Gly | Lys 320 | Lys | Asp | Ser | Ser | Trp 325 | Asn | Phe | His | |

| TGT | TGG | ATC | GAG | TCC | TGG | ATG | AGG | AGA | GAC | GAC | CTC | TCT | AAA | GGA | AAT | 1060 |
|---|---|---|---|---|---|---|---|---|---|---|---|---|---|---|---|---|
| Cys | Trp | Ile | Glu | Ser 330 | Trp | Met | Arg | Arg | Asp 335 | Asp | Leu | Ser | Lys | Gly 340 | Asn 345 | |

| GAC | GGC | TGG | CAG | GTT | TTG | GAC | CCC | ACC | CCT | CAA | GAA | CTG | AGT | GAT | GGT | 1108 |

```
Asp Gly Trp Gln Val Leu Asp Pro Thr Pro Gln Glu Leu Ser Asp Gly
            350                 355                 360

GAG TAT TGC TGC GGC CCG TGT CCA GTC ACC GCC ATC AAG GAG GGA AAT    1156
Glu Tyr Cys Cys Gly Pro Cys Pro Val Thr Ala Ile Lys Glu Gly Asn
            365                 370                 375

CTG AGT GTG AAG TAC GAC GCT CCG TTT ATC TTC GCT GAG GTG AAC GCT    1204
Leu Ser Val Lys Tyr Asp Ala Pro Phe Ile Phe Ala Glu Val Asn Ala
        380                 385                 390

GAC ATC ATC TAC TGG ATG GCT GGA CCA GGA GGC GAA CGG AAG AAG ATC    1252
Asp Ile Ile Tyr Trp Met Ala Gly Pro Gly Gly Glu Arg Lys Lys Ile
    395                 400                 405

GAT GTG GAC CAG AGT GGT GTG GGG AAG AAC ATC AGC ACC AAA AGT CTT    1300
Asp Val Asp Gln Ser Gly Val Gly Lys Asn Ile Ser Thr Lys Ser Leu
410                 415                 420                 425

TAT GGC GAC TAC AGG GAG GAT GTC ACT CTG CAC TAC AAA TAC CCC GAA    1348
Tyr Gly Asp Tyr Arg Glu Asp Val Thr Leu His Tyr Lys Tyr Pro Glu
                430                 435                 440

GGC TCC AAG AAG GAG AGA GAG GTG TAC CAG AAG GCC GGA CAC CGA ATC    1396
Gly Ser Lys Lys Glu Arg Glu Val Tyr Gln Lys Ala Gly His Arg Ile
            445                 450                 455

AAA GAG CAG ATC TGT GAA AAC AAA GGT CCA CAA CAA CTG CAG CTG TCA    1444
Lys Glu Gln Ile Cys Glu Asn Lys Gly Pro Gln Gln Leu Gln Leu Ser
        460                 465                 470

GTC AAG CAC GGG AAA CCT GTA TTT GGC ACT GAC TTC GAT GTG ATA GTT    1492
Val Lys His Gly Lys Pro Val Phe Gly Thr Asp Phe Asp Val Ile Val
    475                 480                 485

GAG GTG AAG AAT GAA GGA CAG AAA GAC ACC AGT CCA CAG CTG CTG ATT    1540
Glu Val Lys Asn Glu Gly Gln Lys Asp Thr Ser Pro Gln Leu Leu Ile
490                 495                 500                 505

GTG GTC ATG GCC GTG ACC TAC AAT TCC ATC AAT CAA GGG GAG TGT CAG    1588
Val Val Met Ala Val Thr Tyr Asn Ser Ile Asn Gln Gly Glu Cys Gln
                510                 515                 520

AGG AAG GCG ACC ATA GTG ACC GTG CCG GCT CGC AAA ACC CAC AAG GAA    1636
Arg Lys Ala Thr Ile Val Thr Val Pro Ala Arg Lys Thr His Lys Glu
            525                 530                 535

GTG CTG CGT CTG CGC TAC GAC GAC TAT GTC AAA TGT GTC TCT GAG CAC    1684
Val Leu Arg Leu Arg Tyr Asp Asp Tyr Val Lys Cys Val Ser Glu His
        540                 545                 550

CAT CTG ATC AGG GTG AAA GCG CTC ATG GAG GTT CCA GGG GAC AAC AAA    1732
His Leu Ile Arg Val Lys Ala Leu Met Glu Val Pro Gly Asp Asn Lys
    555                 560                 565

CCC GTC ATG AGT GTG GCC AAC ATT CCA CTG AGC ATG CCT GAG CTC CTG    1780
Pro Val Met Ser Val Ala Asn Ile Pro Leu Ser Met Pro Glu Leu Leu
570                 575                 580                 585

GTA GAG GTA CCT GGG AGC ATC ATT GTT CAG GAG AAG GTG ACA GCC TTC    1828
Val Glu Val Pro Gly Ser Ile Ile Val Gln Glu Lys Val Thr Ala Phe
                590                 595                 600

ATC TCC TTC ACA AAT CCT CTA ACT GTC CCA CTG AAG CGT GGC ATG TTC    1876
Ile Ser Phe Thr Asn Pro Leu Thr Val Pro Leu Lys Arg Gly Met Phe
            605                 610                 615

ACC GTG GAG GGG TCC GGA CTA CTG TCT GCC TCT GAG ATC TAT GTG AAA    1924
Thr Val Glu Gly Ser Gly Leu Leu Ser Ala Ser Glu Ile Tyr Val Lys
        620                 625                 630

GGG GAC ATT GCT CCA GGC CAG AAG GTT TCT GTC AAG ATC ACC TTC ACG    1972
Gly Asp Ile Ala Pro Gly Gln Lys Val Ser Val Lys Ile Thr Phe Thr
    635                 640                 645

CCC ATG AGG GTC GGG GTG AGG AAG CTC CTG GTG GAC TTT GAC TCT GAC    2020
Pro Met Arg Val Gly Val Arg Lys Leu Leu Val Asp Phe Asp Ser Asp
650                 655                 660                 665

AGG CTG AAG GAT GTG AAA GGA GTC ACG ACA GTG GTC GTC CGC AAG AAA    2068
```

```
Arg  Leu  Lys  Asp  Val  Lys  Gly  Val  Thr  Thr  Val  Val  Val  Arg  Lys  Lys
               670            675                           680

TCC  TGT  TTT  ATT  AGG  TGT  CCT  TAAAAACAGA  CGGACACGTA  TTAAAGTGTG                 2119
Ser  Cys  Phe  Ile  Arg  Cys  Pro
               685

AGATAACCTG  AGAGGTGTAA  CTCCCCTGT                                                      2148
```

( 2 ) INFORMATION FOR SEQ ID NO:72:

( i ) SEQUENCE CHARACTERISTICS:
        ( A ) LENGTH: 688 amino acids
        ( B ) TYPE: amino acid
        ( D ) TOPOLOGY: linear ( i i ) MOLECULE TYPE: protein ( x i ) SEQUENCE DESCRIPTION: SEQ ID NO:72:

```
Met  Asp  Asn  Gln  Asn  Ile  Pro  Ile  Thr  Asp  Val  Asp  Val  Arg  Ser  His
1                        5                   10                          15

Glu  Asn  Asn  Leu  Ala  His  Arg  Thr  Arg  Glu  Ile  Asp  Arg  Glu  Arg  Leu
               20                       25                      30

Ile  Val  Arg  Arg  Gly  Gln  Pro  Phe  Ser  Ile  Ser  Leu  Gln  Cys  Cys  Asp
          35                      40                      45

Ser  Leu  Thr  Arg  Asn  His  His  Leu  Glu  Leu  Ser  Leu  His  Leu  Gly  Lys
     50                       55                      60

Lys  Asp  Glu  Val  Val  Ile  Lys  Val  His  Asn  Glu  Pro  Glu  Ala  Gly  Gly
65                       70                  75                            80

Lys  Trp  Trp  Phe  Asn  His  Gln  Lys  Val  Gln  Asp  Glu  Ile  Leu  Leu  Thr
               85                       90                          95

Leu  His  Ser  Pro  Ala  Asp  Ala  Ile  Ile  Gly  Glu  Tyr  His  Leu  Thr  Val
               100                      105                     110

Leu  Ile  Lys  Ser  Pro  Asp  Gly  His  Phe  Val  Lys  Lys  Thr  Lys  Asn  Ile
          115                      120                     125

Gly  Phe  His  Leu  Leu  Phe  Asn  Pro  Trp  Cys  Lys  Asp  Asp  Ala  Val  Tyr
     130                      135                 140

Leu  Pro  Asp  Glu  Arg  Met  Leu  Asp  Glu  Tyr  Val  Met  Asn  Glu  Glu  Gly
145                      150                 155                         160

Ile  Ile  Tyr  Arg  Gly  Thr  Ser  Asn  His  Ile  Ser  Ser  Ile  Pro  Trp  Asn
               165                      170                     175

Tyr  Gly  Gln  Phe  Glu  Asp  Tyr  Val  Met  Asp  Ile  Cys  Phe  Gln  Val  Leu
               180                      185                     190

Asp  Asn  Ser  Lys  Glu  Ala  Leu  Lys  Asn  Ser  Lys  Met  Asp  Ile  Glu  Lys
               195                      200                     205

Arg  Ser  Asp  Pro  Val  Tyr  Val  Ser  Arg  Met  Ile  Thr  Ala  Met  Val  Asn
     210                      215                 220

Ser  Asn  Gly  Asp  Arg  Gly  Val  Leu  Thr  Gly  Gln  Trp  His  Glu  Pro  Tyr
225                      230                 235                         240

Thr  Gly  Gly  Phe  Ser  Pro  Leu  Arg  Trp  Thr  Gly  Ser  Val  Pro  Ile  Leu
               245                      250                     255

Arg  Lys  Trp  Ser  Lys  Ala  Glu  Val  Arg  Ala  Val  Lys  Tyr  Gly  Gln  Cys
               260                      265                     270

Trp  Val  Phe  Ala  Ala  Val  Ala  Cys  Thr  Val  Leu  Arg  Cys  Leu  Gly  Ile
               275                      280                     285

Pro  Thr  Arg  Asn  Ile  Thr  Asn  Phe  Asn  Ser  Ala  His  Asp  Val  Asp  Gly
     290                      295                 300

Asn  Leu  Ser  Val  Asp  Ile  Val  Leu  Asn  Lys  Glu  Met  Glu  Ser  Val  Gly
305                      310                 315                         320
```

| | | | | | | | | | | | | | | | |
|---|---|---|---|---|---|---|---|---|---|---|---|---|---|---|---|
| Lys | Lys | Asp | Ser | Ser 325 | Trp | Asn | Phe | His | Cys 330 | Trp | Ile | Glu | Ser | Trp 335 | Met |
| Arg | Arg | Asp | Asp 340 | Leu | Ser | Lys | Gly | Asn 345 | Asp | Gly | Trp | Gln | Val 350 | Leu | Asp |
| Pro | Thr | Pro 355 | Gln | Glu | Leu | Ser | Asp 360 | Gly | Glu | Tyr | Cys | Cys 365 | Gly | Pro | Cys |
| Pro | Val 370 | Thr | Ala | Ile | Lys | Glu 375 | Gly | Asn | Leu | Ser | Val 380 | Lys | Tyr | Asp | Ala |
| Pro 385 | Phe | Ile | Phe | Ala | Glu 390 | Val | Asn | Ala | Asp | Ile 395 | Ile | Tyr | Trp | Met | Ala 400 |
| Gly | Pro | Gly | Gly | Glu 405 | Arg | Lys | Lys | Ile | Asp 410 | Val | Asp | Gln | Ser | Gly 415 | Val |
| Gly | Lys | Asn | Ile 420 | Ser | Thr | Lys | Ser | Leu 425 | Tyr | Gly | Asp | Tyr | Arg 430 | Glu | Asp |
| Val | Thr | Leu 435 | His | Tyr | Lys | Tyr | Pro 440 | Glu | Gly | Ser | Lys | Lys 445 | Glu | Arg | Glu |
| Val | Tyr 450 | Gln | Lys | Ala | Gly | His 455 | Arg | Ile | Lys | Glu | Gln 460 | Ile | Cys | Glu | Asn |
| Lys 465 | Gly | Pro | Gln | Gln | Leu 470 | Gln | Leu | Ser | Val | Lys 475 | His | Gly | Lys | Pro | Val 480 |
| Phe | Gly | Thr | Asp | Phe 485 | Asp | Val | Ile | Val | Glu 490 | Val | Lys | Asn | Glu | Gly 495 | Gln |
| Lys | Asp | Thr | Ser 500 | Pro | Gln | Leu | Leu | Ile 505 | Val | Val | Met | Ala | Val 510 | Thr | Tyr |
| Asn | Ser | Ile 515 | Asn | Gln | Gly | Glu | Cys 520 | Gln | Arg | Lys | Ala | Thr 525 | Ile | Val | Thr |
| Val | Pro 530 | Ala | Arg | Lys | Thr | His 535 | Lys | Glu | Val | Leu | Arg 540 | Leu | Arg | Tyr | Asp |
| Asp 545 | Tyr | Val | Lys | Cys | Val 550 | Ser | Glu | His | His | Leu 555 | Ile | Arg | Val | Lys | Ala 560 |
| Leu | Met | Glu | Val | Pro 565 | Gly | Asp | Asn | Lys | Pro 570 | Val | Met | Ser | Val | Ala 575 | Asn |
| Ile | Pro | Leu | Ser 580 | Met | Pro | Glu | Leu | Leu 585 | Val | Glu | Val | Pro | Gly 590 | Ser | Ile |
| Ile | Val | Gln 595 | Glu | Lys | Val | Thr | Ala 600 | Phe | Ile | Ser | Phe | Thr 605 | Asn | Pro | Leu |
| Thr | Val 610 | Pro | Leu | Lys | Arg | Gly 615 | Met | Phe | Thr | Val | Glu 620 | Gly | Ser | Gly | Leu |
| Leu 625 | Ser | Ala | Ser | Glu | Ile 630 | Tyr | Val | Lys | Gly | Asp 635 | Ile | Ala | Pro | Gly | Gln 640 |
| Lys | Val | Ser | Val | Lys 645 | Ile | Thr | Phe | Thr | Pro 650 | Met | Arg | Val | Gly | Val 655 | Arg |
| Lys | Leu | Leu | Val 660 | Asp | Phe | Asp | Ser | Asp 665 | Arg | Leu | Lys | Asp | Val 670 | Lys | Gly |
| Val | Thr | Thr 675 | Val | Val | Val | Arg | Lys 680 | Lys | Ser | Cys | Phe | Ile 685 | Arg | Cys | Pro |